United States Patent
Li et al.

(10) Patent No.: US 9,693,555 B2
(45) Date of Patent: Jul. 4, 2017

(54) INSECT-COMBATING PREPARATION AND METHOD BASED ON RNAI TECHNOLOGY

(75) Inventors: Haichao Li, Shanghai (CN); Xuexia Miao, Shanghai (CN); Hao Zhang, Shanghai (CN); Yubing Wang, Shanghai (CN); Yongping Huang, Shanghai (CN)

(73) Assignee: Shanghai Institutes for Biological Sciences, Chinese Academy of Sciences, Shanghai (CN)

( * ) Notice: Subject to any disclaimer, the term of this patent is extended or adjusted under 35 U.S.C. 154(b) by 385 days.

(21) Appl. No.: 14/006,003

(22) PCT Filed: Mar. 19, 2012

(86) PCT No.: PCT/CN2012/000333
§ 371 (c)(1),
(2), (4) Date: Sep. 18, 2013

(87) PCT Pub. No.: WO2012/126276
PCT Pub. Date: Sep. 27, 2012

(65) Prior Publication Data
US 2014/0150134 A1    May 29, 2014

(30) Foreign Application Priority Data

Mar. 18, 2011 (CN) .......................... 2011 1 0067359

(51) Int. Cl.
| | | |
|---|---|---|
| A01N 43/16 | (2006.01) | |
| C12N 15/82 | (2006.01) | |
| C07K 14/435 | (2006.01) | |
| A01N 37/46 | (2006.01) | |
| A01N 63/02 | (2006.01) | |
| C12N 15/113 | (2010.01) | |

(52) U.S. Cl.
CPC ............ *A01N 43/16* (2013.01); *A01N 37/46* (2013.01); *A01N 63/02* (2013.01); *C07K 14/43563* (2013.01); *C12N 15/8218* (2013.01); *C12N 15/8286* (2013.01); *C12N 15/113* (2013.01); *C12N 2310/14* (2013.01)

(58) Field of Classification Search
CPC .................................................... A01N 43/16
USPC ........................................................ 800/279
See application file for complete search history.

(56) References Cited

U.S. PATENT DOCUMENTS

| | | | |
|---|---|---|---|
| 8,735,560 B1* | 5/2014 | English ................ | C07K 14/325 435/419 |
| 2005/0266561 A1* | 12/2005 | Wells ................. | A01K 67/0275 435/455 |
| 2010/0050294 A1 | 2/2010 | Chen et al. | |
| 2012/0164205 A1* | 6/2012 | Baum .................... | A01N 63/02 424/409 |

FOREIGN PATENT DOCUMENTS

| | | |
|---|---|---|
| CN | 101195821 A | 6/2008 |
| WO | 2007/095496 A2 | 8/2007 |

OTHER PUBLICATIONS

Veiga et al (2005) Gene 355: 11-27.*
Hwang et al, Biotechnology Letters (2004) 26: 1469-1473.*
Khurana et al, Protoplasma (2002) 219: 1-12.*
Espacenet English Abstract for CN-101195821, published Jun. 11, 2008 (1 page).
GenBankAccesion No. AAR23823, version AAR23823.1; "Lim protein [Bombyx mori]"; Dec. 1, 2005 (Jan. 12, 2005); retrieved from GenBank database www.ncbi.nlm.nih.gov (1 page).
GenBank Accesion No. AAV91410, version AAV91410.1; LIM protein 1 [Lonomia obliqua]; Aug. 15, 2005 (Aug. 15, 2005); retrieved from GenBank database www.ncbi.nlm.nih.gov (1 page).
GenBank Accesion No. EHJ72075, version EHJ72075.1; muscle LIM protein isoform 1 [Danaus plexippus]; Nov. 21, 2011 (Nov. 21, 2011); retrieved from GenBank database www.ncbi.nlm.nih.gov (2 pages).
International Search Report mailed Jun. 28, 2012, by the State Intellectual Property Office of The People's Republic of China, in related International Application No. PCT/CN2012/000333, with English translation (9 pages).
GenBankAccesion No. BAM18487, version BAM18487.1; "muscle LIM protein [Papilio xuthus]"; Jun. 2, 2012 (Jun. 2, 2012); retrieved from GenBank database www.ncbi.nlm.nih.gov (1 page).
GenBankAccesion No. NP-001037398, version NP-001037398.1; "muscle LIM protein isoform 2 [Bombyx mori]"; Sep. 22, 2013 (Sep. 22, 2013); retrieved from GenBank database www.ncbi.nlm.nih.gov (2 pages).
GenBank Accesion No. XP-003694225, version XP-003694225.1; "PREDICTED: muscle LIM protein Mlp84B-like [Apis florea]"; Mar. 12, 2012 (Mar. 12, 2012); retrieved from GenBank database www.ncbi.nlm.nih.gov (1 page).
GenBankAccesion No. ABD98747, version ABD98747.1; "LIM-like protein [Graphocephala atropunctata]"; Apr. 4, 2006 (Apr. 4, 2006); retrieved from GenBank database www.ncbi.nlm.nih.gov (1 page).
GenBank Accesion No. NP-001153470, version NP-001153470.1; "muscle LIM protein isoform 2 [Nasonia vitripennis]"; Jun. 8, 2014 (Jun. 8, 2014); retrieved from GenBank database www.ncbi.nlm.nih.gov [2 pages].
GenBank Accesion No. EFN69678, version EFN69678.1; "Muscle LIM protein Mlp84B [Camponotus floridanus]"; Sep. 17, 2010 [Sep. 17, 2010]; retrieved from GenBank database www.ncbi.nlm.nih.gov [2 pages].

(Continued)

*Primary Examiner* — Li Zheng
(74) *Attorney, Agent, or Firm* — Osha Liang LLP

(57) ABSTRACT

The present invention relates to pesticide preparations and methods based on RNAi technology. The invention discloses target genes (fragments) useful in the control of Lepidoptera insects. Nucleic acid inhibitors or hosts expressing the nucleic acid inhibitors, based on the nucleic acid sequences of these target genes, can effectively kill Lepidoptera insects. The invention also discloses applications using the nucleic acid inhibitors or hosts expressing the nucleic acid inhibitors.

6 Claims, 2 Drawing Sheets

(56) References Cited

OTHER PUBLICATIONS

GenBank Accesion No. EFN83539, version EFN83539.1; "Muscle LIM protein Mlp84B [Harpegnathos saltator]"; Sep. 17, 2010 [Sep. 17, 2010]; retrieved from GenBank database www.ncbi.nlm.nih.gov [2 pages].
GenBank Accesion No. XP-003491802, version XP-003491802.1; "PREDICTED: muscle LIM protein Mlp84B-like [Bombus impatiens]"; Oct. 7, 2011 [Oct. 7, 2011]; retrieved from GenBank database www.ncbi.nlm.nih.gov [2 pages].
GenBank Accesion No. XP-003702737, version XP-003702737.1; "PREDICTED: muscle LIM protein Mlp84B-like [Megachile rotundata]"; Apr. 10, 2012 [Apr. 10, 2012]; retrieved from GenBank database www.ncbi.nlm.nih.gov [2 pages].
GenBank Accesion No. ADL09420, version ADL09420.1; "myosin light chain 2 [Antheraea pernyi]"; Mar. 14, 2011 [Mar. 14, 2011]; retrieved from GenBank database www.ncbi.nlm.nih.gov [1 page].
GenBank Accesion No. BAM17661, version BAM17661.1; "myosin light chain 2 [Papilio xuthus]"; Jun. 2, 2012 [Jun. 2, 2012]; retrieved from GenBank database www.ncbi.nlm.nih.gov [1 page].
GenBank Accesion No. AAV91413, version AAV91413.1; "myosin 3 light chain [Lonomia obliqua]"; Aug. 15, 2005 [Aug. 15, 2005]; retrieved from GenBank database www.ncbi.nlm.nih.gov [2 pages].
GenBank Accesion No. BAM18881, version BAM18881.1; "myosin light chain 2 [Papilio polytes]"; Jun. 2, 2012 [Jun. 2, 2012]; retrieved from GenBank database www.ncbi.nlm.nih.gov [2 pages].
GenBank Accesion No. NP-001091813, version NP-001091813.1; "myosin regulatory light chain 2 [Bombyx mori]"; Nov. 17, 2013 [Nov. 17, 2013]; retrieved from GenBank database www.ncbi.nlm.nih.gov [2 pages].
GenBank Accesion No. EHJ75770, version EHJ75770.1; "myosin 3 light chain [Danaus plexippus]"; Nov. 21, 2011 [Nov. 21, 2011]; retrieved from GenBank database www.ncbi.nlm.nih.gov [1 page].
GenBank Accesion No. AAW22542, version AAW22542.1; "myosin light chain [Gryllotalpa orientalis]"; Jul. 27, 2005 [Jul. 27, 2005]; retrieved from GenBank database www.ncbi.nlm.nih.gov [1 page].
GenBank Accesion No. AEV23878, version AEV23878.1; "myosin light chain variant 2 [Periplaneta americana]"; Dec. 7, 2011 [Dec. 7, 2011]; retrieved from GenBank database www.ncbi.nlm.nih.gov [1 page].
GenBank Accesion No. ABD47458, version ABD47458.1; "allergen Bla g 8, partial [Blattella germanica]"; Nov. 1, 2006 [Nov. 1, 2006]; retrieved from GenBank database www.ncbi.nlm.nih.gov [1 page].
GenBank Accesion No. AFM77770, version AFM77770.1; "putative chymotrypsin 11 [Ostrinia nubilalis]"; Jun. 27, 2012 [Jun. 27, 2012]; retrieved from GenBank database www.ncbi.nlm.nih.gov [1 page].
GenBank Accesion No. AAX39408, version AAX39408.1; "serine protease [Bombyx mandarina]"; Mar. 20, 2005 [Mar. 20, 2005]; retrieved from GenBank database www.ncbi.nlm.nih.gov [2 pages].
GenBank Accesion No. EHJ77328, version EHJ77328.1; "serine protease precursor [Danaus plexippus]"; Nov. 21, 2011 [Nov. 21, 2011]; retrieved from GenBank database www.ncbi.nlm.nih.gov [1 page].
GenBank Accesion No. AGU27161, version AGU27161.1; "serine protease 13 [Antheraea pernyi]"; Sep. 2, 2013 [Sep. 2, 2013]; retrieved from GenBank database www.ncbi.nlm.nih.gov [1 page].
GenBank Accesion No. ACR15987, version ACR15987.2; "serine protease 13 [Mamestra configurata]"; Mar. 31, 201 [Mar. 31, 2011]; retrieved from GenBank database www.ncbi.nlm.nih.gov [2 pages].
GenBank Accesion No. NP-001036826, version NP-001036826.1; "serine protease precursor [Bombyx mori]"; Aug. 24, 2013 [Aug. 24, 2013]; retrieved from GenBank database www.ncbi.nlm.nih.gov [2 pages].
GenBank Accesion No. AFM77775, version AFM77775.1; "chymotrypsin-like serine protease 16 [Ostrinia nubilalis]"; Jun. 27, 2012 [Jun. 27, 2012]; retrieved from GenBank database www.ncbi.nlm.nih.gov [1 page].
GenBank Accesion No. ACR15983, version ACR15983.2; "serine protease 33 [Mamestra configurata]"; Mar. 31, 2011 [Mar. 31, 2011]; retrieved from GenBank database www.ncbi.nlm.nih.gov [2 pages].
GenBank Accesion No. ACB54938, version ACB54938.1; "trypsin [Helicoverpa armigera]"; Sep. 27, 2008 [Sep. 27, 2008]; retrieved from GenBank database www.ncbi.nlm.nih.gov [1 page].
GenBank Accesion No. ABR88231, version ABR88231.1; "chymotrypsin-like protease C1 [Heliothis virescens]"; Jul. 11, 2008 [Jul. 11, 2008]; retrieved from GenBank database www.ncbi.nlm.nih.gov [1 page].
GenBank Accesion No. AFD99127, version AFD99127.1; "chymotrypsin-like proteinase [Bombyx mori]"; Mar. 24, 2012 [Mar. 24, 2012]; retrieved from GenBank database www.ncbi.nlm.nih.gov [1 page].
GenBank Accesion No. CAM84318, version CAM84318.1; "chymotrypsinogen-like protein 3 [Manduca sexta]"; Sep. 11, 2008 [Sep. 11, 2008]; retrieved from GenBank database www.ncbi.nlm.nih.gov [2 pages].
GenBank Accesion No. EHJ71324, version EHJ71324.1; "chymotrypsin-like protease C1 [Danaus plexippus]"; Nov. 21, 2011 [Nov. 21, 2011]; retrieved from GenBank database www.ncbi.nlm.nih.gov [1 page].
GenBank Accesion No. ACI45417, version ACI45417.1; "chymotrypsin-like serine proteinase C3 [Ostrinia nubilalis]"; Dec. 12, 2008 [Dec. 12, 2008]; retrieved from GenBank database www.ncbi.nlm.nih.gov [2 pages].
GenBank Accesion No. ACR15986, version ACR15986.2; "serine protease 11 [Mamestra configurata]"; Mar. 31, 2011 [Mar. 31, 2011]; retieved from GenBank database www.ncbi.nlm.nih.gov [2 pages].
GenBank Accesion No. AFM28249, version AFM28249.1; "chymotrypsin [Heliothis virescens]"; Dec. 6, 2012 [Dec. 6, 2012]; retrieved from GenBank database www.ncbi.nlm.nih.gov [1 page].
GenBank Accesion No. CAA72952, version CAA72952.1; "chymotrypsin-like protease [Helicoverpa armigera]"; Apr. 18, 2005 [Apr. 18, 2005]; retrieved from GenBank database www.ncbi.nlm.nih.gov [2 pages].
GenBank Accesion No. AAV33653, version AAV33653.1; "chymotrypsinogen [Helicoverpa punctigera]"; Dec. 1, 2006 [Dec. 1, 2006]; retrieved from GenBank database www.ncbi.nlm.nih.gov [1 page].
GenBank Accesion No. AAF43709, version AAF43709.1; "chymotrypsin-like protein precursor [Heliothis virescens]"; Mar. 16, 2000 [Mar. 16, 2000]; retrieved from GenBank database www.ncbi.nlm.nih.gov [2 pages].
GenBank Accesion No. AAA67842, version AAA67842.1; "elastase [Manduca sexta]"; Jun. 2, 1995 [Jun. 2, 1995]; retrieved from GenBank database www.ncbi.nlm.nih.gov (1 page).
GenBank Accesion No. ACU00133, version ACU00133.1; "chymotrypsin-like protein precursor [Spodoptera litura]"; Mar. 31, 2011 [Mar. 31, 2011]; retrieved from GenBank database www.ncbi.nlm.nih.gov [2 pages].
GenBank Accesion No. XP-004931809, version XP-0049318809.1; "PREDICTED: 3-oxoacyl-[acyl-carrier-protein] reductase, chloroplastic-like [Bombyx mori]"; Jun. 18, 2013 [Jun. 18, 2013]; retrieved from GenBank database www.ncbi.nlm.nih.gov [1 page].
GenBank Accesion No. BAM20756, version BAM20756.1; "short-chain dehydrogenase, partial [Papilio polytes]"; Jun. 2, 2012 [Jun. 2, 2012]; retrieved from GenBank database www.ncbi.nlm.nih.gov [1 page].
GenBank Accesion No. EHJ71245, version EHJ71245.1; "3-dehydroecdysone 3alpha-reductase [Danaus plexippus]"; Nov. 21, 2011 [Nov. 21, 2011]; retrieved from GenBank database www.ncbi.nlm.nih.gov [1 page].
GenBank Accesion No. BAM18031, version BAM18031.1; "short chain type dehydrogenase [Papilio xuthus]"; Jun. 2, 2012 [Jun. 2, 2012]; retrieved from GenBank database www.ncbi.nlm.nih.gov [1 page].
GenBank Accesion No. AAF70499, version AAF70499.1; "3-dehydroecdysone 3alpha-reductase [Spodoptera littoralis]"; Jul. 25, 2000 [Jul. 25, 2000]; retrieved from GenBank database www.ncbi.hlm.nih.gov [1 page].

(56) References Cited

OTHER PUBLICATIONS

GenBank Accesion No. XP-004529533, version XP-004529533.1; "PREDICTED: uncharacterized oxidoreductase TM_0325-like [Ceratitis capitata]"; May 14, 2013 [May 14, 2013]; retrieved from GenBank database www.ncbi.nlm.nih.gov [1 page].
GenBank Accesion No. XP-004923541, version XP-004923541.1; "PREDICTED: uncharacterized protein LOC101739721 [Bombyx mori]"; Jun. 18, 2013 [Jun. 18, 2013]; retrieved from GenBank database www.ncbi.nlm.nih.gov [1 page].
GenBank Accesion No. EHJ77331, version EHJ77331.1; "hypothetical protein KGM_05054 [Danaus plexippus]"; Nov. 21, 2011 [Nov. 21, 2011]; retrieved from GenBank database www.ncbi.nlm.nih.gov [1 page].
GenBank Accesion No. ABU98617, version ABU98617.1; "unknown, partial [Helicoverpa armigera]"; Jul. 29, 2008 [Jul. 29, 2008]; retrieved from GenBank database www.ncbi.nlm.nih.gov [1 page].
GenBank Accesion No. ADL38967, version ADL38967.1; "unknown, partial [Spodoptera exigua]"; Dec. 2, 2010 [Dec. 2, 2010]; retrieved from GenBank database www.ncbi.nlm.nih.gov [1 page].
GanBank Accesion No. ADK26057, version ADK26057.1; "Kunitz-type protease inhibitor precursor [Galleria mellonella]"; Dec. 7, 2010 [Dec. 7, 2010]; retrieved from GenBank database www.ncbi.nlm.nih.gov [1 page].
GenBank Accesion No. NP-001037044, version NP-001037044.1; "trypsin inhibitor precursor [Bombyx mori]"; Feb. 22, 2014 [Feb. 22, 2014]; retrieved from GenBank database www.ncbi.nlm.nih.gov [1 page].
GenBank Accesion No. EFN87117, version EFN87117.1; "WAP, kazal, immunoglobulin, kunitz and NTR domain-containing protein 2 [Harpegnathos saltator]"; Sep. 17, 2010 [Sep. 17, 2010]; retrieved from GenBank database www.ncbi.nlm.nih.gov [1 page].
GenBank Accesion No. XP-004531360, version XP-004531360.1; "PREDICTED: protease inhibitor-like [Ceratitis capitata]" May 14, 2013 [May 14, 2013]; retrieved from GenBank database www.ncbi.nlm.nih.gov [1 page].
GenBank Accesion No. XP-003491292, version XP-003491292.1; "PREDICTED: trypsin inhibitor-like [Bombus impatiens]"; Oct. 7, 2011 [Oct. 7, 2011]; retrieved from GenBank database www.ncbi.nlm.nih.gov [1 page].
GenBank Accesion No. XP-003396032, version XP-003396032.1; "PREDICTED: hypothetical protein LOC100631053 [Bombus terrestris]"; Jul. 20, 2011 [Jul. 20, 2011]; retrieved from GenBank database www.ncbi.nlm.nih.gov [1 page].
GenBank Accesion No. XP-005192097, version XP-005192097.1; "PREDICTED: protease inibitor-like [Musca domestica]"; Nov. 12, 2013 [Nov. 12, 2013]; retrieved from GenBank database www.ncbi.nlm.nih.gov [1 page].
GenBank Accesion No. NP-001037574, version NP-001037574.1; "fatty acid binding protein [Bombyx mori]"; Aug. 24, 2013 [Aug. 24, 2013]; retrieved from GenBank database www.ncbi.nlm.nih.gov [1 page].
GenBank Accesion No. ABC02870, version ABC02870.1; "fatty acid binding protein [Helicoverpa assulta]"; Dec. 13, 2005 [Dec. 13, 2005]; retrieved from GenBank database www.ncbi.nlm.nih.gov [1 page].
GenBank Accesion No. EHJ79282, version EHJ79282.1; "Fatty acid-binding protein 2 [Danaus plexippus]"; Nov. 21, 2011 [Nov. 21, 2011]; retrieved from GenBank database www.ncbi.nlm.nih.gov [1 page].
GenBank Accesion No. AAC25674, version AAC25674.1; "fatty acid binding protein [Helicoverpa zea]"; Jul. 7, 1998 [Jul. 7, 1998]; retrieved from GenBank database www.ncbi.nlm.nih.gov [1 page].
GenBank Accesion No. ACB54949, version ACB54949.1; "fatty acid-binding protein 2 [Helicoverpa armigera]"; Sep. 27, 2008 [Sep. 27, 2008]; retrieved from GenBank database www.ncbi.nlm.nih.gov [1 page].

GenBank Accesion No. EHJ79280, version EHJ79280.1; "Fatty acid-binding protein 2 [Danaus plexippus]"; Nov. 21, 2011 [Nov. 21, 2011]; retrieved from GenBank database www.ncbi.nlm.nih.gov [1 page].
GenBank Accesion No. AEH16743, version AEH16743.1, "fatty acid binding protein [Spodoptera litura]"; Jun. 12, 2011 [Jun. 12, 2011]; retrieved from GenBank database www.ncbi.nlm.nih.gov [1 page].
GenBank Accesion No. ACN69214, version ACN69214.1, "caboxypeptidase 4 [Mamestra configurata]"; Mar. 31, 2011 [Mar. 31, 2011]; retrieved from GenBank database www.ncbi.nlm.nih.gov [2 pages].
GenBank Accesion No. CAJ30028, version CAJ30028.1; "carboxypeptidase B precursor [Helicoverpa zea]" Nov. 25, 2009 [Nov. 25, 2009]; retrieved from GenBank database www.ncbi.nlm.nih.gov [2 pages].
GenBank Accesion No. XP-004922814, version XP-004922814.1; "Predicted: carboxpeptidase B-like [Bombyx mori]"; Jun. 18, 2013 [Jun. 18, 2013]; retrieved from GenBank database www.ncbi.nlm.nih.gov [2 pages].
GenBank Accesion No. ABU98625, version ABU98625.1; "carboxypeptidase [Helicoverpa armigera]"; Jul. 29, 2008 [Jul. 29, 2008]; retrieved from GenBank database www.ncbi.nlm.nih.gov [1 page].
GenBank Accesion No. EHJ75109, version EHJ75109.1; "carboxypeptidase B precursor [Danaus plexippus]"; Nov. 21, 2011 [Nov. 21, 2011]; retrieved from GenBank database www.ncbi.nlm.nih.gov [1 page].
GenBank Accesion No. AAS82587, version AAS82587.1, "midgut carboxypeptidase 2, partial [Trichoplusia ni]"; Jul. 26, 2004 [Jul. 26, 2004]; retrieved from GenBank database www.ncbi.nlm.nih.gov [1 page].
Extended European Search Report dated Mar. 31, 2015, issued by the European Patent Office in corresponding European Patent Application No. EP-12760973.3 (15 pages).
Hwang, Jae-Sam, et al., "cDNA cloning and mRNA expression of LIM protein gene homologue from the silkworm, Bombyx mori"; Biotechnology Letters, vol. 26, No. 19, Oct. 1, 2004; XP002732588, ISSN: 0141-5491; pp. 1469-1473.
Lim protein; Database accession No. Q6SA71; Oct. 31, 2006; retrieved from http://www.ncbi.nlm.nih.gov (1 page).
Veiga, Ana B.G., et al., "A catalog for the transcripts from the venomous structures of the caterpillar Lonomia obliqua: Identification of the proteins potentially involved in the coagulation disorder and hemorrhagic syndrome"; GENE, Section Evolutionary Genomics, Elsevier, vol. 355, Aug. 1, 2005, XP027872200, ISSN: 0378-1119; pp. 11-27.
LIM protein 1, Database accession No. Q5MGJ0; Oct. 31, 2006; retrieved from http//www.ncbi.nlm.nih.gov (1 page).
Arber, Silvia, et al., "Muscle LIM Protein, a Novel Essential Regulator of Myogenesis, Promotes Myogenic Differentiation"; CELL, vol. 79, No. 2, Oct. 21, 1994; XP024244971, ISSN: 0092-8674, DOI: 10.1016/0092-8674 (94)90192-9; pp. 221-131.
Stronach, Beth E., et al., "Two Muscle-specific LIM Proteins in Drosophila"; Journal of Cell Biology, vol. 134, No. 5, Sep. 1, 1996; XP002732589, ISSN: 0021-9525; pp. 1179-1195.
Mery, Annabelle, et al., "The Drosophilia muscle LIM protein, Mlp84B, is essential for cardiac function"; Journal of Experimental Biology, vol. 211, No. 1, Jan. 2008; XP002732590, ISSN: 0022-0949; pp. 15-23.
Wang, Yubing, et al., "Second-Generation Sequencing Supply an Effective Way to Screen RNAi Targets in Large Scale for Potential Application in Pest Insect Control"; PLOS ONE, vol. 6, Issue No. 4, Apr. 11, 2011; XP055153394, DOI: 10.1371/journal.pone.0018644; e18644; pp. 1-10.
EPO Communication pursuant to Article 94(3) EPC (Office Action) dated Aug. 17, 2016, issued by the European Patent Office in related European Application No. 12760973.3 (5 pages).
EPO Communication pursuant to Article 94(3) EPC (Office Action) dated Jan. 23, 2017, issued by the European Patent Office (EPO) in related European Patent Application No. 12760973.3 (4 pages).

(56) References Cited

OTHER PUBLICATIONS

European Office Action issued Mar. 8, 2016, in corresponding European Patent Application No. 12760973.3 (5 pages).

* cited by examiner

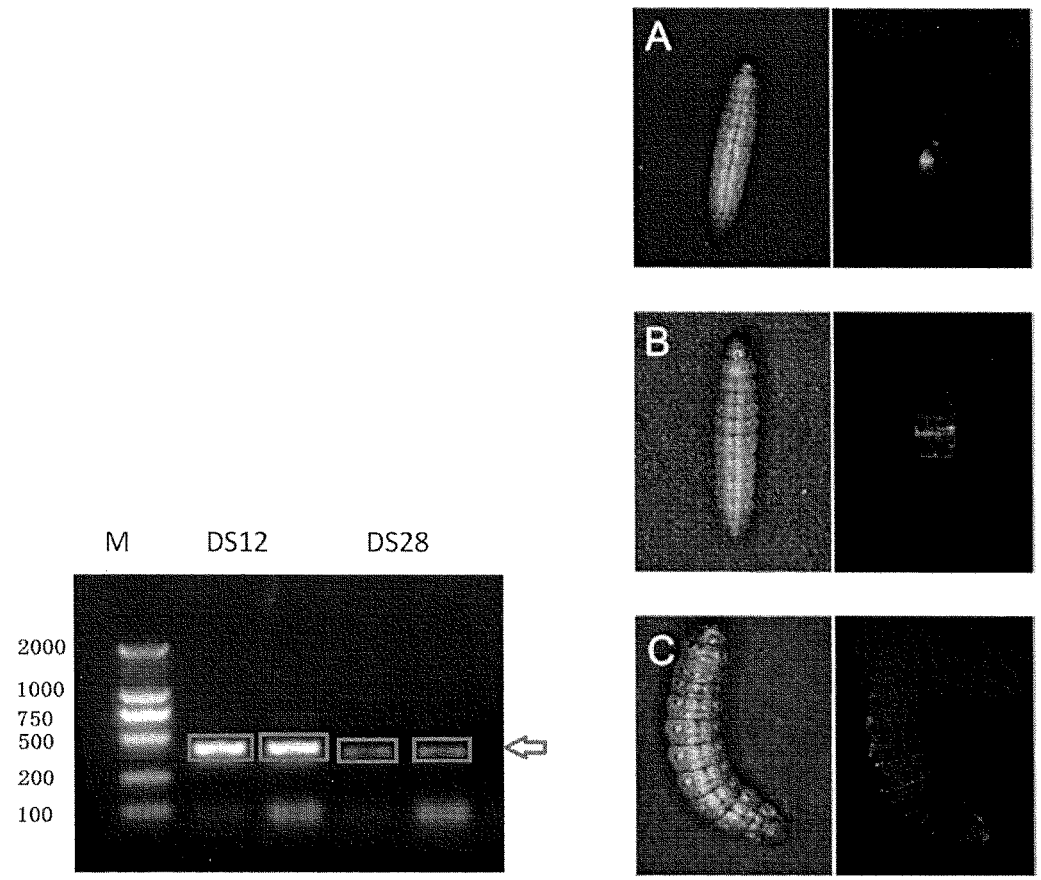
FIG. 4
FIG. 5
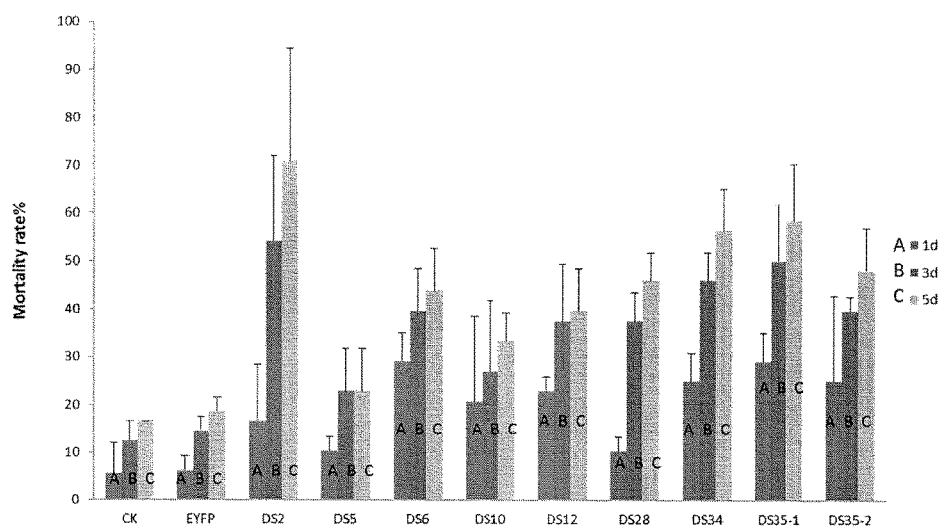
FIG. 6

SEQUENCE LISTING

<160> NUMBER OF SEQ ID NOS: 117

<210> SEQ ID NO 1
<211> LENGTH: 433
<212> TYPE: DNA
<213> ORGANISM: Ostrinia furnacalis Guenee

<400> SEQUENCE: 1

```
tatcttcgcc ctgtactgta atacgcgttc gggagctcga ctctcgtagc gactcgacga      60
acaggataag ttaagcgagc acaatgcctt tcaaaccagc agacaacccc aagtgtccga     120
aatgcggcaa gtccgtatac gcagccgagg agagagtagc cggtggactg aagtggcaca     180
agatgtgctt caagtgcgga ctgtgccaga agttgctgga ctccaccaac tgctcagaac     240
acgaaggtga actgttctgc aaagtatgcc acgcgcgcaa gttcggtccc aagggctacg     300
gcttcggcgg tggcgctggc tgcctttcca tggacgctgg tgaacacctg aaggctgaag     360
atgcgaattg agcgcgagca gccatccagc agagctagcg ggtcgctctc cctatagtgg     420
gttcgtaaat aaa                                                        433
```

<210> SEQ ID NO 2
<211> LENGTH: 491
<212> TYPE: DNA
<213> ORGANISM: Ostrinia furnacalis Guenee

<400> SEQUENCE: 2

```
ccatccatgt tctcacagaa gcaggtcgcc gaattcaagg aggccttcca gctaatggac      60
cacgacaagg acggtatcat cggcaagaac gacctccgcg ccaccttcga ctcgctcggc     120
aggctggcgt ccgagaagga gctggacgag atggtgaacg aggcccccgg ccccatcaac     180
ttcacgcagc tgctgaccct cttcgccaac cgcatgtccg cgggctccga cgaggacgac     240
gtcgtcatca acgccttcaa gaccttcgac gaggagggca agatcgactc cgagaggctc     300
aggcacgcgc tcatgacctg gggagacaag ttctccgccg acgaggtcga cgaggcctac     360
gaccagatgg aaatcgacga caagggcttc atcgacacca ccaagctcat caccatgctg     420
accgccgccg ctgaggagga cgagggcggc gaagctgcgt agttccaccc cgcgccagtct    480
ccctatagta g                                                         491
```

<210> SEQ ID NO 3
<211> LENGTH: 415
<212> TYPE: DNA
<213> ORGANISM: Ostrinia furnacalis Guenee

<400> SEQUENCE: 3

```
tgcggcagtt cgctggtcag caacacgcgc tcggtgacgg cggctcactg ctggcgcacc      60
agcaccttgc aggcgaccat gttcaccatc gtgtggaact ctaactctat attctggggc     120
ggcacgcgca taaacaccaa ccaggtcata gagcacccga attacaacgt gtggaacttg     180
aacaacgatg tggccgtcat catacacaac cacgtaaatt tcaacaataa tatccagcca     240
attgccctgg ccactggctc gcaaacctac gcgggaaccct gggcagtcgc tgctggatac     300
ggccagactg gcgatggtaa ttcaccgtct ggcactaagt tccaagccaa tctgctggtg     360
atcaccaact cagcgtgcca gggaacctgg atgcccggca tcgtcatcgc gtcca          415
```

<210> SEQ ID NO 4
<211> LENGTH: 359
<212> TYPE: DNA
<213> ORGANISM: Ostrinia furnacalis Guenee

<400> SEQUENCE: 4

```
gtcagagtca gggctggcgg tcccatctcc gctcagctcc tcgagttgac cgtgaccacc      60
atctctggcg atcagtgcgt gcgcgacgtg gcccaggcct ccgtcgactt caacgtcgcc     120
gccccaccgg tggaaccccca cgtcgagctc tgcatcatcc actcgccgaa ccacggcatg     180
```

```
tgcaacggtg actccggcag cgctctagtc cgcctggacc gcggcaccca gatcggaatc    240
gtgtcgtggg gcttcccctg cgcccgcggc gctcccgata tgttcgtccg agtcagcgcc    300
ttccaagact gggtcgcccg ccacttcgtt gcttgtctcc ctatagtgag tcgtattaa     359
```

<210> SEQ ID NO 5
<211> LENGTH: 494
<212> TYPE: DNA
<213> ORGANISM: Ostrinia furnacalis Guenee

<400> SEQUENCE: 5

```
accgggtcgt gctcggctcc acactatctt cagcggtggt gtccgtcaaa ccacctctga     60
cattgtcatg cacccacagt ggaccccgga gaccgttgct aatgacattg ccgtcattag    120
gattaacgct gttactttca ccaatgtgat ccagcccatc tctctgccca gcggatctca    180
gctaaataac aacttcgtag gccaggtcgg aattgcttct ggattcggac gcacttctga    240
tggtgctaac atcccgaaca accaactcgt gagctgggtg agagtgccga tcatcaccaa    300
ccaggcgtgc gcctcagtct tcggaccctt catcttaagt agcaccatct gcaccaacgg    360
ctctggtggt atgggcacgt gccagggaga ctctggtggt cctctcgctg tggaagttgg    420
caactctagg gtcttggttg gtgtgacttc ctttggtgct gctgccggtc tccctatagt    480
gagtccgtaa taaa                                                      494
```

<210> SEQ ID NO 6
<211> LENGTH: 491
<212> TYPE: DNA
<213> ORGANISM: Ostrinia furnacalis Guenee

<400> SEQUENCE: 6

```
ttgccatcgt tggagaacgc agccaaacta aaagatgtta cggaaagtat ctcgaaggtc     60
ggtaacaagc tcttgtgat caccgccgat gttaccaaag aaagtgatgc tcaaagaatc    120
atcaacgata cagtaaaaca tttttggaaaa cttgacattc ttgtcaacaa tgcaggagtg    180
ggtggcaatg ccagcattac tgaagcagaa gccatgacaa catttgacca tatcatgaat    240
accaacctgc gttccgctgt ctacatgacc aatctggctg ccaagcatct tattgaaacg    300
aaagggaatg taataaacat atcaagcgtt gctggtcaaa tggtgatgga aaaagggttt    360
gcttactgca cctcaaaagc tgccttggat catttcgcga atcaatcac gttgactttt    420 gcgccacatg tgttcgcgt gaacaacatt agccctgggc cggtgaggtc tccctatagt    480
agtcgtatta a                                                         491
```

<210> SEQ ID NO 7
<211> LENGTH: 433
<212> TYPE: DNA
<213> ORGANISM: Ostrinia furnacalis Guenee

<400> SEQUENCE: 7

```
aagaaccatg ccgatcagct gatcagtgcc cacgtccagc agtgggaacc acggcaggag     60
ggtgtcagac ctgcactcgg tggcggttgt catgttgtag tagtagtggc gacccatgag    120
aataatgcaa gcttgtttgg tgaaatgggt ggtggcggtg tcggtgacct cgttggcgtt    180
gccggagatc ctcatcaggt ctccgttgaa gccggtgacc cacacagcat tctcctgcag    240
tacgcggcct gccacgcggg aggcgcggcg ctcctccttg ctcttcttca atgtggcttc    300
agaaacgaag tattgctgca aggtccagta attcctaact tgtccattag agtttgccgg    360
```

```
tgcagtccag tacgtgtagc cttgggtagc ccagtccaag acagcgccgt ctccctatag    420
tgagtcgtat taa                                                      433

<210> SEQ ID NO 8
<211> LENGTH: 495
<212> TYPE: DNA
<213> ORGANISM: Ostrinia furnacalis Guenee

<400> SEQUENCE: 8
ccgcgcagcg tcgccccgcg tcctacttta ctaaacttgg aaggtgcaaa cagttcatct     60
acggaggatg tgacggcaac ggcaaccgtt acaacactct agaggagtgt caggctgctt    120
gcgagagtga ctgcaacaaa taataacgaa atgcaagcaa tcaattgggt atttgacagc    180
acagtcaatt gacatacttt ttttatactg tcaaaacgca ccattcccta tttttcacat    240
tttgcaaagt agagggaatc taaaggccat agcagactta tcaactcgga aagggatcat    300
accgtatcgc cgttcgcgag ctatcatcgc ctttcgcgcg ctgtcaactg tcaaccgcga    360
ggcgaggcgt ttacgttact gtgcggataa gtgtgggtta cagtatggaa tttcacactg    420
atcgcatcaa tttaatacgg ttacaatccc tgtccgggtt gaaaagtggg ccctcccaat    480
agggagccga ataaa                                                    495

<210> SEQ ID NO 9
<211> LENGTH: 320
<212> TYPE: DNA
<213> ORGANISM: Ostrinia furnacalis Guenee

<400> SEQUENCE: 9
gggccttcat gcagtacaag ccgaaccaga tcctcgagaa gaacggggac tcctacaagc     60
tgatcttcaa gacccccgcc ctgaaccacg aggtggtgtt caagtctgga gtgccttaca    120
gcgacgtcat ccgtgaaggt ttgacggctg aatccaccat caccgtcgat ggagacacct    180
tcactcaggt ccaggactac ggccccttg gctccatcac cttcaagaga gagtacagcg     240
ccgaccaact taaagtgact gtcaccagca gtaaatggga tggcgttgcc tacagatctc    300
cctatagtga gtcgtattaa                                               320

<210> SEQ ID NO 10
<211> LENGTH: 568
<212> TYPE: DNA
<213> ORGANISM: Ostrinia furnacalis Guenee

<400> SEQUENCE: 10
aaagggcccc gccccatcaa gtacctgaag atatccacca ccaacttcca agacaccagc     60
aagcctgtca tcttcattga cggaggcatc cactccaggg aatggatctc accacccacc    120
gtcacttggg cgatcaggaa actggtggaa gatgtcaccg aacctgacct cctggagagg    180
ttcgactgga tactcttgcc tatcgtcaac cctgacggtt atgaacacag ccacacatct    240
aaccgtttct ggaggaagac acgttcggct accagcattg cattatgccg aggagttgat    300
ggcaaccgca actacgactt cgcatggaac accgtcggaa ccagcaccaa cccttgctcc    360
gacacttatg gaggccctac agccttctcc gaaatcgaga ccagggttgt tcgtgacatc    420
ctccacgaga acctcagcag aatggctctg tacctcacca tgcatagctt tggtagcatg    480
atcctgtacc cttggggaca tgatggttct ttatccaaca acgcatttgc actccagacc    540
gttctcccta tagtgagtcg tattaaaa                                      568
```

```
<210> SEQ ID NO 11
<211> LENGTH: 40
<212> TYPE: DNA
<213> ORGANISM: Artificial Sequence
<220> FEATURE:
<223> OTHER INFORMATION: Syntheitc

<400> SEQUENCE: 11
taatacgact cactataggg aggacgacgg caactacaag                    40

<210> SEQ ID NO 12
<211> LENGTH: 40
<212> TYPE: DNA
<213> ORGANISM: Artificial Sequence
<220> FEATURE:
<223> OTHER INFORMATION: Synthetic

<400> SEQUENCE: 12
taatacgact cactataggg gaactccagc aggaccatgt                    40

<210> SEQ ID NO 13
<211> LENGTH: 42
<212> TYPE: DNA
<213> ORGANISM: Artificial Sequence
<220> FEATURE:
<223> OTHER INFORMATION: Synthetic

<400> SEQUENCE: 13
taatacgact cactataggg agagcacgag ggcagtctcg gc                 42

<210> SEQ ID NO 14
<211> LENGTH: 43
<212> TYPE: DNA
<213> ORGANISM: Artificial Sequence
<220> FEATURE:
<223> OTHER INFORMATION: Synthetic

<400> SEQUENCE: 14
taatacgact cactataggg agagcgaccc gctagctctg ctg                43

<210> SEQ ID NO 15
<211> LENGTH: 43
<212> TYPE: DNA
<213> ORGANISM: Artificial Sequence
<220> FEATURE:
<223> OTHER INFORMATION: Synthetic

<400> SEQUENCE: 15
taatacgact cactataggg agacgcaccg gctccaacgt ctt                43

<210> SEQ ID NO 16
<211> LENGTH: 43
<212> TYPE: DNA
<213> ORGANISM: Artificial Sequence
<220> FEATURE:
<223> OTHER INFORMATION: Synthetic

<400> SEQUENCE: 16
taatacgact cactataggg agactggcgc gggtggaact acg                43

<210> SEQ ID NO 17
<211> LENGTH: 43
<212> TYPE: DNA
<213> ORGANISM: Artificial Sequence
<220> FEATURE:
<223> OTHER INFORMATION: Synthetic
```

<400> SEQUENCE: 17
taatacgact cactataggg agactgcggc agttcgctgg tca                43

<210> SEQ ID NO 18
<211> LENGTH: 43
<212> TYPE: DNA
<213> ORGANISM: Artificial Sequence
<220> FEATURE:
<223> OTHER INFORMATION: Synthetic

<400> SEQUENCE: 18
taatacgact cactataggg agatggacgc gatgacgatg ccg                43

<210> SEQ ID NO 19
<211> LENGTH: 43
<212> TYPE: DNA
<213> ORGANISM: Artificial Sequence
<220> FEATURE:
<223> OTHER INFORMATION: Synthetic

<400> SEQUENCE: 19
taatacgact cactataggg agagtccaga gccgctggtt ggg                43

<210> SEQ ID NO 20
<211> LENGTH: 43
<212> TYPE: DNA
<213> ORGANISM: Artificial Sequence
<220> FEATURE:
<223> OTHER INFORMATION: Synthetic

<400> SEQUENCE: 20
taatacgact cactataggg agacaagcaa cgaagtggcg ggc                43

<210> SEQ ID NO 21
<211> LENGTH: 43
<212> TYPE: DNA
<213> ORGANISM: Artificial Sequence
<220> FEATURE:
<223> OTHER INFORMATION: Synthetic

<400> SEQUENCE: 21
taatacgact cactataggg agagcgtcac cgctcagtcc cac                43

<210> SEQ ID NO 22
<211> LENGTH: 43
<212> TYPE: DNA
<213> ORGANISM: Artificial Sequence
<220> FEATURE:
<223> OTHER INFORMATION: Synthetic

<400> SEQUENCE: 22
taatacgact cactataggg agaccggcag cagcaccaaa gga                43

<210> SEQ ID NO 23
<211> LENGTH: 43
<212> TYPE: DNA
<213> ORGANISM: Artificial Sequence
<220> FEATURE:
<223> OTHER INFORMATION: Synthetic

<400> SEQUENCE: 23
taatacgact cactataggg agacgctgga gagggagcga acg                43

<210> SEQ ID NO 24
<211> LENGTH: 43

<210> SEQ ID NO 24
<211> LENGTH: 43
<212> TYPE: DNA
<213> ORGANISM: Artificial Sequence
<220> FEATURE:
<223> OTHER INFORMATION: Synthetic

<400> SEQUENCE: 24
taatacgact cactataggg agacctcacc ggcccagggc taa        43

<210> SEQ ID NO 25
<211> LENGTH: 43
<212> TYPE: DNA
<213> ORGANISM: Artificial Sequence
<220> FEATURE:
<223> OTHER INFORMATION: Synthetic

<400> SEQUENCE: 25
taatacgact cactataggg agagcagctg gccaaacgac gtg        43

<210> SEQ ID NO 26
<211> LENGTH: 43
<212> TYPE: DNA
<213> ORGANISM: Artificial Sequence
<220> FEATURE:
<223> OTHER INFORMATION: Synthetic

<400> SEQUENCE: 26
taatacgact cactataggg agacggcgct gtcttggact ggg        43

<210> SEQ ID NO 27
<211> LENGTH: 43
<212> TYPE: DNA
<213> ORGANISM: Artificial Sequence
<220> FEATURE:
<223> OTHER INFORMATION: Synthetic

<400> SEQUENCE: 27
taatacgact cactataggg agagaccgga ccatgcagag gcg        43

<210> SEQ ID NO 28
<211> LENGTH: 47
<212> TYPE: DNA
<213> ORGANISM: Artificial Sequence
<220> FEATURE:
<223> OTHER INFORMATION: Synthetic

<400> SEQUENCE: 28
taatacgact cactataggg agagcacact tatcaacacg gacaggg    47

<210> SEQ ID NO 29
<211> LENGTH: 44
<212> TYPE: DNA
<213> ORGANISM: Artificial Sequence
<220> FEATURE:
<223> OTHER INFORMATION: Synthetic

<400> SEQUENCE: 29
taatacgact cactataggg agagcctttg acgccaacgc caag       44

<210> SEQ ID NO 30
<211> LENGTH: 44
<212> TYPE: DNA
<213> ORGANISM: Artificial Sequence
<220> FEATURE:
<223> OTHER INFORMATION: Synthetic

<400> SEQUENCE: 30

```
taatacgact cactataggg agatctgtag gcaacgccat ccca                    44
```

<210> SEQ ID NO 31
<211> LENGTH: 43
<212> TYPE: DNA
<213> ORGANISM: Artificial Sequence
<220> FEATURE:
<223> OTHER INFORMATION: Synthetic

<400> SEQUENCE: 31

```
taatacgact cactataggg agacagcccc gccaactcct tcg                     43
```

<210> SEQ ID NO 32
<211> LENGTH: 23
<212> TYPE: DNA
<213> ORGANISM: Artificial Sequence
<220> FEATURE:
<223> OTHER INFORMATION: Synthetic

<400> SEQUENCE: 32

```
aacggtctgg agtgcaaatg cgt                                           23
```

<210> SEQ ID NO 33
<211> LENGTH: 612
<212> TYPE: DNA
<213> ORGANISM: Ostrinia furnacalis Guenee

<400> SEQUENCE: 33

```
ggattcgacc tccgcgcacc gcagtctcgg catcttcgcc ctgtactgta atacgcgttc    60
gggagctcga ctctcgtagc gactcgacga acaggataag ttaagcgagc acaatgcctt   120
tcaaaccagc agacaacccc aagtgtccga atgcggcaa gtccgtatac gcagccgagg   180
agagagtagc cggtggactg aagtggcaca agatgtgctt caagtgcgga ctgtgccaga   240
agttgctgga ctccaccaac tgctcagaac acgaaggtga actgttctgc aaagtatgcc   300
acgcgcgcaa gttcggtccc aagggctacg gcttcggcgg tggcgctggc tgcctttcca   360
tggacgctgg tgaacacctg aaggctgaag atgcgaattg agcgcgagca gccatccagc   420
agagctagcg ggtcgccgac acacatctcg gccaaccagc ggtgcctcgc gaacgcacgc   480
catactgtac tttaattact ttagttaggg ttatttattc gctattgctt aatttatttt   540
gtttatcgga acaatattta aatttatac aaaatccaat aaaagagtcg actaccaaca   600
aaaaaaaaaa aa                                                      612
```

<210> SEQ ID NO 34
<211> LENGTH: 819
<212> TYPE: DNA
<213> ORGANISM: Ostrinia furnacalis Guenee

<400> SEQUENCE: 34

```
gggactgccg tcgagcacag tctctccttc gtcgatcgtc caacacacaa cacaatggcg    60
gataaggata agaaagtaaa gaagaagaag gcgaaagaag atgcgccagc tgaggaggcg   120
cccgcaccag cggcgcccgc agccagcggc ggcagcgaga ggcaatcctc ccgcggcagc   180
cgcaaggcca agcgcaccgg ctccaacgtc ttctccatgt tctcacagaa gcaggtcgcc   240
gaattcaagg aggccttcca gctaatggac cacgacaagg acggcatcat cggcaagaac   300
gacctccgcg ccaccttcga ctcgctcggc aggctggcgt ccgagaagga gctggacgag   360
atggtgaacg aggcccccgg cccgatcaac ttcacgcagc tgctgaccct cttcgccaac   420
cgcatgtccg gcggctccga cgaggacgac gtcgtcatca acgccttcaa gaccttcgac   480
```

```
gaggagggca agatcgactc cgagaggctc aggcacgcgc tcatgacctg gggagacaag      540
ttctccgccg acgaggtcga cgaggcgtac gaccagatgg aaatcgacga caagggcttc      600
atcgacacca ccaagctcat caccatgctg accgccgccg cggaggagga cgagggcggc      660
gaagctgcgt agttccaccc gcgccagtct ccgcccgacc cgcggttcgc aacatctaga      720
accgactttt tattataatt tctatatgta atttattgtt tccatttttt tatttatata      780
taatgaaaat atagttctac tattaccaaa aaaaaaaa                              819
```

<210> SEQ ID NO 35
<211> LENGTH: 938
<212> TYPE: DNA
<213> ORGANISM: Ostrinia furnacalis Guenee

<400> SEQUENCE: 35

```
gcacgagggc cgtccaatga agtcaatgaa gtcaatgaag tcgtccctct tgttcctgtt       60
ggtggtggcg gtggcggcgg cggagctgct cagcccaac acgcgctacc acgagaccga      120
gggcatcccg aagttccagc tgatgaagca gctggaggag ggaaccgact tcgatggcgg      180
caggatctgg ggcgggcagg ccgtcagcgg cggtacccat cctcacctgg aggactgtg      240 gatcaccctg accactggac agaactcgat ctgcggcagt tcgctggtca gcaacacgcg      300
ctcggtgacg gcggctcact gctggcgcac cagcaccttg caggcgacca tgttcaccat      360
cgtgtggaac tctaactcta tattctgggg cggcacgcgc ataaacacca accaggtcat      420
agagcacccg aattacaacg tgtggaactt gaacaacgat gtggccgtca tcatacacaa      480
ccacgtaaat ttcaacaata atatccagcc aattgccctg ccactggct cgcaaaccta      540 cgcgggaacc tgggcagtcg ctgctggata cggccagact ggcgatggta attcaccgtc      600
tggcactaag ttccaagcca atctgctggt gatcaccaac tcagcgtgcc agggaacctg      660
gatgcccggc atcgtcatcg cgtccacgct gtgcgtgagc accgcgcacg gcagcagcac      720
ctgccccggc gactccggcg gcccgcttgc cgtcggctcc ggcaacaaca ggcaactgat      780
cggtattact tcttttggaa ctcagtggtg cgctcaacac caccctgctg gattcgctcg      840
agtcacctcg tttgcgtcat ggtttaacag ccatatgtaa aaaaactaca acgtataaat      900
aaaagtataa gtcttgtacc aaataaatct ttcactat                             938
```

<210> SEQ ID NO 36
<211> LENGTH: 913
<212> TYPE: DNA
<213> ORGANISM: Ostrinia furnacalis Guenee

<400> SEQUENCE: 36

```
gggcaaaaaa aatccttctc gggcttccaa aatggcagta aaaaccggaa tactttctt       60 caccctgctc gtgggatgtc tagctatccc caagcccgcg tcggatgacc tgtcccagtt      120
cttcgagcat gccaacccag attcccgcat cgtcggcggg acgtggcag ccatcggcgc      180 ccaccctcac atggtggcca tgagcaacgg tctcctgatc aggagcttcg tttgcggtgg      240
ctctctcatc tcctcccgta ctgttctgac cgctgcccac tgcatcgctg ctgtcttcag      300
cttcggctct ctgagcagct ccctccgcgt gaccgtcggc accaacaact ggaaccaggg      360
tggagtggcc tacgccctgg cccgcaacgt gactcacgag cactacgtca gccagatcat      420
caagaacgac atcggagtgc tgatcaccte ctcgcctgtg gtgttcacca atctcgtcca      480
gcccatcact gtgtcttatg attacgccgg tgctggaatc cagtccagag ccgctggttg      540
```

| | |
|---|---|
| gggcagaatc agggccggcg gtcccatctc cgctcagctc ctcgagttga ccgtgaccac | 600 |
| catctccggc gatcagtgcg tgcgtggcgt ggcccaggcc tccgtcgact tcaacgtcgc | 660 |
| cgccccaccg gtggaacccc acatcgaact ctgcatcatc cactcgccga accacggcat | 720 |
| gtgcaacggt gactccggca gcgctctagt ccgcctggac cgcggcaccc agatcggaat | 780 |
| cgtgtcatgg ggcttcccct cgcccgcgg cgctcccgat atgttcgtcc gagtcagcgc | 840 |
| tttccaagac tgggtcgccc gccacttcgt tgcttgaata aatgacttga tatgatcgtg | 900 |
| caaaaaaaaa aaa | 913 |

<210> SEQ ID NO 37
<211> LENGTH: 967
<212> TYPE: DNA
<213> ORGANISM: Ostrinia furnacalis Guenee

<400> SEQUENCE: 37

| | |
|---|---|
| gggagcgttc attaacacta caacatgaa ggtacttctt gggtcagtgg ttctggtctt | 60 |
| ggccatcgcg gcttcttatg ctgaggggcc agttaactac catcagagga ttggcattcc | 120 |
| tgaggcagct aagatcagaa ggactgagga agatgcggcc aaggctggtg tcgatctcag | 180 |
| aatcgttggt ggatccaatg ttgacatctc ccaagtacct taccaagttg gtctagtcat | 240 |
| ccaaatcctg tggatcctga cttctgtgtg cggaggcagc ttgatctcaa cacccgtgt | 300 |
| gatcaccgct gcgcactgcc accatgacgg tagcgtcacc gctcagtccc acccgtcgt | 360 |
| gctcggctcc aacactatct tcagcggtgg tgtccgtcaa accacctctg acattgtcat | 420 |
| gcacccacag tggaccccgg agaccgttgc taatgacatt gccgtcatta ggattaacgc | 480 |
| tgttactttc accaatgtga tccagcccat ctctctgccc agcggatctc agctaaataa | 540 |
| caacttcgta ggccaggtcg gaattgcttc tggattcgga cgcacttctg atggtgctaa | 600 |
| catcccgaac aaccaactcg tgagctgggt gagagtgccg atcatcacca accaggcgtg | 660 |
| cgcctcagtc ttcggaccct tcatcttaag tagcaccatc tgcaccaacg gctctggtgg | 720 |
| tatgggcacg tgccagggag actctggtgg tcctctcgct gtggaagttg gcaactctag | 780 |
| ggtcttggtc ggtgtgactt cctttggtgc tgctgccggt tgccaagctg gattacctgc | 840 |
| ggcgtacgct cgcgtcacct cattcatctc ttggatcttg gccatataag taaaatgatc | 900 |
| taacgaaccc tacctgatct gtaacgtgtg attgttatta ataatttaa aaaataaaaa | 960 |
| aaaaaaa | 967 |

<210> SEQ ID NO 38
<211> LENGTH: 850
<212> TYPE: DNA
<213> ORGANISM: Ostrinia furnacalis Guenee

<400> SEQUENCE: 38

| | |
|---|---|
| ggaaataatt gtcataagca agatgagttt caacaataaa gtagcgttag tgactggtgc | 60 |
| gagctctggg atcggagcag ctattgctct taaattcgct ggagagggag cgaacgttgc | 120 |
| catcgttgga agaaacgcag ctaaactaaa agatgttacg gaaagtatct cgaaggtcgg | 180 |
| taacaagcct cttgtgatca ccgccgatgt taccaaagaa agtgatgctc aaagaatcat | 240 |
| caacgataca gtaaaacatt ttggaaaact tgacattctt gtcaacaatg caggagtgat | 300 |
| tcgctatgcc agcattactg aagcagaagc catggcagca tttgaccata tcatgagtac | 360 |
| caacctgcgt tccgctgtct acatgaccaa tctggctgcc aagcatctta ttgaaacgaa | 420 |
| agggaatata ataaacatat caagcgttac tggtcaaatg gtgatggaaa aatcgtttgc | 480 |

```
ttactgcaca tcaaaagctg ccatggatca tttcgcgaga gcaatcgcgt tggactttgc    540
gccacatggt gttcgcgtga acaacattag ccctgggccg gtgaggaccg atatcgttga    600
aaatatggga gtcagtgcgg agattcaagc agcagtatgg gaaacattca aagcagcaac    660
tcctttgaaa agaattagtg aaccaagtga gattgccgag ctagcggcgt tcttggctag    720
tgacaaagct gttggtatca ctggatcaat ttacgtaact gataatggag ttttgctatc    780
acgttcaaag taattcactt agacaaaaat atcattaat  atacttaagg taacttctga    840
aaaaaaaaaa                                                            850
```

<210> SEQ ID NO 39
<211> LENGTH: 1008
<212> TYPE: DNA
<213> ORGANISM: Ostrinia furnacalis Guenee

<400> SEQUENCE: 39

```
ggggttcttg aagaaaccat gaccatggac aaactgattg tgttagccgc ctgcattgcc     60
gcagccagcg cacttggatc ctggaaaagt ggattgagcg tgcgttttgg ggttggcctc    120
ttcggatggg gttcttccta cttcattcat gtcccccaga ctgtggctga tgccaagaac    180
tcccgctggt tggaaacccc aagacccgat ggccccctga gcagtttgat tatgatgtgt    240
ccttcccaga cgatgtggt  cctctgtgcc ctctatgatg acaatggtga tgtggctggt    300
ctccagattg ctctgcccac tgatagttac accggcgctg tcttggactg gctacccaa    360
ggctacacgt actggactgc accggcaaac tctaatggac aagttaggaa ttactggacc    420
ttgcagcaat acttcgtttc tgaagccaca ttgaagaaga gcaaggagga gcgccgcgcc    480
tcccgcgtgg caggccgcgt actgcaggag aatgctgtgt gggtcaccgg cttcaacgga    540
gacctgatga ggatctccgg caacgccaac gaggtcaccg acaccgccac cacccacttc    600
accaaacaag cttgcattat tctcatgggt cgccactact actacaacat gacaaccgcc    660
accgagtgca ggtctgacac cctcctgccg tggttcccac tgctggacgt gggcactgat    720
cagctgatcg gcatgggttt cacgtcgttt ggccagctgc ccgctaacgc cctcgtcaag    780
gactacttcg aaaggcctaa cgtgagcaat gttaagttga tagtccccga cggccccgaa    840
tgcctcttcg aactggcgga cagccctggc ctgaccacca tgcacatcta ctacgtggac    900
tcaccctggc tcatcaactg catcaacaac taggctcaag aactctacct ctgtcctcta    960
cacatggaat gtaaatagtt aataaattct gcagccaaaa aaaaaaaa                 1008
```

<210> SEQ ID NO 40
<211> LENGTH: 798
<212> TYPE: DNA
<213> ORGANISM: Ostrinia furnacalis Guenee

<400> SEQUENCE: 40

```
acatggggat gttttcatc  ctcgcagttt atcagaacac aattaaatta attaatttaa     60
aatgttcaaa ttaagtttca ttattttcat gttggtggct attgcgaacg ttttaagcag    120
tgacgcccca gccccagact gcacctcgcc tcttgagacc ggaccatgca gaggcgggaa    180
ggttgctttc ggctacgata ctgacttgga aggatgcaaa cagttcatct acggaggatg    240
tgacggcaac ggcaaccgtt acaacactct agaggagtgt caggctgctt gcgagagtga    300
ctgcaacaaa taataacgaa atgcaagcaa tcaattgggt atttgacagc acagtcaatt    360
gacatacttt ttttaaactg tcaaaacgca ccattcccta ttttcacat  tttgcaaagt    420
```

| | |
|---|---|
| agagggaatc taaaggtcat agcagactta tcaactcgga aagggatcat gacgagctat | 480 |
| catcgccttt cccgcgttgt caactgtcaa ctgcgaggcg aggcgtttac gttactgtgc | 540 |
| ggataggtgt gggttacagt atggagtttc atacaaatac tgatcgcatc gagttgatac | 600 |
| ggttacaatc cctgtccgtg ttgataagtg tgctacgtcc ttgagttagc aatgataact | 660 |
| aaagctaagt ggtgtcgtgt tattatcggt aattagtgtc aactacccaa ttgtatcgat | 720 |
| atgatttacc taaagatgaa gaaatattct ttttatttaa ctatgtattt attataaaag | 780 |
| caacagccaa aaaaaaaa | 798 |

```
<210> SEQ ID NO 41
<211> LENGTH: 624
<212> TYPE: DNA
<213> ORGANISM: Ostrinia furnacalis Guenee

<400> SEQUENCE: 41
```

| | |
|---|---|
| agtttgtgaa ggactctgat caaaatggca tactttggaa aggaattctc cttcgaaagg | 60 |
| gaagaaaatt tcgatgcatt cgccgatttt atcggtgcct ttgacgccaa cgccaagggc | 120 |
| ttcatgcagt acaagccgaa ccagatcctc gagaagaacg gggactccta caagctgatc | 180 |
| ttcaagaccc ccgccctgaa ccacgaggtg gtgttcaagt ctggagtgcc ttacagcgac | 240 |
| gtcatccgtg aaggtttgac ggctgaatcc accatcaccg tcgatggaga caccttcact | 300 |
| caggtccagg actacggccc ccttggctcc atcaccttca agagagagta cagcgccgac | 360 |
| caacttaaag tgactgtcac cagcagtaaa tgggacggcg ttgcctacag atactacaag | 420 |
| gcgtaatctt cctacagttt aacttaagat ttaggtagac tttaaattaa tttataact | 480 |
| ctgatttgct ataaatgtaa gccaacgaag aaataatttt aaaattgcag ttataaacta | 540 |
| actattgtaa ataacgagac accaattcac aagttttgat ctgttattgt aataaaatac | 600 |
| tttttcaccg aaaaaaaaaa aaaa | 624 |

```
<210> SEQ ID NO 42
<211> LENGTH: 1433
<212> TYPE: DNA
<213> ORGANISM: Ostrinia furnacalis Guenee

<400> SEQUENCE: 42
```

| | |
|---|---|
| acatgggaag cagtggtatc aacgcagagt acatgggaag cagtggtatc aacgcagagt | 60 |
| acatggggag ctatcgagat gaaggttttg gcgatcgcat tgcttttcgt ggcggtctac | 120 |
| gccaagcacg aggaatatgc tggttacaaa tcctactgtg taggacagaa gaaccaagca | 180 |
| cagcaacatg ctctgcagtc cttagagaat gagttccagc tagactttct gggccgtgtg | 240 |
| accagcagcc aggagccctt ggtcctggtc aagcctgaat tccaggctgc gttcaccaaa | 300 |
| agcctgaaag cctttggcct ctcctacagg gtccatgccg atgacgtagt caaagcgctc | 360 |
| cagaatgatg ataggattat cgaggaggtg gttcaagaga aggccaggaa tgggggtgcc | 420 |
| aggatccctt atgacaatta tcagcctcta agtgtctacg acgcctacct cgacgacatc | 480 |
| gctcgtcgct accccaacgt ggtcaccctc gtcagccccg ccaactcctt cgaaggccgc | 540 |
| cccatcaagt acctgaagat atccaccacc aacttccaag acaccagcaa gcctgtcatc | 600 |
| ttcattgacg gaggcatcca ctccagggaa tggatctcac cacccactgt cacttgggcg | 660 |
| atcaggaaac tggtggagga tgtcaccgaa cctgacctcc tggagaggtt cgactggatc | 720 |
| ctcttgccta tggtcaaccc tgatggttat gaacacagcc acacatctaa ccgtttctgg | 780 |
| aggaagacac gttcggccac cagcattgca ttatgccggg gagtcgacgg caaccgcaac | 840 |

```
tacgacttcg catggaacac cgtcggaacc agcaccaacc cttgctccga cacttacgga    900
ggccctacag ccttctccga aatcgagacc agggttgttc gtgacatcct ccacgagaac    960
ctcagcagaa tggctctgta cctcaccatg catagctttg gtagcatgat cctctaccct   1020
tggggacatg atggttcttt atccaacaac gcatttgcac tccagaccgt tggagttgct   1080
atggctgatg agatcttcac tcatagtctc cctaatttcc ctagatattc cgttggcaat   1140
tctcttctga ctattgggta cggcgcatca ggtgcttctg aggattacgc tcacagcatc   1200
ggcgtgcccc tgtcgtatac ttacgagctt ccagggttga acgctggtat gaacggtttc   1260
attctggacc ctcggttcat cgagcaggtc tgccgggaga cttgggcagg catcgtcgtg   1320
ggcgccagga gagctggcga cctcttcgtc ccccatcctt aaattctcta tttgaataag   1380
ttgttgatga tcttttttta taataaacat ttttatatta aacaaaaaaa aaa           1433
```

<210> SEQ ID NO 43
<211> LENGTH: 95
<212> TYPE: PRT
<213> ORGANISM: Ostrinia furnacalis Guenee

<400> SEQUENCE: 43

Met Pro Phe Lys Pro Ala Asp Asn Pro Lys Cys Pro Lys Cys Gly Lys
1               5                   10                  15

Ser Val Tyr Ala Ala Glu Glu Arg Val Ala Gly Gly Leu Lys Trp His
            20                  25                  30

Lys Met Cys Phe Lys Cys Gly Leu Cys Gln Lys Leu Leu Asp Ser Thr
        35                  40                  45

Asn Cys Ser Glu His Glu Gly Glu Leu Phe Cys Lys Val Cys His Ala
    50                  55                  60

Arg Lys Phe Gly Pro Lys Gly Tyr Gly Phe Gly Gly Ala Gly Cys
65                  70                  75                  80

Leu Ser Met Asp Ala Gly Glu His Leu Lys Ala Glu Asp Ala Asn
            85                  90                  95

<210> SEQ ID NO 44
<211> LENGTH: 205
<212> TYPE: PRT
<213> ORGANISM: Ostrinia furnacalis Guenee

<400> SEQUENCE: 44

Met Ala Asp Lys Asp Lys Lys Val Lys Lys Lys Ala Lys Glu Asp
1               5                   10                  15

Ala Pro Ala Glu Glu Ala Pro Ala Ala Pro Ala Ala Ser Gly
            20                  25                  30

Gly Ser Glu Arg Gln Ser Ser Arg Gly Ser Arg Lys Ala Lys Arg Thr
        35                  40                  45

Gly Ser Asn Val Phe Ser Met Phe Ser Gln Lys Gln Val Ala Glu Phe
    50                  55                  60

Lys Glu Ala Phe Gln Leu Met Asp His Asp Lys Asp Gly Ile Ile Gly
65                  70                  75                  80

Lys Asn Asp Leu Arg Ala Thr Phe Asp Ser Leu Gly Arg Leu Ala Ser
            85                  90                  95

Glu Lys Glu Leu Asp Glu Met Val Asn Glu Ala Pro Gly Pro Ile Asn
            100                 105                 110

Phe Thr Gln Leu Leu Thr Leu Phe Ala Asn Arg Met Ser Gly Gly Ser
            115                 120                 125

```
Asp Glu Asp Asp Val Val Ile Asn Ala Phe Lys Thr Phe Asp Glu Glu
    130                 135                 140
Gly Lys Ile Asp Ser Glu Arg Leu Arg His Ala Leu Met Thr Trp Gly
145                 150                 155                 160
Asp Lys Phe Ser Ala Asp Glu Val Asp Glu Ala Tyr Asp Gln Met Glu
                165                 170                 175
Ile Asp Asp Lys Gly Phe Ile Asp Thr Thr Lys Leu Ile Thr Met Leu
            180                 185                 190
Thr Ala Ala Glu Glu Asp Gly Gly Glu Ala Ala
    195                 200                 205
```

<210> SEQ ID NO 45
<211> LENGTH: 287
<212> TYPE: PRT
<213> ORGANISM: Ostrinia furnacalis Guenee

<400> SEQUENCE: 45

```
Met Lys Ser Met Lys Ser Met Lys Ser Ser Leu Leu Phe Leu Leu Val
1               5                   10                  15
Val Ala Val Ala Ala Ala Glu Leu Leu Gln Pro Asn Thr Arg Tyr His
                20                  25                  30
Glu Thr Glu Gly Ile Pro Lys Phe Gln Leu Met Lys Gln Leu Glu Glu
            35                  40                  45
Gly Thr Asp Phe Asp Gly Gly Arg Ile Trp Gly Gly Gln Ala Val Ser
    50                  55                  60
Gly Gly Thr His Pro His Leu Gly Gly Leu Trp Ile Thr Leu Thr Thr
65                  70                  75                  80
Gly Gln Asn Ser Ile Cys Gly Ser Ser Leu Val Ser Asn Thr Arg Ser
                85                  90                  95
Val Thr Ala Ala His Cys Trp Arg Thr Ser Thr Leu Gln Ala Thr Met
                100                 105                 110
Phe Thr Ile Val Trp Asn Ser Asn Ser Ile Phe Trp Gly Gly Thr Arg
            115                 120                 125
Ile Asn Thr Asn Gln Val Ile Glu His Pro Asn Tyr Asn Val Trp Asn
    130                 135                 140
Leu Asn Asn Asp Val Ala Val Ile Ile His Asn His Val Asn Phe Asn
145                 150                 155                 160
Asn Asn Ile Gln Pro Ile Ala Leu Ala Thr Gly Ser Gln Thr Tyr Ala
                165                 170                 175
Gly Thr Trp Ala Val Ala Ala Gly Tyr Gly Gln Thr Gly Asp Gly Asn
            180                 185                 190
Ser Pro Ser Gly Thr Lys Phe Gln Ala Asn Leu Leu Val Ile Thr Asn
    195                 200                 205
Ser Ala Cys Gln Gly Thr Trp Met Pro Gly Ile Val Ile Ala Ser Thr
    210                 215                 220
Leu Cys Val Ser Thr Ala His Gly Ser Ser Thr Cys Pro Gly Asp Ser
225                 230                 235                 240
Gly Gly Pro Leu Ala Val Gly Ser Gly Asn Asn Arg Gln Leu Ile Gly
                245                 250                 255
Ile Thr Ser Phe Gly Thr Gln Trp Cys Ala Gln His Pro Ala Gly
            260                 265                 270
Phe Ala Arg Val Thr Ser Phe Ala Ser Trp Phe Asn Ser His Met
    275                 280                 285
```

<210> SEQ ID NO 46

<211> LENGTH: 281
<212> TYPE: PRT
<213> ORGANISM: Ostrinia furnacalis Guenee

<400> SEQUENCE: 46

```
Met Ala Val Lys Thr Gly Ile Leu Phe Phe Thr Leu Leu Val Gly Cys
1               5                   10                  15

Leu Ala Ile Pro Lys Pro Ala Ser Asp Asp Leu Ser Gln Phe Phe Glu
            20                  25                  30

His Ala Asn Pro Asp Ser Arg Ile Val Gly Gly Thr Val Ala Ala Ile
        35                  40                  45

Gly Ala His Pro His Met Val Ala Met Ser Asn Gly Leu Leu Ile Arg
    50                  55                  60

Ser Phe Val Cys Gly Gly Ser Leu Ile Ser Ser Arg Thr Val Leu Thr
65                  70                  75                  80

Ala Ala His Cys Ile Ala Ala Val Phe Ser Phe Gly Ser Leu Ser Ser
                85                  90                  95

Ser Leu Arg Val Thr Val Gly Thr Asn Asn Trp Asn Gln Gly Gly Val
            100                 105                 110

Ala Tyr Ala Leu Ala Arg Asn Val Thr His Glu His Tyr Val Ser Gln
        115                 120                 125

Ile Ile Lys Asn Asp Ile Gly Val Leu Ile Thr Ser Ser Pro Val Val
    130                 135                 140

Phe Thr Asn Leu Val Gln Pro Ile Thr Val Ser Tyr Asp Tyr Ala Gly
145                 150                 155                 160

Ala Gly Ile Gln Ser Arg Ala Ala Gly Trp Gly Arg Ile Arg Ala Gly
                165                 170                 175

Gly Pro Ile Ser Ala Gln Leu Leu Glu Leu Thr Val Thr Thr Ile Ser
            180                 185                 190

Gly Asp Gln Cys Val Arg Gly Val Ala Gln Ala Ser Val Asp Phe Asn
        195                 200                 205

Val Ala Ala Pro Pro Val Glu Pro His Ile Glu Leu Cys Ile Ile His
    210                 215                 220

Ser Pro Asn His Gly Met Cys Asn Gly Asp Ser Gly Ser Ala Leu Val
225                 230                 235                 240

Arg Leu Asp Arg Gly Thr Gln Ile Gly Ile Val Ser Trp Gly Phe Pro
                245                 250                 255

Cys Ala Arg Gly Ala Pro Asp Met Phe Val Arg Val Ser Ala Phe Gln
            260                 265                 270

Asp Trp Val Ala Arg His Phe Val Ala
        275                 280
```

<210> SEQ ID NO 47
<211> LENGTH: 287
<212> TYPE: PRT
<213> ORGANISM: Ostrinia furnacalis Guenee

<400> SEQUENCE: 47

```
Met Lys Val Leu Leu Gly Ser Val Val Leu Val Leu Ala Ile Ala Ala
1               5                   10                  15

Ser Tyr Ala Glu Gly Pro Val Asn Tyr His Gln Arg Ile Gly Ile Pro
            20                  25                  30

Glu Ala Ala Lys Ile Arg Arg Thr Glu Glu Asp Ala Ala Lys Ala Gly
        35                  40                  45

Val Asp Leu Arg Ile Val Gly Gly Ser Asn Val Asp Ile Ser Gln Val
    50                  55                  60
```

```
Pro Tyr Gln Val Gly Leu Val Ile Gln Ile Leu Trp Ile Leu Thr Ser
 65                  70                  75                  80

Val Cys Gly Gly Ser Leu Ile Ser Asn Thr Arg Val Ile Thr Ala Ala
                 85                  90                  95

His Cys His His Asp Gly Ser Val Thr Ala Gln Ser His Thr Val Val
            100                 105                 110

Leu Gly Ser Asn Thr Ile Phe Ser Gly Gly Val Arg Gln Thr Thr Ser
        115                 120                 125

Asp Ile Val Met His Pro Gln Trp Thr Pro Glu Thr Val Ala Asn Asp
130                 135                 140

Ile Ala Val Ile Arg Ile Asn Ala Val Thr Phe Thr Asn Val Ile Gln
145                 150                 155                 160

Pro Ile Ser Leu Pro Ser Gly Ser Gln Leu Asn Asn Asn Phe Val Gly
                165                 170                 175

Gln Val Gly Ile Ala Ser Gly Phe Gly Arg Thr Ser Asp Gly Ala Asn
            180                 185                 190

Ile Pro Asn Asn Gln Leu Val Ser Trp Val Arg Val Pro Ile Ile Thr
        195                 200                 205

Asn Gln Ala Cys Ala Ser Val Phe Gly Pro Phe Ile Leu Ser Ser Thr
210                 215                 220

Ile Cys Thr Asn Gly Ser Gly Gly Met Gly Thr Cys Gln Gly Asp Ser
225                 230                 235                 240

Gly Gly Pro Leu Ala Val Glu Val Gly Asn Ser Arg Val Leu Val Gly
                245                 250                 255

Val Thr Ser Phe Gly Ala Ala Ala Gly Cys Gln Ala Gly Leu Pro Ala
            260                 265                 270

Ala Tyr Ala Arg Val Thr Ser Phe Ile Ser Trp Ile Leu Ala Ile
        275                 280                 285

<210> SEQ ID NO 48
<211> LENGTH: 256
<212> TYPE: PRT
<213> ORGANISM: Ostrinia furnacalis Guenee

<400> SEQUENCE: 48

Met Ser Phe Asn Asn Lys Val Ala Leu Val Thr Gly Ala Ser Ser Gly
 1               5                  10                  15

Ile Gly Ala Ala Ile Ala Leu Lys Phe Ala Gly Glu Gly Ala Asn Val
            20                  25                  30

Ala Ile Val Gly Arg Asn Ala Ala Lys Leu Lys Asp Val Thr Glu Ser
        35                  40                  45

Ile Ser Lys Val Gly Asn Lys Pro Leu Val Ile Thr Ala Asp Val Thr
    50                  55                  60

Lys Glu Ser Asp Ala Gln Arg Ile Ile Asn Asp Thr Val Lys His Phe
65                  70                  75                  80

Gly Lys Leu Asp Ile Leu Val Asn Asn Ala Gly Val Ile Arg Tyr Ala
                85                  90                  95

Ser Ile Thr Glu Ala Glu Ala Met Ala Ala Phe Asp His Ile Met Ser
            100                 105                 110

Thr Asn Leu Arg Ser Ala Val Tyr Met Thr Asn Leu Ala Ala Lys His
        115                 120                 125

Leu Ile Glu Thr Lys Gly Asn Ile Ile Asn Ile Ser Ser Val Thr Gly
    130                 135                 140

Gln Met Val Met Glu Lys Ser Phe Ala Tyr Cys Thr Ser Lys Ala Ala
```

```
                145                 150                 155                 160
Met Asp His Phe Ala Arg Ala Ile Ala Leu Asp Phe Ala Pro His Gly
                    165                 170                 175

Val Arg Val Asn Asn Ile Ser Pro Gly Pro Val Arg Thr Asp Ile Val
            180                 185                 190

Glu Asn Met Gly Val Ser Ala Glu Ile Gln Ala Ala Val Trp Glu Thr
                195                 200                 205

Phe Lys Ala Ala Thr Pro Leu Lys Arg Ile Ser Glu Pro Ser Glu Ile
    210                 215                 220

Ala Glu Leu Ala Ala Phe Leu Ala Ser Asp Lys Ala Val Gly Ile Thr
225                 230                 235                 240

Gly Ser Ile Tyr Val Thr Asp Asn Gly Val Leu Ser Arg Ser Lys
                    245                 250                 255

<210> SEQ ID NO 49
<211> LENGTH: 304
<212> TYPE: PRT
<213> ORGANISM: Ostrinia furnacalis Guenee

<400> SEQUENCE: 49

Met Thr Met Asp Lys Leu Ile Val Leu Ala Ala Cys Ile Ala Ala Ala
1               5                   10                  15

Ser Ala Leu Gly Ser Trp Lys Ser Gly Leu Ser Val Arg Phe Gly Val
                20                  25                  30

Gly Leu Phe Gly Trp Gly Ser Ser Tyr Phe Ile His Val Pro Gln Thr
            35                  40                  45

Val Ala Asp Ala Lys Asn Ser Arg Trp Leu Glu Thr Pro Arg Pro Asp
    50                  55                  60

Gly Pro Leu Ser Ser Leu Ile Met Met Cys Pro Ser Gln Asn Asp Val
65                  70                  75                  80

Val Leu Cys Ala Leu Tyr Asp Asp Asn Gly Asp Val Ala Gly Leu Gln
                85                  90                  95

Ile Ala Leu Pro Thr Asp Ser Tyr Thr Gly Ala Val Leu Asp Trp Ala
                100                 105                 110

Thr Gln Gly Tyr Thr Tyr Trp Thr Ala Pro Ala Asn Ser Asn Gly Gln
            115                 120                 125

Val Arg Asn Tyr Trp Thr Leu Gln Gln Tyr Phe Val Ser Glu Ala Thr
    130                 135                 140

Leu Lys Lys Ser Lys Glu Glu Arg Arg Ala Ser Arg Val Ala Gly Arg
145                 150                 155                 160

Val Leu Gln Glu Asn Ala Val Trp Val Thr Gly Phe Asn Gly Asp Leu
                165                 170                 175

Met Arg Ile Ser Gly Asn Ala Asn Glu Val Thr Asp Thr Ala Thr Thr
            180                 185                 190

His Phe Thr Lys Gln Ala Cys Ile Ile Leu Met Gly Arg His Tyr Tyr
    195                 200                 205

Tyr Asn Met Thr Thr Ala Thr Glu Cys Arg Ser Asp Thr Leu Leu Pro
    210                 215                 220

Trp Phe Pro Leu Leu Asp Val Gly Thr Asp Gln Leu Ile Gly Met Gly
225                 230                 235                 240

Phe Thr Ser Phe Gly Gln Leu Pro Ala Asn Ala Leu Val Lys Asp Tyr
                245                 250                 255

Phe Glu Arg Pro Asn Val Ser Asn Val Lys Leu Ile Val Pro Asp Gly
    260                 265                 270
```

```
Pro Glu Cys Leu Phe Glu Leu Ala Asp Ser Pro Gly Leu Thr Thr Met
            275                 280                 285

His Ile Tyr Tyr Val Asp Ser Pro Trp Leu Ile Asn Cys Ile Asn Asn
        290                 295                 300
```

<210> SEQ ID NO 50
<211> LENGTH: 83
<212> TYPE: PRT
<213> ORGANISM: Ostrinia furnacalis Guenee

<400> SEQUENCE: 50

```
Met Phe Lys Leu Ser Phe Ile Ile Phe Met Leu Val Ala Ile Ala Asn
1               5                   10                  15

Val Leu Ser Ser Asp Ala Pro Ala Pro Asp Cys Thr Ser Pro Leu Glu
            20                  25                  30

Thr Gly Pro Cys Arg Gly Gly Lys Val Ala Phe Gly Tyr Asp Thr Asp
        35                  40                  45

Leu Glu Gly Cys Lys Gln Phe Ile Tyr Gly Gly Cys Asp Gly Asn Gly
    50                  55                  60

Asn Arg Tyr Asn Thr Leu Glu Glu Cys Gln Ala Ala Cys Glu Ser Asp
65                  70                  75                  80

Cys Asn Lys
```

<210> SEQ ID NO 51
<211> LENGTH: 133
<212> TYPE: PRT
<213> ORGANISM: Ostrinia furnacalis Guenee

<400> SEQUENCE: 51

```
Met Ala Tyr Phe Gly Lys Glu Phe Ser Phe Glu Arg Glu Glu Asn Phe
1               5                   10                  15

Asp Ala Phe Ala Asp Phe Ile Gly Ala Phe Asp Ala Asn Ala Lys Gly
            20                  25                  30

Phe Met Gln Tyr Lys Pro Asn Gln Ile Leu Glu Lys Asn Gly Asp Ser
        35                  40                  45

Tyr Lys Leu Ile Phe Lys Thr Pro Ala Leu Asn His Glu Val Val Phe
    50                  55                  60

Lys Ser Gly Val Pro Tyr Ser Asp Val Ile Arg Glu Gly Leu Thr Ala
65                  70                  75                  80

Glu Ser Thr Ile Thr Val Asp Gly Asp Thr Phe Thr Gln Val Gln Asp
                85                  90                  95

Tyr Gly Pro Leu Gly Ser Ile Thr Phe Lys Arg Glu Tyr Ser Ala Asp
            100                 105                 110

Gln Leu Lys Val Thr Val Thr Ser Ser Lys Trp Asp Gly Val Ala Tyr
        115                 120                 125

Arg Tyr Tyr Lys Ala
    130
```

<210> SEQ ID NO 52
<211> LENGTH: 427
<212> TYPE: PRT
<213> ORGANISM: Ostrinia furnacalis Guenee

<400> SEQUENCE: 52

```
Met Lys Val Leu Ala Ile Ala Leu Leu Phe Val Ala Val Tyr Ala Lys
1               5                   10                  15

His Glu Glu Tyr Ala Gly Tyr Lys Ser Tyr Cys Val Gly Gln Lys Asn
            20                  25                  30
```

```
Gln Ala Gln Gln His Ala Leu Gln Ser Leu Glu Asn Glu Phe Gln Leu
            35                  40                  45

Asp Phe Leu Gly Arg Val Thr Ser Ser Gln Glu Thr Leu Val Leu Val
 50                      55                  60

Lys Pro Glu Phe Gln Ala Ala Phe Thr Lys Ser Leu Lys Ala Phe Gly
 65                  70                  75                  80

Leu Ser Tyr Arg Val His Ala Asp Asp Val Val Lys Ala Leu Gln Asn
                    85                  90                  95

Asp Asp Arg Ile Ile Glu Val Val Gln Glu Lys Ala Arg Asn Gly
                100                 105                 110

Gly Ala Arg Ile Pro Tyr Asp Asn Tyr Gln Pro Leu Ser Val Tyr Asp
                115                 120                 125

Ala Tyr Leu Asp Asp Ile Ala Arg Arg Tyr Pro Asn Val Val Thr Leu
            130                 135                 140

Val Ser Pro Ala Asn Ser Phe Glu Gly Arg Pro Ile Lys Tyr Leu Lys
145                 150                 155                 160

Ile Ser Thr Thr Asn Phe Gln Asp Thr Ser Lys Pro Val Ile Phe Ile
                    165                 170                 175

Asp Gly Gly Ile His Ser Arg Glu Trp Ile Ser Pro Pro Thr Val Thr
                180                 185                 190

Trp Ala Ile Arg Lys Leu Val Glu Asp Val Thr Glu Pro Asp Leu Leu
            195                 200                 205

Glu Arg Phe Asp Trp Ile Leu Leu Pro Met Val Asn Pro Asp Gly Tyr
210                 215                 220

Glu His Ser His Thr Ser Asn Arg Phe Trp Arg Lys Thr Arg Ser Ala
225                 230                 235                 240

Thr Ser Ile Ala Leu Cys Arg Gly Val Asp Gly Asn Arg Asn Tyr Asp
                    245                 250                 255

Phe Ala Trp Asn Thr Val Gly Thr Ser Thr Asn Pro Cys Ser Asp Thr
                260                 265                 270

Tyr Gly Gly Pro Thr Ala Phe Ser Glu Ile Glu Thr Arg Val Val Arg
            275                 280                 285

Asp Ile Leu His Glu Asn Leu Ser Arg Met Ala Leu Tyr Leu Thr Met
290                 295                 300

His Ser Phe Gly Ser Met Ile Leu Tyr Pro Trp Gly His Asp Gly Ser
305                 310                 315                 320

Leu Ser Asn Asn Ala Phe Ala Leu Gln Thr Val Gly Val Ala Met Ala
                    325                 330                 335

Asp Glu Ile Phe Thr His Ser Leu Pro Asn Phe Pro Arg Tyr Ser Val
                340                 345                 350

Gly Asn Ser Leu Leu Thr Ile Gly Tyr Gly Ala Ser Gly Ala Ser Glu
            355                 360                 365

Asp Tyr Ala His Ser Ile Gly Val Pro Leu Ser Tyr Thr Tyr Glu Leu
370                 375                 380

Pro Gly Leu Asn Ala Gly Met Asn Gly Phe Ile Leu Asp Pro Arg Phe
385                 390                 395                 400

Ile Glu Gln Val Cys Arg Glu Thr Trp Ala Gly Ile Val Val Gly Ala
                    405                 410                 415

Arg Arg Ala Gly Asp Leu Phe Val Pro His Pro
                420                 425

<210> SEQ ID NO 53
<211> LENGTH: 638
```

<212> TYPE: DNA
<213> ORGANISM: Helicoverpa armigera Hubner

<400> SEQUENCE: 53

```
attcgaacat cgcgcaccgc agtctcggca tctacgccct gaactgtata cgcgtccggg    60
agatcatccc gcagcgactt cgacgaacag gataagttaa gcgagcacaa tgcctttcaa   120
accagcagat aaccctaagt gccctaaatg cggcaaatca gtatacgcag ctgaggagag   180
agtcgccgga ggactcaaat ggcacaaaat gtgcttcaag tgcggcctgt gccagaagtt   240
gctggactcc accaactgct cagaacacga aggtgaactg tactgcaaag tgtgccatgc   300
acgtaaattc ggaccaaaag gctacggctt cggcggtggt gctggctgcc tgtccatgga   360
cactggtgac cacctgaagg ctgagaatgc gaattgagcg agcagccctc cagcagaact   420
agcgggtcgc cgacacacat ctcggcccac cagcgacgcc tcgcgaacgc acgccatact   480
gtactttaaa ttactctagt taggattatt tattcgctat cgcttaattt aatttgttca   540
tcggtattat ttattattta taaaaaacac aaataaataa aacagtcgac tgttttattt   600
atttgtgttt tttataaata ataaataata ccgatgaa                          638
```

<210> SEQ ID NO 54
<211> LENGTH: 1123
<212> TYPE: DNA
<213> ORGANISM: Helicoverpa armigera Hubner

<400> SEQUENCE: 54

```
acatggggag tatttgttag attaggtacg ttaccagtgt tgcgtcttgt agaacattag    60
tttaattttt ttgtagtttc agctcctagt tttgcctgga aacacgatga aaaccttcat   120
tgtagtgtgt ttggctctgg ctagcttcgc ctgtgcggag cagggatctt tccctgggta   180
ctccacgttt gggtacctag agaagtatgc tattcctcat gcggagaaac ttcgcgcggc   240
tgaggaaaag ttcctcgcta gccagtctgg ctccaggatc gtaggtggag ttcccgctgg   300
ccagggacag tacccatacc aggctggtct cctcctctcc atcatcggtt tcgaaggcaa   360
cggtatctgc ggaggctccc tgatcagcgc caaccgagta gcaacagccg cccactgctg   420
gttcgacggt atccaccaag gatggaaggt cacagttgtg ctcggttcca ccctgctgtt   480
ctctggaggc actcgtcttg agaccagtgt ggtcgccatg cacccctaact ggactcctgc   540
actcgtccgc aatgatgttg ctgtgattta cttgcccaac tcygtrcaga tttcagccaa   600
tattgcacca attgctttgg ctagcggmtc ttcagaattc gccggtgtct ccgccattgc   660
ctccggtttt ggattaacca gctctagcgg acaaatcacc gctaaccagt tcctgagcca   720
cgtcaacctg aacgtgatca ccaacatcgc ctgcagcgtc gccttcccct tcattgtcca   780
gccttccaac atctgcacca gtggtatcgg aggtgttggt acttgcagcg gtgactctgg   840
tggtcctctg gtcaccaacc agaatggaca gaacgtcttg attggtatca cttccttcgg   900
ctcggctttc ggctgccagg tcaacctgcc ctcagtcttc gctcgtgtca catcattcgt   960
ctctttcctc aaccaacatt tgtaattctg aacaaactgt aaactatact gtaaataaga  1020
ctggagttgg aatctttttcc agcatattcg ttgtattttt acaaaaaaat tgaagctata  1080
taataagcaa taaataaaa tctgctctcg taaaaaaaaa aaa                     1123
```

<210> SEQ ID NO 55
<211> LENGTH: 968
<212> TYPE: DNA
<213> ORGANISM: Helicoverpa armigera Hubner

<400> SEQUENCE: 55

```
tttttttttt tttttcattc aaattcattt atttctcccc attaaattaa gatgcagtct      60
taagcagttt ccaaagtcct tttatcggaa tatttacaag tcctttagtc tgtctattta     120
gactacatta gcctggagcc aggactggta ggcgctgact ctgacgaaca tgtcggggc      180
gccgcgggcg caggggaagc cccaggacac gatgccgaac tgctggccgt tgtcggcgcg    240
ggtcagagcg ctgccggagt caccattgca agttccgaat ccaggagcgt ggaaggtgca    300
gacctcgatg tgaggttcaa cgggaggagc gcgtacattc agctcgacgg aggcgcgggc    360
cacgcgagcc acgcagtcgt taccgtcgat ggtggtgggg aacagctcca ggagagtggc    420
tgagagggca ccgccagccc tgattctacc ccatccagcg accctagcgt taacaccacc    480
agggatgtga gcgtaagtca gaggcacagt cctgacgagg ttgttcagag ccacgttgtt    540
ggaggtgatg aggataccga tgtcgttctt gatggtggca gacacgtagt tggggtgggt    600
gacgttgcgg gccaaggtgt aggccacgcc gccgctgttc cagcggtttg tgccgactgt    660
cacgcggaga gagttaacca gcgagccacc actgaacacc gcagcgatac agtgagcagc    720
tgtcagcaca gtcctagtcg tgatcaagga accgccgcag aggaagctcc tcaccagcac    780
gccactggac atggccacca tgtgagggtg gctgcccaca gccgctgggt gccgccaac    840
gatgcgagcg ctggcgtcag tgtggtcgaa gaagcgtgac atgtcatctt cgggcgcggg    900
gagggcaata cacccaacca ggagcgagat caccagaagt ccggttttga agtccatgtt    960
taacaacg                                                             968
```

<210> SEQ ID NO 56
<211> LENGTH: 970
<212> TYPE: DNA
<213> ORGANISM: Helicoverpa armigera Hubner

<400> SEQUENCE: 56

```
atccaagaat tcgcacgaga caaatcaaca tgagctgtcc ctaggagtgt gctagcttgg      60
ccgtcgccgt atcggcagtg gagatcgcca ctcctgatgc cgacagccct gtcttcggct    120
accacgccaa gtttggtatt gctgaggctg cgaggatcaa gagcgcggag gaagttcaga    180
gcttcaacgg ccagaggatc gttggaggat ccatcaccaa cattgccaac gtcccatacc    240
aggctggtct tgtgatcacc atcttcatct tccaatccgt gtgcggtgct ccctcatct     300
cccacaaccg cctggtgact gctgctcact gcaaattcga cggtgtcttg aacgctagct    360
ccttcaccgt tgtgcttggc tccaacaccc tgttcttcgg cggtactcgc atcaacacca    420
atgatgtcgt catgcacccc aactggaatc ctgctaccgt tgccaatgac atcgctgtca    480
ttcgcatcag ttccgtcagc ttcaacaatg tgatccagcc catcgctctt cccagtggag    540
acgaactcaa caacctcttc gtcggcgcca acgctcttgc ctccggattt ggccgcacta    600
gcgacagtgg aagcattggt accaaccaac agctgagctc tgtgaccatc cccgtgatca    660
ccaacgctca gtgcgctgcc gtgtacggcc ccgcctttgt gcacgcctcc aacatctgca    720
ccagcggcgc cggcggcaag ggtacttgca acggtgactc cggtggccct ctcgctgtcg    780
acagcaacaa caggaagatc ttgatcgtg ttacttcata cggtgctgct gacggttgcg     840
ccgctggttt ccctgctgcc ttcgccagag tcacctcctt cgtcagctgg gtccagtccc    900
aataatctcc tcctctctta aacttataat gcttaaatta aatttatttt acttcaaaaa    960
aaaaaaaaaa                                                           970
```

<210> SEQ ID NO 57
<211> LENGTH: 679
<212> TYPE: DNA
<213> ORGANISM: Helicoverpa armigera Hubner

<400> SEQUENCE: 57

```
agaaactgaa gaatactgcc aagaaatgtg gaaacccttt agtgatcgtc gctgatgtca    60
caaagaaga cgacgtcaaa agaattgcca gtgaaacgtt gaaacatttt gggaaactcg   120
atgttctggt caacaatgct ggcatttgtc catttgctag tattcaagct gacaacgcaa   180
tgcaggtcta cgatgaaata atgtctacaa acctccggtc taccgttcta ctgacacatc   240
ttaccgtccc tgaacttgtg aaaactaaag gcaacattat caatatttca gtgttgctg   300
cttccaaagt cgctctaggt cttttttgcgt actgtgcgtc gaaggcagct atggatcact   360
tctctagagc gattgcacta gagctggctc aagtggtgt acgtgtaaat gtagtcaatc   420
caggacccgt ggcgactgac atcggtgcta ccatgttccc aacaaaagag gaacaagaca   480
atttctttaa aaaagtcgtg gatggaactg cattgggcag gatatcggag cctgaagaaa   540
tagctgatat tgttctgttc ctagcgagtg ataaagctag agggatcacc ggttcaagtt   600
atgtttctga taatggatat tcggttaaag gcgtacaagc ttgattaatt ttattaataa   660
acgtaatttt aaatagtgc                                                679
```

<210> SEQ ID NO 58
<211> LENGTH: 672
<212> TYPE: DNA
<213> ORGANISM: Helicoverpa armigera Hubner

<400> SEQUENCE: 58

```
agaccggccc tacccctccca agtggctatg agaacctggt actgtatggc cccgctgacg    60
acaacaccct caacttatac tacgatgaca actatcagat tgctgcattc caaattggtc   120
tggacaaaga acaaataagc gattcggtat acgatttcga aaatcaagga ttcgcaagct   180
ggaccactac attgtctaat ggcacatcta gagattattg gaccatcaga gcatactttt   240
ccactgctga ttatcttgcg actgacgcaa caactcgcaa ctcttcaaga aatactgaga   300
cgttgatcca gggtggttcc atggtagtga ctggtttcaa cggagaattg tacaccattt   360
cctccgaccc taccgtactt gccgacacaa gcgtcagtgg gttcacagaa caagcctgca   420
tgatatatat gggtcaccat ttctactaca acatgactac aagcttggag tgcgctgaag   480
gaaggctgtt cccctggttc ccactttcct acaacggagt agtgatgggc attggtttca   540
actttatcgg caaatacgac gtgagacctg acaatttcaa ttatttcgaa agccctggag   600
tagcagctgt taagatcatc gtaccaaaag gcccgcaatg tttctacgag ttagcagaaa   660
accccggcgt gg                                                       672
```

<210> SEQ ID NO 59
<211> LENGTH: 400
<212> TYPE: DNA
<213> ORGANISM: Helicoverpa armigera Hubner

<400> SEQUENCE: 59

```
ttcagtcaac atgtctttcc ttggcaaaac ttacaccttc gtcaaacagg agaatatgga    60
cggattcctg aaatctgtcg gtctccctga cgacaaaatc gagccagtcc tgaagttcac   120
tcctgaacag aagatcattc aggaaggtga tggctacaag tacatcactc agggtcgcga   180
tggcccctaga gaagtcacat tcaagtccgg agtagaattc gacgatctta ttggacctga   240
```

```
gaaaattccc gctaagacta catacgtcgt tgatggcaac aaagtgacac agaccatcaa       300
atcagctatg ggagtcggca ccttcaccag ggagttcgtt ggcgatgaac ttatcatcac       360
catggtcacc gacaaatggg acggcgttgc caagagatac                             400

<210> SEQ ID NO 60
<211> LENGTH: 899
<212> TYPE: DNA
<213> ORGANISM: Helicoverpa armigera Hubner

<400> SEQUENCE: 60
cattcctcga aaggtcgtcc catcaagtac gtcaaaatcc tccacaacct actttgaaga        60
ccacagccaa gcctgtcatc ctcatcgatg gtggtatcca cgccagggaa atggatctct       120
ccccccactg ttaccttggg ctattcataa gctggttgaa gatgttactg aaagagatct       180
tctagataat tttgactgga tcctcttgcc tgtggtcaac cctgatggat ataaattcac       240
ttttaccaat tcccgtttct ggcgtaagac tcgttccacg gaccagcacg ttttaagcgg       300
tatctgccca ggagtcgacg gtaaccgcaa ctatgacttc ttctggaaca ccgttggtac       360
cagcaacacc ccatgctcag acgtctacgc tggatccaga gccttctccg aagtcgaaac       420
cagggtcgtc agagatatcc tccatgaaca tttagcacgc atggctctgt acatcaccat       480
gcacagtttc ggaagcatga tcttataccc atggggtcat gatggctccc tatctcataa       540
cggccttggt cttcatacgg tgggagttgc tatggcaacg gcaatcaatc agaattctct       600
atctcacttc cgatcttatg ttgttggaaa ttcagcttta gttctgaact atccagcggc       660
tggtgcgtca gaagattatg ctcatcaaat tggcgtgcct ctatcctata cttttgagct       720
acctggtcta tccaacacat tacttggatt caatttgaac cctaggtaca ttcaacaagt       780
atgcaatgaa acttggcaag gtctcatcgt tggagctagg agagctggtg atttatttag       840
aaataaaaaa ctttaaagac tgaaaaaaaa aaaaaaaaaa aaaaaaaaaa aaaaaaaa         899

<210> SEQ ID NO 61
<211> LENGTH: 26
<212> TYPE: DNA
<213> ORGANISM: Artificial Sequence
<220> FEATURE:
<223> OTHER INFORMATION: Synthetic

<400> SEQUENCE: 61
ttcggcggtg gcgctggctg cctttc                                            26

<210> SEQ ID NO 62
<211> LENGTH: 26
<212> TYPE: DNA
<213> ORGANISM: Artificial Sequence
<220> FEATURE:
<223> OTHER INFORMATION: Synthetic

<400> SEQUENCE: 62
ttcgccaacc gcatgtccgg cggctc                                            26

<210> SEQ ID NO 63
<211> LENGTH: 21
<212> TYPE: DNA
<213> ORGANISM: Artificial Sequence
<220> FEATURE:
<223> OTHER INFORMATION: Synthetic

<400> SEQUENCE: 63
cggcacgcgc ataaacacca a                                                 21
```

<210> SEQ ID NO 64
<211> LENGTH: 26
<212> TYPE: DNA
<213> ORGANISM: Artificial Sequence
<220> FEATURE:
<223> OTHER INFORMATION: Synthetic

<400> SEQUENCE: 64
tgcgcccgcg gcgctcccga tatgtt                                        26

<210> SEQ ID NO 65
<211> LENGTH: 26
<212> TYPE: DNA
<213> ORGANISM: Artificial Sequence
<220> FEATURE:
<223> OTHER INFORMATION: Synthetic

<400> SEQUENCE: 65
accaggcgtg cgcctcagtc ttcgga                                        26

<210> SEQ ID NO 66
<211> LENGTH: 26
<212> TYPE: DNA
<213> ORGANISM: Artificial Sequence
<220> FEATURE:
<223> OTHER INFORMATION: Synthetic

<400> SEQUENCE: 66
cgctggagag ggagcgaacg ttgcca                                        26

<210> SEQ ID NO 67
<211> LENGTH: 26
<212> TYPE: DNA
<213> ORGANISM: Artificial Sequence
<220> FEATURE:
<223> OTHER INFORMATION: Synthetic

<400> SEQUENCE: 67
ccgacaccgc caccacccac ttcacc                                        26

<210> SEQ ID NO 68
<211> LENGTH: 26
<212> TYPE: DNA
<213> ORGANISM: Artificial Sequence
<220> FEATURE:
<223> OTHER INFORMATION: Synthetic

<400> SEQUENCE: 68
accggaccat gcagaggcgg gaaggt                                        26

<210> SEQ ID NO 69
<211> LENGTH: 22
<212> TYPE: DNA
<213> ORGANISM: Artificial Sequence
<220> FEATURE:
<223> OTHER INFORMATION: Synthetic

<400> SEQUENCE: 69
atcttcaaga ccccgcccct ga                                            22

<210> SEQ ID NO 70
<211> LENGTH: 22
<212> TYPE: DNA
<213> ORGANISM: Artificial Sequence
<220> FEATURE:

<223> OTHER INFORMATION: Synthetic

<400> SEQUENCE: 70
tcgaaggccg ccccatcaag ta                                           22

<210> SEQ ID NO 71
<211> LENGTH: 26
<212> TYPE: DNA
<213> ORGANISM: Artificial Sequence
<220> FEATURE:
<223> OTHER INFORMATION: Synthetic

<400> SEQUENCE: 71
gcggtgcctc gcgaacgcac gccata                                       26

<210> SEQ ID NO 72
<211> LENGTH: 26
<212> TYPE: DNA
<213> ORGANISM: Artificial Sequence
<220> FEATURE:
<223> OTHER INFORMATION: Synthetic

<400> SEQUENCE: 72
ggacgagggc ggcgaagctg cgtagt                                       26

<210> SEQ ID NO 73
<211> LENGTH: 26
<212> TYPE: DNA
<213> ORGANISM: Artificial Sequence
<220> FEATURE:
<223> OTHER INFORMATION: Synthetic

<400> SEQUENCE: 73
gccgtcggct ccggcaacaa caggca                                       26

<210> SEQ ID NO 74
<211> LENGTH: 26
<212> TYPE: DNA
<213> ORGANISM: Artificial Sequence
<220> FEATURE:
<223> OTHER INFORMATION: Synthetic

<400> SEQUENCE: 74
actgggtcgc ccgccacttc gttgct                                       26

<210> SEQ ID NO 75
<211> LENGTH: 26
<212> TYPE: DNA
<213> ORGANISM: Artificial Sequence
<220> FEATURE:
<223> OTHER INFORMATION: Synthetic

<400> SEQUENCE: 75
tgctgctgcc ggttgccaag ctggat                                       26

<210> SEQ ID NO 76
<211> LENGTH: 21
<212> TYPE: DNA
<213> ORGANISM: Artificial Sequence
<220> FEATURE:
<223> OTHER INFORMATION: Synthetic

<400> SEQUENCE: 76
aatcgcgttg gactttgcgc c                                            21

```
<210> SEQ ID NO 77
<211> LENGTH: 26
<212> TYPE: DNA
<213> ORGANISM: Artificial Sequence
<220> FEATURE:
<223> OTHER INFORMATION: Synthetic

<400> SEQUENCE: 77
ttggccagct gcccgctaac gccctc                                          26

<210> SEQ ID NO 78
<211> LENGTH: 26
<212> TYPE: DNA
<213> ORGANISM: Artificial Sequence
<220> FEATURE:
<223> OTHER INFORMATION: Synthetic

<400> SEQUENCE: 78
caactgtcaa ctgcgaggcg aggcgt                                          26

<210> SEQ ID NO 79
<211> LENGTH: 26
<212> TYPE: DNA
<213> ORGANISM: Artificial Sequence
<220> FEATURE:
<223> OTHER INFORMATION: Synthetic

<400> SEQUENCE: 79
ggtccaggac tacggccccc ttggct                                          26

<210> SEQ ID NO 80
<211> LENGTH: 21
<212> TYPE: DNA
<213> ORGANISM: Artificial Sequence
<220> FEATURE:
<223> OTHER INFORMATION: Synthetic

<400> SEQUENCE: 80
acacgttcgg ccaccagcat t                                               21

<210> SEQ ID NO 81
<211> LENGTH: 28
<212> TYPE: DNA
<213> ORGANISM: Artificial Sequence
<220> FEATURE:
<223> OTHER INFORMATION: Synthetic

<400> SEQUENCE: 81
agtccagcaa cttctggcac agtccgca                                        28

<210> SEQ ID NO 82
<211> LENGTH: 22
<212> TYPE: DNA
<213> ORGANISM: Artificial Sequence
<220> FEATURE:
<223> OTHER INFORMATION: Synthetic

<400> SEQUENCE: 82
agctgcgtga agttgatcgg gc                                              22

<210> SEQ ID NO 83
<211> LENGTH: 26
<212> TYPE: DNA
<213> ORGANISM: Artificial Sequence
<220> FEATURE:
<223> OTHER INFORMATION: Synthetic
```

<400> SEQUENCE: 83
tggtgtttat gcgcgtgccg ccccag                                          26

<210> SEQ ID NO 84
<211> LENGTH: 26
<212> TYPE: DNA
<213> ORGANISM: Artificial Sequence
<220> FEATURE:
<223> OTHER INFORMATION: Synthetic

<400> SEQUENCE: 84
acgccacgca cgcactgatc gccgga                                          26

<210> SEQ ID NO 85
<211> LENGTH: 26
<212> TYPE: DNA
<213> ORGANISM: Artificial Sequence
<220> FEATURE:
<223> OTHER INFORMATION: Synthetic

<400> SEQUENCE: 85
aacggtcgcc ggggtccact gagggt                                          26

<210> SEQ ID NO 86
<211> LENGTH: 26
<212> TYPE: DNA
<213> ORGANISM: Artificial Sequence
<220> FEATURE:
<223> OTHER INFORMATION: Synthetic

<400> SEQUENCE: 86
atcggtcctc accggcccag ggctaa                                          26

<210> SEQ ID NO 87
<211> LENGTH: 26
<212> TYPE: DNA
<213> ORGANISM: Artificial Sequence
<220> FEATURE:
<223> OTHER INFORMATION: Synthetic

<400> SEQUENCE: 87
gcgccggggg taactatcag cgggca                                          26

<210> SEQ ID NO 88
<211> LENGTH: 28
<212> TYPE: DNA
<213> ORGANISM: Artificial Sequence
<220> FEATURE:
<223> OTHER INFORMATION: Synthetic

<400> SEQUENCE: 88
gcagtcactc tcgcaagcag cctgacac                                        28

<210> SEQ ID NO 89
<211> LENGTH: 22
<212> TYPE: DNA
<213> ORGANISM: Artificial Sequence
<220> FEATURE:
<223> OTHER INFORMATION: Synthetic

<400> SEQUENCE: 89
cggatgacgt cgctgtaagg ca                                              22

<210> SEQ ID NO 90
<211> LENGTH: 21

<212> TYPE: DNA
<213> ORGANISM: Artificial Sequence
<220> FEATURE:
<223> OTHER INFORMATION: Synthetic

<400> SEQUENCE: 90
agtcgtagtt gcggttgccg t                                                21

<210> SEQ ID NO 91
<211> LENGTH: 26
<212> TYPE: DNA
<213> ORGANISM: Artificial Sequence
<220> FEATURE:
<223> OTHER INFORMATION: Synthetic

<400> SEQUENCE: 91
accggctact ctctcctcgg ctgcgt                                           26

<210> SEQ ID NO 92
<211> LENGTH: 22
<212> TYPE: DNA
<213> ORGANISM: Artificial Sequence
<220> FEATURE:
<223> OTHER INFORMATION: Synthetic

<400> SEQUENCE: 92
tcggcgacct gcttctgtga ga                                               22

<210> SEQ ID NO 93
<211> LENGTH: 26
<212> TYPE: DNA
<213> ORGANISM: Artificial Sequence
<220> FEATURE:
<223> OTHER INFORMATION: Synthetic

<400> SEQUENCE: 93
ccgccccaga tcctgccgcc atcgaa                                           26

<210> SEQ ID NO 94
<211> LENGTH: 28
<212> TYPE: DNA
<213> ORGANISM: Artificial Sequence
<220> FEATURE:
<223> OTHER INFORMATION: Synthetic

<400> SEQUENCE: 94
accgccggcc ctgattctgc cccaacca                                         28

<210> SEQ ID NO 95
<211> LENGTH: 26
<212> TYPE: DNA
<213> ORGANISM: Artificial Sequence
<220> FEATURE:
<223> OTHER INFORMATION: Synthetic

<400> SEQUENCE: 95
ccgtcatggt ggcagtgcgc agcggt                                           26

<210> SEQ ID NO 96
<211> LENGTH: 21
<212> TYPE: DNA
<213> ORGANISM: Artificial Sequence
<220> FEATURE:
<223> OTHER INFORMATION: Synthetic

<400> SEQUENCE: 96

```
gcgaacacca tgtggcgcaa a                                           21

<210> SEQ ID NO 97
<211> LENGTH: 28
<212> TYPE: DNA
<213> ORGANISM: Artificial Sequence
<220> FEATURE:
<223> OTHER INFORMATION: Synthetic

<400> SEQUENCE: 97
tgctcagggg gccatcgggt cttggggt                                    28

<210> SEQ ID NO 98
<211> LENGTH: 26
<212> TYPE: DNA
<213> ORGANISM: Artificial Sequence
<220> FEATURE:
<223> OTHER INFORMATION: Synthetic

<400> SEQUENCE: 98
gtgcagtctg gggctggggc gtcact                                      26

<210> SEQ ID NO 99
<211> LENGTH: 26
<212> TYPE: DNA
<213> ORGANISM: Artificial Sequence
<220> FEATURE:
<223> OTHER INFORMATION: Synthetic

<400> SEQUENCE: 99
accacctcgt ggttcagggc gggggt                                      26

<210> SEQ ID NO 100
<211> LENGTH: 28
<212> TYPE: DNA
<213> ORGANISM: Artificial Sequence
<220> FEATURE:
<223> OTHER INFORMATION: Synthetic

<400> SEQUENCE: 100
tcctgatcgc ccaagtgaca gtgggtgg                                    28

<210> SEQ ID NO 101
<211> LENGTH: 43
<212> TYPE: DNA
<213> ORGANISM: Artificial Sequence
<220> FEATURE:
<223> OTHER INFORMATION: Synthetic

<400> SEQUENCE: 101
taatacgact cactataggg agaacatcgc gcaccgcagt ctc                   43

<210> SEQ ID NO 102
<211> LENGTH: 43
<212> TYPE: DNA
<213> ORGANISM: Artificial Sequence
<220> FEATURE:
<223> OTHER INFORMATION: Synthetic

<400> SEQUENCE: 102
taatacgact cactataggg agatcgctgg tgggccgaga tgt                   43

<210> SEQ ID NO 103
<211> LENGTH: 43
<212> TYPE: DNA
<213> ORGANISM: Artificial Sequence
```

```
<220> FEATURE:
<223> OTHER INFORMATION: Synthetic

<400> SEQUENCE: 103
taatacgact cactataggg agacccgctg gccagggaca gta                    43

<210> SEQ ID NO 104
<211> LENGTH: 43
<212> TYPE: DNA
<213> ORGANISM: Artificial Sequence
<220> FEATURE:
<223> OTHER INFORMATION: Synthetic

<400> SEQUENCE: 104
taatacgact cactataggg agacagccga aagccgagcc gaa                    43

<210> SEQ ID NO 105
<211> LENGTH: 43
<212> TYPE: DNA
<213> ORGANISM: Artificial Sequence
<220> FEATURE:
<223> OTHER INFORMATION: Synthetic

<400> SEQUENCE: 105
taatacgact cactataggg agaagccagg actggtaggc gct                    43

<210> SEQ ID NO 106
<211> LENGTH: 43
<212> TYPE: DNA
<213> ORGANISM: Artificial Sequence
<220> FEATURE:
<223> OTHER INFORMATION: Synthetic

<400> SEQUENCE: 106
taatacgact cactataggg agagccatgt ccagtggcgt gct                    43

<210> SEQ ID NO 107
<211> LENGTH: 43
<212> TYPE: DNA
<213> ORGANISM: Artificial Sequence
<220> FEATURE:
<223> OTHER INFORMATION: Synthetic

<400> SEQUENCE: 107
taatacgact cactataggg agatgtgcta gcttggccgt cgc                    43

<210> SEQ ID NO 108
<211> LENGTH: 43
<212> TYPE: DNA
<213> ORGANISM: Artificial Sequence
<220> FEATURE:
<223> OTHER INFORMATION: Synthetic

<400> SEQUENCE: 108
taatacgact cactataggg agatgcaagt acccttgccg ccg                    43

<210> SEQ ID NO 109
<211> LENGTH: 49
<212> TYPE: DNA
<213> ORGANISM: Artificial Sequence
<220> FEATURE:
<223> OTHER INFORMATION: Synthetic

<400> SEQUENCE: 109
taatacgact cactataggg agatgtggaa acccttagt gatcgtcgc                49
```

<210> SEQ ID NO 110
<211> LENGTH: 45
<212> TYPE: DNA
<213> ORGANISM: Artificial Sequence
<220> FEATURE:
<223> OTHER INFORMATION: Synthetic

<400> SEQUENCE: 110
taatacgact cactataggg agatcaggct ccgatatcct gccca                45

<210> SEQ ID NO 111
<211> LENGTH: 43
<212> TYPE: DNA
<213> ORGANISM: Artificial Sequence
<220> FEATURE:
<223> OTHER INFORMATION: Synthetic

<400> SEQUENCE: 111
taatacgact cactataggg agagaccggc cctaccctcc caa                  43

<210> SEQ ID NO 112
<211> LENGTH: 44
<212> TYPE: DNA
<213> ORGANISM: Artificial Sequence
<220> FEATURE:
<223> OTHER INFORMATION: Synthetic

<400> SEQUENCE: 112
taatacgact cactataggg agatgggaac cagggggaaca gcct                44

<210> SEQ ID NO 113
<211> LENGTH: 49
<212> TYPE: DNA
<213> ORGANISM: Artificial Sequence
<220> FEATURE:
<223> OTHER INFORMATION: Synthetic

<400> SEQUENCE: 113
taatacgact cactataggg agattcagtc aacatgtctt tccttggca             49

<210> SEQ ID NO 114
<211> LENGTH: 46
<212> TYPE: DNA
<213> ORGANISM: Artificial Sequence
<220> FEATURE:
<223> OTHER INFORMATION: Synthetic

<400> SEQUENCE: 114
taatacgact cactataggg agagtatctc ttggcaacgc cgtccc                46

<210> SEQ ID NO 115
<211> LENGTH: 44
<212> TYPE: DNA
<213> ORGANISM: Artificial Sequence
<220> FEATURE:
<223> OTHER INFORMATION: Synthetic

<400> SEQUENCE: 115
taatacgact cactataggg agaagaccac agccaagcct gtca                  44

<210> SEQ ID NO 116
<211> LENGTH: 43
<212> TYPE: DNA
<213> ORGANISM: Artificial Sequence
<220> FEATURE:
<223> OTHER INFORMATION: Synthetic -continued

```
<400> SEQUENCE: 116
taatacgact cactataggg agatcttctg acgcaccagc cgc          43

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
aattacactg taacttgcat gtaa                               24
```

INSECT-COMBATING PREPARATION AND METHOD BASED ON RNAI TECHNOLOGY

CROSS REFERENCE TO RELATED APPLICATIONS

This is a national stage application of PCT/CN2012/000333, filed on Mar. 19, 2012, which claims the priority of Chinese Application No. 201110067359.7, filed on Mar. 18, 2011. This application claims the benefit and priority of these prior applications and incorporates their disclosures be reference in their entirety.

TECHNICAL FIELD

The present invention relates to biotechnology and agriculture applications. More particularly, the present invention relates to RNAi-based target genes for the prevention of Lepidoptera pests, and describes direct applications of synthetic double stranded RNA preparations based on the target genes in the prevention of Lepidoptera pests in the fields.

BACKGROUND

Asian corn borers (*Ostrinia furnacalis* Guenée) are important agricultural pests in the world. They mainly damage economically important crops such as corns, sorghum, sunflowers, etc. Currently, the methods for preventing Asian corn borers still mainly rely on chemical prevention. However, chemical prevention causes enormous damages to the ecology and in the safe production of foods.

The myriad problems caused by chemical prevention forces us to search for better pest management methods. Although biological prevention can produce certain preventive effects, such effects are realized slowly and are not significant. In addition, biological prevention is more susceptible to environmental impacts and is not well accepted by the public. Transgenic plants can effectively prevent pest damages. However, after long-term cultivation of a transgenic plant, insect resistance to the pesticide effects of the transgenic crop can be induced, resulting in the increase of non-targeted pests. Furthermore, the safety of transgenic plants is still in dispute, limiting further development of such technology.

Since its discovery in 1991, the phenomenon of RNAi has seen rapid development. The studies show that using RNAi from specific gene, one can achieve directed interference of a target gene, resulting in certain physiological phenomenon to accomplish the studies of gene functions. In the meantime, such phenomenon is highly specific. That is, specific fragments of homologous genes can produce different interference in different species. Therefore, this is an ideal system for the control of pests.

Currently, there are reports of using RNAi technology to control insects. Baum et al. (2007) proved that v-ATPase has a lethal effect towards Western corn rootworm (WCR) (*Diabrotica virgifera* LeConte) and can be used to control WCR in the field. In the same year, Mao et al. introduced a P450 dsRNA into cotton, which can cause death of cotton bollworm (*Helicoverpa armigera*). Tian et al (2009) proved that death of beet armyworm (*Spodoptera exigua* Hübner) can be induced by feeding methods. These publications all show that RNAi technology as a new pest control method is feasible.

However, prior studies also show that RNAi based pest control still has some problems that need to be overcome, such as (1) how to discover target genes with fast, high throughput methods; (2) how to simplify the applications in field production; (3) resistance problems; (4) safety issues, etc. One would need to solve the above mentioned problems in order to use the RNAi technology to control pests. First, one would need to have sufficient and effective target genes so that a large number of target genes, in different combinations, can be used at different times to target different genes to achieve pest control, thereby avoiding the formation of resistant pests. Therefore, pest controls using RNAi technology hinges on solving two urgent problems: target gene identification and how to accomplish easy application in the fields. An object of the present invention is to solve these problems.

SUMMARY OF INVENTION

An object of the invention is to provide RNAi technology based pesticide preparations and methods of pest control.

In the first aspect of the invention, an isolated polypeptide is provided. The polypeptide is selected from the following:
 (a) a polypeptide having the amino acid sequence of any one of SEQ ID NO: 43-52;
 (b) a polypeptide derived from the polypeptide in (a), containing one or more (e.g., 1-20; preferably, 1-15; more preferably 1-10; more preferably 1-5; such as 3) amino acid substitutions, deletions or additions in the amino acid sequence of any one of SEQ ID NO: 43-52, and having the function of the polypeptide of (a).

In another aspect of the invention, an isolated polynucleotide is provided. The polynucleotide is selected from the following:
 (a) a polynucleotide encoding the polypeptide described above;
 (b) a polynucleotide complementary to the polynucleotide in (a).

In a preferred embodiment of the invention, the isolated polynucleotide is characterized in that it comprises a nucleotide sequence, wherein the nucleotide sequence is selected from the following:
 (a) a polynucleotide comprising the nucleotide sequence of any one of SEQ ID NO: 1-10, SEQ ID NO: 33-42, SEQ ID NO: 53-60, or a complementary sequence thereof;
 (b) a polynucleotide that can hybridize to the sequence defined in (a) under stringent conditions, or a complementary sequence thereof, wherein a dsRNA having at least one strand that is complementary to the polynucleotide, after being consumed by a pest, is capable of inhibiting the growth of the pest;
 (c) a polynucleotide that has a sequence identity with the sequence defined in (a) of at least 70% (preferably at least 75%, 80%, 85%, 90%, more preferably at least 95%, 96%, 97%, 98%, 99%), or a complementary sequence thereof, wherein a dsRNA having at least one strand that is complementary to the polynucleotide, after being consumed by a pest, is capable of inhibiting the growth of the pest;
 (d) a polynucleotide comprising a sequence of at least 17-21 consecutive nucleotides in the sequence defined in (a), or a complementary sequence thereof, wherein a dsRNA having at least one strand that is complementary to the polynucleotide, after being consumed by a pest, is capable of inhibiting the growth of the pest.

In another aspect of the invention, a vector is provided, wherein the vector contains one, two, or more of the above-described polynucleotides.

In another aspect of the invention, a genetically engineered host cell is provided. The host cell contains the above-described vector or its genome contains one, two, or more of the above-described polynucleotides.

In another aspect of the invention, applications of the above described polynucleotides are provided for the preparation of inhibition or silencing targets for interference molecules that can specifically interfere with pest gene expression or inhibit pest growth. The pest gene is selected from: LIM protein 1 gene, myoglobulin 3 light chain gene, chymotrypsin-like serine protease gene, chymotrypsin-like protease C1 gene, chymotrypsin-like serine proteinase C3 gene, hydroxybutyrate dehydrogenase gene, Kazal type serine proteinase inhibitor 1 gene, fatty acid binding protein 1 gene, and carboxypeptidase 4 gene.

In another aspect of the invention, nucleic acid inhibitors are provided. A nucleic acid inhibitor may be selected from:
(a) a dsRNA, antisense nucleic acid, small interference RNA, or miRNA to inhibit or silence a target from polynucleotide of claim 2 or 3, after being consumed by a pest, is capable of inhibiting the growth of the pest or
(b) a dsRNA, antisense nucleic acid, small interference RNA, or miRNA that uses a pest gene as an inhibition or silencing target. If a pest ingests the nucleic acid inhibitor, the growth of the pest would be inhibited. The pest gene is selected from: LIM protein 1 gene, myoglobulin 3 light chain gene, chymotrypsin-like serine protease gene, chymotrypsin-like protease C1 gene, chymotrypsin-like serine proteinase C3 gene, hydroxybutyrate dehydrogenase gene, Kazal type serine proteinase inhibitor 1 gene, fatty acid binding protein 1 gene, and carboxypeptidase 4 gene; or
(c) a construct that can express the dsRNA, antisense nucleic acid, small interference RNA, or microRNA described in (a) or (b).

In another preferred embodiment, the nucleic acid inhibitor is a dsRNA produced by expression of the polynucleotide. If a pest ingests the dsRNA, the growth of the pest is inhibited.

In another preferred embodiment, the dsRNA has a structure as follows:

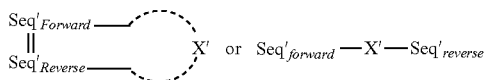

wherein

Seq'$_{Forward}$ is an RNA sequence, or a sequence fragment thereof, corresponding to any one of the polynucleotides described in claim 2 or 3, or contains an RNA sequence complementary to at least a portion of the polynucleotides described in claim 2 or 3;

Seq'$_{Reverse}$ is a sequence that is substantially complementary to Seq'$_{Forward}$;

X' is null or a spacer sequence between Seq'$_{Forward}$ and Seq'$_{Reverse}$, and the spacer sequence is not complementary to Seq'$_{Forward}$ or Seq'$_{Reverse}$;

|| indicates formation of hydrogen bonds between Seq'$_{Forward}$ and Seq'$_{Reverse}$.

In another preferred embodiment, the nucleic acid inhibitor is a construct that contains a structure as follows:

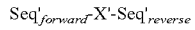

wherein

Seq'$_{Forward}$ is any one of the polynucleotides, or a fragment thereof, described in claim 2 or 3, or a nucleic acid sequence complementary to at least a portion of the polynucleotides described in claim 2 or 3;

Seq'$_{Reverse}$ is a sequence that is substantially complementary to Seq'$_{Forward}$;

X' is a spacer sequence between Seq'$_{Forward}$ and Seq'$_{Reverse}$, and the spacer sequence is not complementary to Seq'$_{Forward}$ or Seq'$_{Reverse}$;

|| indicates formation of hydrogen bonds between Seq'$_{Forward}$ and Seq'$_{Reverse}$.

In another aspect of the invention, a host cell is provided. The host cell comprises the above described nucleic acid inhibitor.

In another aspect of the invention, use of the nucleic acid inhibitor or the host cell is provided, wherein the use is for the manufacture of a preparation for pest control.

In another aspect of the invention, a preparation for pest control is provided; the preparation comprises a safe and effective amount of a substance selected from the following: said nucleic acid inhibitor or said host cell; and an agriculturally acceptable carrier.

In another preferred embodiment, the preparation further comprises at least one selected from the following pesticides: chemical pesticide, paratin, *Bacillus thuringiensis* pesticide protein, *xenorhabdus* pesticide protein, *photohabdus* bacteria pesticide protein, *Bacillus laterosporus* pesticide protein, and *Bacillus sphhaericus* pesticide protein.

In another aspect of the invention, a method for the control of pests is provided. The method interferes with pest gene expression. The pest gene is selected from: LIM protein 1 gene, myoglobulin 3 light chain gene, chymotrypsin-like serine protease gene, chymotrypsin-like protease C1 gene, chymotrypsin-like serine proteinase C3 gene, hydroxybutyrate dehydrogenase gene, Kazal type serine proteinase inhibitor 1 gene, fatty acid binding protein 1 gene, and carboxypeptidase 4 gene.

In another preferred embodiment, the method comprises: feeding and/or spraying a pest with a nucleic acid inhibitor according to any one of claims 7-10 or a host cell according to claim 5 or 11.

In another preferred embodiment of the invention, the method comprises: expressing in a plant an interference molecule that can specifically interfere with pest gene expression. The pest gene is selected from: LIM protein 1 gene, myoglobulin 3 light chain gene, chymotrypsin-like serine protease gene, chymotrypsin-like protease C1 gene, chymotrypsin-like serine proteinase C3 gene, hydroxybutyrate dehydrogenase gene, Kazal type serine proteinase inhibitor 1 gene, fatty acid binding protein 1 gene, and carboxypeptidase 4 gene.

In another preferred embodiment, the method comprises: introducing the nucleic acid inhibitor according to any one of claims 7-10 into the plant.

In another aspect of the invention, a plant or a seed thereof is provided. The plant is transformed with an above-described polynucleotide.

In another preferred embodiment, the polynucleotide is expressed in a plant as a dsRNA.

In another preferred embodiment, the pest is selected from: an insect, mite, fungus, yeast, mold, bacteria, nematode, weed and parasite, and saprophyte.

In another preferred embodiment, the pest is an insect pest, including, but not limited to: a Lepidoptera pest, a Coleoptera pest, a Hemiptera pest, and a Diptera pest.

In another preferred embodiment, the pest is selected from Lepidoptera pests, preferably a corn borer or a cotton bollworm.

Other aspects of the invention will be apparent to one skilled in the art based on this description.

BRIEF DESCRIPTION OF THE DRAWINGS

FIG. 1 shows results of bioassays of 10 genes. CK is a blank control, which is a cultured Asian corn borer.

FIG. 4 shows electrophoresis results of purified dsRNA synthesized in bacteria. The sizes of the positive electrophoresis bands in DS12 and DS28 are 400-500 bp.

FIG. 5 shows results from insect body wall penetration experiments using a fluorescence labeled DS12 dsRNA. The panels on the right (vertically arranged) are fluorescence locations on the insect using Cy3 dye and viewed with the corresponding wavelength. A: immediately after dropping the labeled sample on surface of the insect body; B: 1-2 hours after the labeled sample has penetrated into 2-3 segments in the insect body; C: 4-5 hours after the labeled sample has penetrated into the entire insect body.

FIG. 6 shows the lethal effects of cotton bollworm target gene dsRNA on cotton bollworm.

DETAILED DESCRIPTION

The inventors of the present invention, after extensive research, found some target genes (or their fragments) that can be used to control Lepidoptera insects. Based on these target gene nucleic acid sequences, nucleic acid inhibitors or host cells that expressing these nucleic acid inhibitors can be used to effectively kill Lepidoptera insects.

DEFINITION

In this description, the term "plant" does not have any specific limitation, as long as the plant is susceptible to pest (e.g., Lepidoptera insects) infestation, such as various crops, flowering plants, or forestry plants, etc. The plants, for example, may include (but are not limited to): dicotyledonous plants, monocotyledon plants, or gymnosperm plants. More specifically, the plants may include (by are not limited to): cotton, wheat, barley, rye, rice, corn, sorghum, beet, apple, pear, plum, peach, apricot, cherry, strawberry, raspberry, blackberry, bean, hyacinth bean, pea, soybean, rape, mustard, poppy, olive, sunflower, coconut, castor oil plant, cocoa bean, peanut, gourd, cucumber, watermelon, flax, hemp, jute, orange, lemon, grapefruit, spinach, lettuce, asparagus, cabbage, Chinese cabbage, pakchoi, carrot, onion, potato, tomato, green pepper, avocado, cinnamon, camphor, tobacco, nuts, coffee, eggplant, sugar cane, tea, pepper, grape vine, oyster linen, banana, rubber plant, and decorative plants.

In this description, the term "Lepidoptera insect" refers to any Lepidoptera insect, the genome of which contains a gene (or a fragment) of any one of SEQ ID NO: 1-10. Furthermore, these genes are essential for the growth or survival of the insects. The Lepidiptera insects include moths, specific examples of which include Tineidae and Oecophoridae (such as *Tneola bisselliella*, common clothe moth), and Pyralidae (such as *Pyralis farinalis*, Meal moth), etc.

In this description, the term "RNA interference or RNAi" refers to certain RNA that can efficiently and specifically block specific gene expression in vivo, stimulating mRNA degradation, inducing the cell to have phenotypes due to loss of specific genes. It can also be referred to as RNA intervention or interference. RNA interference refers to a highly specific gene silencing mechanism at the mRNA level.

In this description, the term "interference RNA" or "dsRNA" refers to an RNA molecule, which can use a homologous complementary sequence to target an mRNA to degrade a specific mRNA. This process is referred to as an RNA interference pathway.

In this description, the term "substantially complementary" refers to nucleic acid sequences that are sufficiently complementary and can interact with each other in a predictable manner, such as forming a secondary structure (e.g., a stem-and-loop structure). Normally, two "substantially complementary" nucleotide sequences have at least 70% nucleotides that are complementary; preferably, at least 80% nucleotides that are complementary; more preferably, at least 90% nucleotides are complementary; further preferred, at least 95% nucleotide are complementary, such as 98%, 99% or 100%. Generally, two sufficiently complementary molecules can have at most 7 unmatched nucleotides between them; preferably, at most 6 unmatched nucleotides between them; more preferably, at most 5 unmatched nucleotides between them; further preferred, at most 4 unmatched nucleotides between them, such as 0, 1, 2, 3, or 4 unmatched nucleotides.

In this description, the term "complementary" sequences refer to changing the sequence form 5'→3' direction to 3'→5' direction (e.g., 5'ATCG 3'→GCTA), and then obtain a complementary sequence (e.g., GCTA→5'CGAT 3').

In this description, the term "stem-and-loop" structure is also called "hair-pin" structure, which refers to a nucleic acid molecule that can form a secondary structure containing a double stranded region (stem), wherein the double stranded region is formed by two regions in the nucleic acid molecule (i.e., on the same molecule). Two regions each form one side of the double stranded region. The structure further comprises a "ring" structure, which comprises non-complementary nucleic acid molecule, i.e., single stranded region. Even if the two regions in the nucleic acid molecule are not completely complementary, the double stranded region can still maintain the double stranded condition. For example, insertion, deletion, substitution, etc. can lead to a small region that is not complementary or that small region may form a stem and loop on its own, or it forms a secondary structure in other manners. However, those two regions are still substantially complementary, and may interact with each other in a predictable manner to form a stem in a stem-and-loop structure. Stem-and-loop structures are well known to one skilled in the art. Normally, after obtaining a primary nucleic acid sequence, one skilled in the art can ascertain whether that particular nucleic acid can form a stem-and-loop structure.

In this description, the term "nucleic acid inhibitor" is a general term referring to a material prepared based on a target gene or a fragment thereof or a shortened form thereof, which is useful for controlling Lepidoptera insects according to the invention, and having an activity for controlling Lepidoptera insects. The nucleic acid inhibitors for example can be certain interference molecules, including dsRNA (also referred to as, double-stranded RNA, double-stranded ribonucleic acid, or double-stranded ribonucleic acid sequence), antisense nucleic acid, small interference RNA, micro RNA, or a construct that can form the dsRNA, antisense nucleic acid, small interference RNA, or micro RNA.

Figure 1:
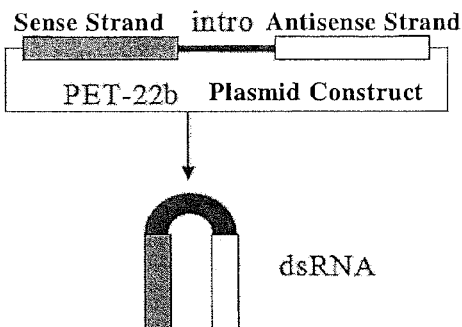
FIG. 1 shows schematic illustrating the synthesis of a dsRNA, wherein the internal sequence (intron) is 24 nucleotides long with a sequence of AATTACACTGTAACTTG-CATGTAA (SEQ ID NO: 117).

In this description, the term "operatably coupled" or "operatively coupled" refers to two or more nucleic acid regions or nucleic acid sequences are functionally arranged in space. For example, a promoter may be placed at a specific location relative to the target gene nucleic acid sequence such that the transcription of the nucleic acid is promoted by the promoter. Thus, the promoter region is said to be operatively coupled to the nucleic acid sequence.

In this description, "an RNA sequence corresponding to a DNA sequence" refers to an RNA sequence, wherein if the DNA sequence contains "AT", then the sequence is "AU" in the RNA sequence.

"Contain," "have," or "include" includes "comprise," "mainly consist of," "consist essentially of," and "consist of." "mainly consist of," "consist essentially of," and "consist of" are species in the genus of "contain," "have," or "include."

Gene

To search for target genes (or fragments thereof) useful in the control of Lepidoptera insects, the inventors carried out extensive research. After extensive research, the inventors found that the following genets are critical genes for insect development and growth and down regulation or inhibition of these gene expression can lead to growth problems or death in insects: LIM protein 1 gene, myoglobulin 3 light chain gene, chymotrypsin-like serine protease gene, chymotrypsin-like protease C1 gene, chymotrypsin-like serine proteinase C3 gene, hydroxybutyrate dehydrogenase gene, Kazal type serine proteinase inhibitor 1 gene, fatty acid binding protein 1 gene, and carboxypeptidase 4 gene.

Using the above described genes as targets for inhibition or silencing, one can prepare specific interference molecules to inhibit the growth of corn borers. This invention also provide genes from cotton bollworm that are highly homologous to the above-described genes as inhibition or silencing targets for the preparation of specific interference molecules to inhibit cotton bollworm growth. The above-described genes may also originate from other species. The functions of these genes have been documented in the literature; the nucleic acid sequences are highly homologous to those of corn borer. Therefore, it is predictable that these highly homologous genes can also be targets for the preparation of interference molecule to inhibit the growth of other species.

In this description, the term "highly homologous" or "high homology" when referring to a nucleic acid sequence, it means that the nucleic acid sequence can hybridize to corn borer genes SEQ ID NO: 43-52, or their complementary sequences, under stringent conditions. A sequence that can hybridize to corn borer genes SEQ ID NO: 43-52, or their complementary sequences, under stringent conditions, is a sequence that can form antiparallel pairing between the two sequences. Then, the two sequences can form hydrogen bonds between the bases on the opposite chains under stringent conditions to form a dimer, which is sufficiently stable under the stringent conditions and can be detected by methods known in the art. Preferably, these highly homologous sequences have sequences identities of about 65% to about 70% with any one sequences of the corn borer SEQ ID NO: 43-52, or their complementary sequences, or more preferably, about 80% to about 85% sequence identities, or more preferably, about 90% to about 95% sequence identities, to about 99% sequence identities.

Methods for confirming sequence identities are well known in the art, including using BLAST software and EMBOSS software (The European Molecular Biology Open Software Suite (2000), Rice, P. Longden, Land Bleasby, A. Trends in Genetics 16(6), pp. 276-277). In this description, the term "identity" refers to the relationship between sequences at the nucleic acid level. Two or more sequences, in the optimal alignments within a comparison window, are compared to confirm the identity percentage, wherein the portion of the sequences within the comparison window can have insertions or deletion, as compared with the optimally aligned reference sequence. The reference sequence does not include any insertion or deletion. The reference window is selected for at least 10 consecutive nucleic acids to about 50, about 100, or about 150 nucleic acids. Then, by identifying the number of nucleic acids that are identical between the sequences within the window, and divide this number by the total number of nucleic acid in the window, followed by multiplying it with 100 to calculate the identity percentages.

Among the above-described target genes, the inventors further studied target genes or their fragments that can be effectively down regulated. This leads to the identification of 10 target gene fragments, the nucleic acid sequences are selected from any one of SEQ ID NO: 1-10.

The fragments or shortened forms of the target genes (fragments) are within the scope of the invention, as long as these fragments or shortened forms can be used to prepare nucleic acid inhibitors having activities that can kill Lepidoptera insects.

The inventors unexpectedly discovered that these target gene fragments or their shortened forms play important roles in insect bodies. If they are inhibited, interfered with or silenced, it would lead to greatly reduced survival rates or directly lead to death of the insects. Therefore, one can design various nucleic acid inhibitors based on these target gene fragments in order to control pests.

This invention provides a polynucleotide set, wherein the polynucleotides comprise the sequences of SEQ ID NO: 1-10. When preparing nucleic acid inhibitors or its preparations for controlling Lepidoptera insects, one can obtain 1-10 polynucleotides from the polynucleotide set. One can based on multiple polynucleotide sequences (preferably, for example 10 sequences) to prepare nucleic acid inhibitors or host cells that express the nucleic acid inhibitors. When these sequences are used at the same time (or in combination), they can achieve broader spectrum and more effective control of Lepidoptera insects.

Nucleic Acid Inhibitors

Any material, prepared based on a target gene (fragment) or its fragment or shortened form provided in this invention and having activities for controlling Lepidoptera insects, can be nucleic acid inhibitors for use in controlling Lepidoptera insects. The nucleic acid inhibitors preferably are interference molecules, such as a dsRNA, antisense nucleic acid, small interference RNA, or micro RNA construct, or a construct that can express the dsRNA, antisense nucleic acid, small interference RNA, or micro RNA. More preferably, they are dsRNA or a construct that can express the dsRNA.

Based on the genes or their sequences provided by this invention, one can design a construct for expression of dsRNA, antisense nucleic acid, small interference RNA, or micro RNA. Therefore, the invention also provides artificial constructs. The constructs of the invention that are based on the genes or sequences disclosed in this description would be understood by one skilled in the art. Generally, the construct can include an internal sequence (not complementary to the flanking sequences on both sides) with complementary gene sequences attached to both ends of the internal sequence. After being introduced into a cell, this can form a "stem-and-loop" structure, and the "stem" portion forms dsRNA, antisense nucleic acid, small interference RNA, or micro RNA. These dsRNA, antisense nucleic acid, small interference RNA, or micro RNA can effectively inhibit the expression of the target genes.

In a preferred embodiment of the invention, the construction comprises at least one of the following structures:

$$Seq_{Forward}\text{-}X\text{-}Seq_{Reverse}$$

Wherein the nucleic acid sequence in $Seq_{Forward}$ is selected from any one of the sequences of fragments of SEQ ID NO: 1-10 and $Seq_{Forward}$ and $Seq_{Reverse}$ have substantially complementary nucleic acid sequences.

X is a spacer sequence located between $Seq_{Forward}$ and $Seq_{Reverse}$, and the spacer sequence is not complementary to $Seq_{Forward}$ or $Seq_{Reverse}$.

The formula I structure above can form the following secondary structure:

$$\begin{array}{c} Seq'_{Forward} \\ \| \\ Seq'_{Reverse} \end{array} \bigg) X'$$

The structure can be further cleaved, processed to form a double-stranded interference molecule to exert its gene silencing function.

The construct may be prepared to form one or more stem-and-loop structures. For example, it can contain 2 or more than 2 stem-and-loop structures.

Normally, the constructs are on expression vectors. Therefore, the invention includes a type of vectors, which comprise the described constructs. The expression vectors normally also contain promoters, transcription origins, and/or marker genes that are operatively coupled to the constructs. Methods known to one skilled in the art may be used to construct the expression vectors of the invention. These methods include in vitro recombinant DNA technology, DNA synthesis technology, in vivo recombination technology, etc. The expression vectors preferably comprise one or more selection marker genes to confer a characteristic that can be used to selected the transformed host cells. Examples of selection markers include kanamycin, gentamicin, hygromycin, and ampicillin resistance markers.

A vector containing an above-described gene sequence and an appropriate promoter or control sequence may be used to transform an appropriate host. In accordance with methods of the invention, the host may be any host that is suitable for carrying the expression vector and also can express the nucleic acid inhibitors. For example, the hosts may be *E. coli*, fungi, yeasts, plant cells, animal cells, etc.

The methods for transforming a host using a recombinant DNA can be any techniques known to one skilled in the art. An actual method used may depend on the type of plants. When a host is a prokaryote, such as *E. coli*, competent cells that are capable of intaking DNA may be harvested after exponential growth period and the transformation may use $CaCl_2$ treatment. The steps used in this transformation are commonly known in this field. Another method is to use $MgCl_2$. When necessary, one may also use electroporation. Transformation methods for yeast cells, plant cells, or animal cells are also well known to one skilled in the art.

A host cell carrying an above-described construct or an expression vector may be directly used on the target of protection (e.g., plants) to achieve the control of Lepidoptera insects.

The "stem" portion of a stem-and-loop structure is formed by interaction between $Seq_{Forward}$ and $Seq_{Reverse}$. The stems can be processed to produce nucleic acid inhibitors. The nucleic acid inhibitors may have the following structures:

$$\begin{array}{c} Seq'_{Forward} \\ \| \\ Seq'_{Reverse} \end{array} \bigg) X'$$

wherein $Seq_{Forward}$ is an RNA sequence or a fragment thereof corresponding to any one sequence of SEQ ID NO: 1-10 and $Seq_{Reverse}$ contains a sequence that is complementary to that of $Seq_{Forward}$. X' is a spacer sequence located between $Seq_{Forward}$ and $Seq_{Reverse}$. The spacer sequence is not complementary to $Seq_{Forward}$ or $Seq_{Reverse}$. The X' sequence may be removed in vitro or not removed. When dsRNA enters an insect body, it may be processed and removed by an enzyme (e.g., nucleic acid enzyme, Dicer) in the insect.

The nucleic acid inhibitors may be directly used on targets needing prevention (e.g., plants) to achieve the purpose of controlling Lepidoptera insects.

Transgenic Plants

The invention relates to methods for improving pest resistance in plants. A method of the invention comprises introducing a nucleic acid inhibitor into a plant. Plant transgenic techniques are well known to one skilled in the art, such as *Agrobacterium tumefaciens* transformation techniques or gene gun transformation techniques, etc., and also leaf-disc method, embryo transformation methods, etc. A transformed plant cell, tissue or organ can be regrown into a plant using regular methods to produce pest resistant plants.

Preferably, a method for improving pest resistance in a plant comprises:

(1) providing an *Agrobacterium tumefaciens* carrying an expression vector, the expression vector comprises an above-described nucleic acid inhibitor;

(2) contacting a plant cell, tissue, or organ with the *Agrobacterium tumefaciens* of step (1) to transform the nucleic acid inhibitor into the plant cell, tissue, or organ;

(3) selecting the plant cell, tissue, or organ that has been transformed with the nucleic acid inhibitor; and (4) regenerating a plant using the plant cell, tissue, or organ from step (3).

The described method may be carried out using any appropriate regular means, including reagents, temperatures, pressure conditions.

Currently, using plants as a medium, to inhibit insect growth or kill insects by feeding insects with nucleic acid inhibitors (interference molecules) that can interfere with insect gene expression is well known to one skilled in the art. For example, Ying-Bo Mao, et al., "*Silencing a cotton bollworm P450 monooxygenase gene by plant-mediated RNAi impairs larval tolerance of gossypol*," Nature Biotechnology, Vol. 25, No. 11, November 2007, proves the effectiveness of these methods.

Compositions and Methods for Controlling Lepidoptera Insects

The invention provides a preparation (e.g., a pesticide composition), which comprises a safe and effective amount of a construct, a host (cell) carrying an expression vector capable of expression nucleic acid inhibitors, or a nucleic acid inhibitor (e.g., 20-500 µg/ml); and an agriculturally acceptable carrier.

In this description, the term "comprise" refers to various components may be used in a mixture or composition of the invention. Therefore, the term "mainly consist of" and "consist of" are included in "comprise."

In the present invention, an "agriculturally acceptable" component refers to a material that is suitable for use in agriculture and has a reasonable benefit/risk ratio without posing excessive adverse effects (e.g., toxicity, irritation, and allergic reaction) to human, animal (except Lepidoptera insects), or plants.

In the present invention, an "agriculturally acceptable carrier" is a solvent, a suspending agent, or an excipient used to deliver a construct or a host cell that carries an expression vector capable of expression a nucleic acid inhibitor, or a nucleic acid inhibitor of the invention to a Lepidoptera insect. An agriculturally acceptable carrier can be a liquid or a solid; preferably it is a carrier that can preserve the activities of the hosts or the nucleic acid inhibitors.

The preparations (or agricultural compositions) may be in various dosage forms, including (but not limited to): aqueous solution, suspension, wettable powder, emulsifiable concentrate, lotion, a spray solution, aqueous dispersion, powder, granule, or microcapsule. It should be understood that as long as it can deliver a construct or a host cell that carries an expression vector capable of expression a nucleic acid inhibitor, or a nucleic acid inhibitor of the invention to a Lepidoptera insect, while preserving all or part of the activities. Preferably, a dosage form is that which is easy to deliver. For example, an agricultural composition may be a liquid spraying agent or a nebulizing agent.

In the present invention, an adjuvant is an auxiliary component, which has an auxiliary regulation function in a composition. For example, it may be a surfactant, adhesion promoter, or other auxiliary agent.

In agricultural composition concentrates, the active ingredients (i.e., a host carrying a construct or an expression vector that can expression a nucleic acid inhibitor, or a nucleic acid inhibitor of the invention) are present at high concentrations. For example, a concentration may contain nucleic acid inhibitors at 200-500 µg/ml, and application dosage is 50-1000 µl/300-500 heads. Alternatively, based on the contents of the host carrying a construct or an expression vector that can expression a nucleic acid inhibitor, or a nucleic acid inhibitor of the invention, and with reference to the application dosage of the nucleic acid inhibitor, to apply a certain amount of the host (cell). In addition, a composition concentrate can also contain other suitable common components: chemical agent, synergistic agent, trace element, stabilizer, adhesion agent, wetting agent, dispersion agent, surface active agent, permeate agent, tanning agent, solvent, filler, etc. An agricultural composition of the invention may further comprise other active insecticides or microbicides.

In preparing an agricultural composition, a suitable solid diluent may include, but not limited to: clay, such as diatomaceous earth, corn husk, tricalcium phosphate, cork powder, kaolin, betonies, or attapulgite etc., and a water soluble polymer.

In addition, solid compositions may also include one or more compatible wetting agents, dispersion agents, surface active agents, or coloring agents. These components may also function as a diluents in solid forms.

These solid compositions may be powders, granules, or wettable powder dosages. Generally, powders are obtained by grinding, and granular forms, tablet forms or brick forms may be obtained from granules.

Liquid compositions may be in the form of solutions, suspensions or emulsions. They may be enclosed by natural or synthetic polymers, and may include wetting agents, dispersion agents or surface active agents. Such locations, suspensions or solutions may use aqueous, organic, or water-organic diluents to prepare water soluble polymer (and a mixture of the above diluents). In addition, the diluents may include, for example, ionic or non-ionic wetting agents, dispersion agents, or emulsifiers, or their mixtures.

The principles for the various preparations are known and are described, for example, in the following publications: Winnacker-Kuchler, "Chemische Technologie," Vol. 7, C. Hauser Verlag Munich, $4^{th}$ Ed., 1996; van Valkenburg, "Pesticide Formulation," Marcel Dekker, N.Y., second edition, 1972-73; K. Martens, "Spray Drying Handbook," the third edition, G. Goodwin, Ltd., London.

The auxiliary agents (such as inert substances, surfactants, solvents and other additives) for the preparation of compositions of the invention are known in the art and described in, for example: Watkins "Hand-book of insecticide Dust Diluents and Carriers", 2nd, Ed., Darland Books, Caldwell N.J.; H. v. Olphen, "An Introduction to Clay Colloid Chemistry," 2nd Edition, John Wiley & Sons, New York, 1977., Marsden, "Solvent Guide" 2nd Ed., Interscience, N.Y. 1950; McCutcheon's, "Detergents andEmulsifiers Annual", MC Publ. Corp., Ridgewood N. J.; Sisley 和 Wood, "Encyclopedia of Surface Active Agents", Chem. Publ. Co. Inc., N.Y. 1964; Schonfelt, "Grenzflachenaktive Athylenoxidaddukte," Wiss. Verlagsgesell., Stuttgart 1976; Winnacker-Kuchler, "Chemische Technologie," Vol. 7, C. Hauser Verlag Munich, 4th Ed., 1986.

Wettable powder can evenly distribute in water. In addition to surface active agents, wettable powders can also include wetting agents, dispersion agents, diluents, etc. that are not environmentally harmful substances. Preparation of powder formulations may comprise: grinding a surface active agent with a natural clay or diatomaceous earth solid substance such as talc, kaolin, betonies, etc. Granular formulation can be prepared by spraying active ingredient to allow it to adsorb on inert substance particles, or apply the active ingredient on the surface of a carrier (such as sand, kaolin, or inert substance granules) with aid of an adhesive agent (such as polyvinyl alcohol, sodium polyacrylate, or mineral oil). If used with a fertilizer, the active ingredient may be prepared in granules as in the preparation of fertilizer granules.

As for controlling insect attach of plants, delivering dsRNA that is for insect control to the plant surfaces by spraying application is an alternative method for protecting the plants. Under this condition, genetic engineered bacteria for producing and accumulating dsRNA may be fermented, and the fermentation products may be formulated as a spray that is compatible with commonly used agriculture application. The formulation may comprise: a colloidal agent and wetting agent for highly efficient covering of leaves, and a protective agent for protecting dsRNA from UV damages. These additives are commonly used in biocide insecticide industries, and are well known to one skilled in the art. Similarly, for application in soils, the formulations can include the following granular formulations, larvae baits for use to control soil pests (such as, corn rootworm).

Wherein the bacteria or yeast cells are killed, such as through heat treatment or mechanical treatment.

The inventors accidentally discovered that the nucleic acid inhibitors may enter the insect body by permeation. Therefore, one can use various nucleic acid inhibitors or compositions comprising various nucleic acid inhibitors to apply on insects to achieve control of the insects. The application methods can include, but are not limited to, spraying, spread, or dropping onto insect body surface. The nucleic acid inhibitors may be selected from: dsRNA, antisense RNA, small interference RNA, micro RNA; or a construct capable of expressing the dsRNA, antisense RNA, small interference RNA, micro RNA.

This invention provides a method for the control of Lepidoptera insects. The method comprises: applying a host carrying a construct or expression vector for expressing a nucleic acid inhibitor or the nucleic acid inhibitor on to the target (e.g., plants, especially, plants that are susceptible to Lepidoptera insects; or insect itself).

In addition, it is also possible to directly use the nucleic acid inhibitors, an agricultural composition comprising the nucleic acid inhibitors, or a host capable of expressing the nucleic acid inhibitors to feed insects or to spray insects. The agricultural compositions may be prepared as a spray formulation for direct spraying to control pests.

This invention addresses the problems in Lepidoptera insect controls. Based on RNAi technology, 10 fragments of target genes that can be used in field prevention and control have been developed. It is proven that inhibiting gene expression by nucleic acid inhibitors, using a simple method of spraying, is effective, leading to death of Lepidoptera insects, thereby achieving the control purpose. The methods are convenient, fast, accurate, and do not cause any pollution.

Advantages of the Invention Include (1) This invention discloses 10 target genes for the control of Lepidoptera insects for the first time, and proves that nucleic acid inhibitors based on these target genes can be directly applied in pest control. The pest control methods are convenient, fast, accurate, and can solved the problems faced by currently pest control: resistance and environmental incompatibility.

(2) RNAi technology is a new pest control technique that is efficient, specific control, and non-polluting. The dsRNA obtained can be directly applied in the field for pest control.

(3) There are a large number of target genes for screening. By random replacement of the target genes or mixed use of the target genes, it is possible to avoid occurrence of resistance in the target pests.

(4) It is possible to select target genes specific for a particular species, thereby minimizing the impact on non-target.

(5) the R&D costs are low, and can be rapidly move to production.

(6) The methods are convenient and have good environmental compatibility.

In the following, the invention will be further explained using examples. It should be understood that these examples are for illustration of the invention and are not intended to limit the scope of the invention. In the following experimental methods, the conditions not specified are as those commonly used in the art, such as those described in Sambrook et al., Molecular Cloning: A Laboratory Guide, (New York: Cold Spring Harbor Laboratory Press), or those suggested by the manufacturers.

Unless specifically defined, the scientific terms and terms in the art are used as understood by those skilled in the art. In addition, any methods or materials that are equivalent to those described herein may also be used in this invention. The preferred examples of methods and materials described here are for illustration only.

Example 1: Cloning of a Full Length Target Gene from Corn Borer and Target Gene Fragments Information The inventors screened and selected 10 target genes from a large number of genes (Wang et al., PLoS ONE, 6(4): e18644; and Chinese Invention Patent 201010197328.9). The sequences and inform of these gene fragments are shown in TABLE 1. The temporary names of the proteins encoded by these genes are shown in TABLE 2.

TABLE 1

| Name | SEQ ID NO: | Sequence |
|---|---|---|
| DS2 | 1 | TATCTTCGCCCTGTACTGTAATACGCGTTCGGGAGCTCGACTCTCGTAGCGACTCGACGAACAGGATAA GTTAAGCGAGCACAATGCCTTTCAAACCAGCAGACAACCCCAAGTGTCCGAAATGCGGCAAGTCCGTAT ACGCAGCCGAGGAGAGAGTAGCCGGTGGACTGAAGTGGCACAAGATGTGCTTCAAGTGCGGACTGTGC CAGAAGTTGCTGGACTCCACCAACTGCTCAGAACACGAAGGTGAACTGTTCTGCAAAGTATGCCACGC GCGCAAGTTCGGTCCCAAGGGCTACGGCTTCGGCGGTGGCGCTGGCTGCCTTTCCATGGACGCTGGTG AACACCTGAAGGCTGAAGATGCGAATTGAGCGCGAGCAGCCATCCAGCAGAGCTAGCGGGTCGCTC TCCCTATAGTGGGTTCGTAAATAAA |
| DS3 | 2 | CCATCCATGTTCTCACAGAAGCAGGTCGCCGAATTCAAGGAGGCCTTCCAGCTAATGGA CCACGACAAGGACGGTATCATCGGCAAGAACGACCTCCGCGCCACCTTCGACTCGCTCGGC AGGCTGGCGTCCGAGAAGGAGCTGGACGAGATGGTGAACGAGGCCCCCGGCCCCATCA ACTTCACGCAGCTGCTGACCCTCTTCGCCAACCGCATGTCCGGCGGCTCCGACGAGGACGA CGTCGTCATCAACGCCTTCAAGACCTTCGACGAGGAGGGCAAGATCGACTCCGAGAGGCT CAGGCACGCGCTCATGACCTGGGGAGACAAGTTCTCCGCCGACGAGGTCGACGAGGCCTA CGACCAGATGGAAATCGACGACAAGGGCTTCATCGACACCACCAAGCTCATCACCATGCTG ACCGCCGCCGCTGAGGAGGACGAGGGCGGCGAAGCTGCGTAGTTCCACCCGCGCCAGT CTCCCTATAGTAG |
| DS5 | 3 | TGCGGCAGTTCGCTGGTCAGCAACACGCGCTCGGTGACGGCGGCTCACTGCTGGCGCACCAGCACC TTGCAGGCGACCATGTTCACCATCGTGTGGAACTCTAACTCTATATTCTGGGGCGGCACGCGCATA AACACCAACCAGGTCATAGAGCACCCGAATTACAACGTGTGGAACTTGAACAACGATGTGGCCGT |

TABLE 1-continued

| SEQ ID |  |  |
|---|---|---|
| Name | NO: | Sequence |
|  |  | CATCATACACAACCACGTAAATTTCAACAATAATATCCAGCCAATTGCCCTGGCCACTGGCTCGC<br>AAACCTACGCGGGAACCTGGGCAGTCGCTGCTGGATACGGCCAGACTGGCGATGGTAATTCACCG<br>TCTGGCACTAAGTTCCAAGCCAATCTGCTGGTGATCACCAACTCAGCGTGCCAGGGAACCTGGATG<br>CCCGGCATCGTCATCGCGTCCA |
| DS6 | 4 | GTCAGAGTCAGGGCTGGCGGTCCCATCTCCGCTCAGCTCCTCGAGTTGACCGTGACCACCATCTCT<br>GGCGATCAGTGCGTGCGCGACGTGGCCCAGGCCTCCGTCGACTTCAACGTCGCCGCCCCACCGGTG<br>GAACCCCACGTCGAGCTCTGCATCATCCACTCGCCGAACCACGGCATGTGCAACGGTGACTCCGGC<br>AGCGCTCTAGTCCGCTGGACCGCGGCACCCAGATCGGAATCGTGTCGTGGGGCTTCCCCTGCGCC<br>CGCGGCGCTCCCGATATGTTCGTCCGAGTCAGCGCCTTCCAAGACTGGGTCGCCCGCCACTTCGTT<br>GCTTGTCTCCCTATAGTGAGTCGTATTAA |
| DS10 | 5 | ACCGGGTCGTGCTCGGCTCCACACTATCTTCAGCGGTGGTGTCCGTCAAACCACCTCTGACATTGTC<br>ATGCACCCACAGTGGACCCCGGAGACCGTTGCTAATGACATTGCCGTCATTAGGATTAACGCTGTTAC<br>TTTCACCAATGTGATCCAGCCCATCTCTCTGCCCAGCGGATCTCAGCTAAATAACAACTTCGTAGGCC<br>AGGTCGGAATTGCTTCTGGATTCGGACGCACTTCTGATGGTGCTAACATCCCGAACAACCAACTC<br>GTGAGCTGGGTGAGAGTGCCGATCATCACCAACCAGGCGTGCGCCTCAGTCTTCGGACCCTTCAT<br>CTTAAGTAGCACCATCTGCACCAACGGCTCTGGTGGTATGGGCACGTGCCAGGGAGACTCTGGTG<br>GTCCTCTCGCTGTGGAAGTTGGCAACTCTAGGGTCTTGGTTGGTGTGACTTCCTTTGGTGCTGCTGC<br>CGGTCTCCCTATAGTGAGTCCGTAATAAA |
| DS12 | 6 | TTGCCATCGTTGGAGAACGCAGCCAAACTAAAAGATGTTACGGAAAGTATCTCGAAGGTCGGTA<br>ACAAGCCTCTTGTGATCACCGCCGATGTTACCAAAGAAAGTGATGCTCAAAGAATCATCAACGA<br>TACAGTAAAACATTTTGGAAAACTTGACATTCTTGTCAACAATGCAGGAGTGGGTGGCAATGCC<br>AGCATTACTGAAGCAGAAGCCATGACAACATTTGACCATATCATGAATACCAACCTGCGTTC<br>CGCTGTCTACATGACCAATCTGGCTGCCAAGCATCTTATTGAAACGAAAGGGAATGTAATAAA<br>CATATCAAGCGTTGCTGGTCAAATGGTGATGGAAAAAGGGTTTGCTTACTGCACCTCAAAA<br>GCTGCCTTGGATCATTTCGCGAGATCAATACGTTGGACTTTGCGCCACATGGTGTTCGCGTGA<br>ACAACATTAGCCCTGGGCCGGTGAGGTCTCCCTATAGTAGTCGTATTAA |
| DS28 | 7 | AAGAACCATGCCGATCAGCTGATCAGTGCCCACGTCCAGCAGTGGGAACCACGGCAGGAGGGT<br>GTCAGACCTGCACTCGGTGGCGGTTGTCATGTTGTAGTAGTAGTGGCGACCCATGAGAATAAT<br>GCAAGCTTGTTTGGTGAAATGGGTGGTGGCGGTGTCGGTGACCTCGTTGGCGTTGCCGGAGA<br>TCCTCATCAGGTCTCCGTTGAAGCCGGTGACCCACACAGCATTCTCCTGCAGTACGCGGCCTGC<br>CACGCGGGAGGCGCGGCGCTCCTCCTTGCTCTTCTTCAATGTGGCTTCAGAAACGAAGTAT<br>TGCTGCAAGGTCCAGTAATTCCTAACTTGTCCATTAGAGTTTGCCGGTGCAGTCCAGTACGTG<br>TAGCCTTGGGTAGCCCAGTCCAAGACAGCGCCGTCTCCCTATAGTGAGTCGTATTAA |
| DS30 | 8 | CCGCGCAGCGTCGCCCCGCGTCCTACTTTACTAAACTTGGAAGGTGCAAACAGTTCATCTAC<br>GGAGGATGTGACGGCAACGGCAACCGTTACAACACTCTAGAGGAGTGTCAGGCTGCTTG<br>CGAGAGTGACTGCAACAAATAATAACGAAATGCAAGCAATCAATTGGGTATTTGACAGC<br>ACAGTCAATTGACATACTTTTTTATACTGTCAAAACGCACCATTCCCTATTTTTCACATT<br>TTGCAAAGTAGAGGGAATCTAAAGGCCATAGCAGACTTATCAACTCGGAAAGGGATCA<br>TACCGTATCGCCGTTCGCGAGCTATCATCGCCTTTCGCGCGCTGTCAACTGTCAACCGCGA<br>GGCGAGGCGTTTACGTTACTGTGCGGATAAGTGTGGGTTACAGTATGGAATTTCACACTGA<br>TCGCATCAATTTAATACGGTTACAATCCCTGTCCGGGTTGAAAAGTGGGCCCTCCCAAT<br>AGGGAGCCGAATAAA |
| DS34 | 9 | GGGCCTTCATGCAGTACAAGCCGAACCAGATCCTCGAGAAGAACGGGGACTCCTACAAGCTGA<br>TCTTCAAGACCCCCGCCCTGAACCACGAGGTGGTGTTCAAGTCTGGAGTGCCTTACA<br>GCGACGTCATCCGTGAAGGTTTGACGGCTGAATCCACCATCACCGTCGATGGAGACACC<br>TTCACTCAGGTCCAGGACTACGGCCCCCTTGGCTCCATCACCTTCAAGAGAGTACAGCG<br>CCGACCAACTTAAAGTGACTGTCACCAGCAGTAAATGGGATGGCGTTGCCTACAGATCTCC<br>CTATAGTGAGTCGTATTAA |
| DS35 | 10 | AAAGGGGCCCGCCCCATCAAGTACCTGAAGATATCCACCACCAACTTCCAAGCACCAGCA<br>AGCCTGTCATCTTCATTGACGGAGGCATCCACTCCAGGGAATGGATCTCACCACCCACCG<br>TCACTTGGGCGATCAGGAAACTGGTGGAAGATGTCACCGAACCTGACCTCCTGGAGAGGTT<br>CGACTGGATACTCTTGCCTATCGTCAACCCTGACGGTTATGAACACGCCACACATCTAAC<br>CGTTTCTGAGGAAGACACGTTCGGCTACCAGCATTGCATTATGCCGAGGAGTTGATGGCAA<br>CCGCAACTACGACTTCGCATGGAACACCGTCGGAACCAGCACCAACCCTTGCTCCGACACT<br>TATGGAGGCCCTACAGCCTTCTCCGAAATCGAGACCAGGGTTGTTCGTGACATCCTCCACGA<br>GAACCTCAGCAGAATGGCTCTGTACCTCACCATGCATAGCTTTGGTAGCATGATCCTGTACC<br>CTTGGGGACATGATGGTTCTTTATCCAACAACGCATTTGCACTCCAGACCGTTCTCCCTATAG<br>TGAGTCGTATTAAAA |

TABLE 2

| Name | Name |
|---|---|
| DS2 | LIM Protein 1 |
| DS3 | myosin3 light chain |
| DS5 | chymotrypsin-like serine protease |

TABLE 2-continued

| Name | Name |
|---|---|
| DS6 | chymotrypsin-like protease C1 |
| DS10 | chymotrypsin-like serine proteinase C3 |
| DS12 | Hydroxybutyrate dehydrogenase |

TABLE 2-continued

| Name | Name |
|------|------|
| DS28 | Protein of unknown function |
| DS30 | Kazal-type serine proteinase inhibitor1 |
| DS34 | Fattyacid-bindingprotein1 |
| DS35 | carboxypeptidase 4 |

Full length target genes were cloned based on the target gene fragments shown in TABLE 1, using the following method:

1. Extraction of Asian corn borer total RNA;

Asian corn borer 3 instar larvae are used as the starting materials. The RNA was extracted using the regular Trizol method, and purified using the regular purification method. The RNA sample was treated with DNase. This afforded an RNA sample with a concentration of ≥300 ng/μl, a total yield of ≥6 μg, OD260/280 1.8-2.2.

2. mRNA isolation and cDNA synthesis

The polyA containing mRNA was isolated with oligo-dT magnetic beads. Then, the first strand of cDNA was synthesized using random hexamer primers and the Superscript II reverse transcriptase reagent kit from Invitrogen.

3. Gene amplification and sequence determination.

Using specific primers for the full length target genes shown in TABLE 5, the desired genes are cloned with RACE cloning. The RACE reactions are performed according to the instructions in the reagent box (SMARTer RACE cDNA Amplification Kit). The amplified products were analyzed on 1% agarose gel electrophoresis, and the target fragments were collected. The collected gene fragments were purified, ligated into pMD18-T vector (Takara), and transfected into E. coli strain Top10. After blue-white selection, the positive strains were subjected to sequence determination.

TABLE 5

Primers for RACE of 10 target genes from corn borer

| | 3'RACE | |
|---|---|---|
| | F1 (SEQ ID NO:) | F2 (SEQ ID NO:) |
| DS2 | TTCGGCGGTGGCGCTGGCTGCCTTTC (61) | GCGGTGCCTCGCGAACGCACGCCATA (71) |
| DS3 | TTCGCCAACCGCATGTCCGGCGGCTC (62) | GGACGAGGGCGGCGAAGCTGCGTAGT (72) |
| DS5 | CGGCACGCGCATAAACACCAA (63) | GCCGTCGGCTCCGGCAACAACAGGCA (73) |
| DS6 | TGCGCCCGCGGCGCTCCCGATATGTT (64) | ACTGGGTCGCCCGCCACTTCGTTGCT (74) |
| DS10 | ACCAGGCGTGCGCCTCAGTCTTCGGA (65) | TGCTGCTGCCGGTTGCCAAGCTGGAT (75) |
| DS12 | CGCTGGAGAGGGAGCGAACGTTGCCA (66) | AATCGCGTTGGACTTTGCGCC (76) |
| DS28 | CCGACACCGCCACCACCCACTTCACC (67) | TTGGCCAGCTGCCCGCTAACGCCCTC (77) |
| DS30 | ACCGGACCATGCAGAGGCGGGAAGGT (68) | CAACTGTCAACTGCGAGGCGAGGCGT (78) |
| DS34 | ATCTTCAAGACCCCCGCCCTGA (69) | GGTCCAGGACTACGGCCCCCTTGGCT (79) |
| DS35 | TCGAAGGCCGCCCCATCAAGTA (70) | ACACGTTCGGCCACCAGCATT (80) |

| | 5' RACE | |
|---|---|---|
| | R1 (SEQ ID NO:) | R2 (SEQ ID NO:) |
| DS2 | AGTCCAGCAACTTCTGGCACAGTCCGCA (81) | ACCGGCTACTCTCTCCTCGGCTGCGT (91) |
| DS3 | AGCTGCGTGAAGTTGATCGGGC (82) | TCGGCGACCTGCTTCTGTGAGA (92) |
| DS5 | TGGTGTTTATGCGCGTGCCGCCCCAG (83) | CCGCCCCAGATCCTGCCGCCATCGAA (93) |
| DS6 | ACGCCACGCACGCACTGATCGCCGGA (84) | ACCGCCGGCCCTGATTCTGCCCCAACCA (94) |
| DS10 | AACGGTCGCCGGGGTCCACTGAGGGT (85) | CCGTCATGGTGGCAGTGCGCAGCGGT (95) |
| DS12 | ATCGGTCCTCACCGGCCCAGGGCTAA (86) | GCGAACACCATGTGGCGCAAA (96) |
| DS28 | GCGCCGGGGTAACTATCAGGGGGCA (87) | TGCTCAGGGGGCCATCGGGTCTTGGGGT (97) |
| DS30 | GCAGTCACTCTCGCAAGCAGCCTGACAC (88) | GTGCAGTCTGGGGCTGGGGCGTCACT (98) |
| DS34 | CGGATGACGTCGCTGTAAGGCA (89) | ACCACCTCGTGGTTCAGGGCGGGGT (99) |
| DS35 | AGTCGTAGTTGCGGTTGCCGT (90) | TCCTGATCGCCCAAGTGACAGTGGGTGG (100) |

The cDNA sequences of the cloned, full-length target genes are as follows:

>DS2, 612 bp cDNA Sequence
(SEQ ID NO: 33)
GGATTCGACCTCCGCGCACCGCAGTCTCGGCATCTTCGCCCTGTACTGTAATACGCGTTCGGGAGCTCGACTCTCGTAGCGACTCGACG AACAGGATAAGTTAAGCGAGCACAATGCCTTTCAAACCAGCAGACAACCCCAAGTGTCCGAAATGCGGCAAGTCCGTATACGCAGCCGAGGA GAGAGTAGCCGGTGGACTGAAGTGGCACAAGATGTGCTTCAAGTGCGGACTGTGCCAGAAGTTGCTGGACTCCACCAACTGCTCAGAACACG AAGGTGAACTGTTCTGCAAAGTATGCCACGCGCGCAAGTTCGGTCCCAAGGGCTACGGCTTCGGCGGTGGCGCTGGCTGCCTTTCCATGGAC GCTGGTGAACACCTGAAGGCTGAAGATGCGAATTGAGCGCGAGCAGCCATCCAGCAGAGCTAGCGGGTCGCCGACACACATCTCGGCCAACC AGCGGTGCCTCGCGAACGCACGCCATACTGTACTTTAATTACTTTAGTTAGGGTTATTTATTCGCTATTGCTTAATTTATTTTGTTTATCGG

AACAATATTTATAATTTATACAAAATCCAATAAAAGAGTCGACTACCAACAAAAAAAAAAAAA

>DS2, 95 aa
(SEQ ID NO: 43)
MPFKPADNPKCPKCGKSVYAAEERVAGGLKWHKMCFKCGLCQKLLDSTNCSEHEGELFCKVCHARKFGPKGYGEGGGAGCLSMDAGEHL

KAEDAN

>DS3, 819 bp cDNA Sequence
(SEQ ID NO: 34)
GGGACTGCCGTCGAGCACAGTCTCTCCTTCGTCGATCGTCCAACACACAACACAATGGCGGATAAGGATAAGAAAGTAAAGAAGAAGAA GGCGAAAGAAGATGCGCCAGCTGAGGAGGCGCCCGCACCAGCGGCGCCCGCAGCCAGCGGCGGCAGCGAGAGGCAATCCTCCCGCGGCAGCC GCAAGGCCAAGCGCACCGGCTCCAACGTCTTCTCCATGTTCTCACAGAAGCAGGTCGCCGAATTCAAGGAGGCCTTCCAGCTAATGGACCAC GACAAGGACGGCATCATCGGCAAGAACGACCTCCGCGCCACCTTCGACTCGCTCGGCAGGCTGGCGTCCGAGAAGGAGCTGGACGAGATGGT GAACGAGGCCCCCGGCCCGATCAACTTCACGCAGCTGCTGACCCTCTTCGCCAACCGCATGTCCGGCGGCTCCGACGAGGACGACGTCGTCA TCAACGCCTTCAAGACCTTCGACGAGGAGGGCAAGATCGACTCCGAGAGGCTCAGGCACGCGCTCATGACCTGGGGAGACAAGTTCTCCGCC GACGAGGTCGACGAGGCGTACGACCAGATGGAAATCGACGACAAGGGCTTCATCGACACCACCAAGCTCATCACCATGCTGACCGCCGCCGC GGAGGAGGACGAGGGCGGCGAAGCTGCGTAGTTCCACCCGCGCCAGTCTCCGCCCGACCCGCGGTTCGCAACATCTAGAACCGACTTTTTAT TATAATTTCTATATGTAATTTATTGTTTCCATTTTTTTATTTATATATAATGAAAATATAGTTCTACTATTACCAAAAAAAAAAAA >DS3, 205 aa
(SEQ ID NO: 44)
MADKDKKVKKKKAKEDAPAEEAPAPAAPAASGGSERQSSRGSRKAKRTGSNVFSMFSQKQVAEFKEAFQLMDHDKDGIIGKNDLRATFD SLGRLASEKELDEMVNEAPGPINFTQLLTLFANRMSGGSDEDDVVINAFKTFDEEGKIDSERLRHALMTWGDKFSADEVDEAYDQMEIDDKG

FIDTTKLITMLTAAAEEDEGGEAA

>DS5, 938 bp cDNA Sequence
(SEQ ID NO: 35)
GCACGAGGGCCGTCCAATGAAGTCAATGAAGTCAATGAAGTCGTCCCTCTTGTTCCTGTTGGTGGTGGCGGTGGCGGCGGCGGAGCTGC TGCAGCCCAACACGCGCTACCACGAGACCGAGGGCATCCCGAAGTTCCAGCTGATGAAGCAGCTGGAGGAGGGAACCGACTTCGATGGCGGC AGGATCTGGGGCGGGCAGGCCGTCAGCGGCGGTACCCATCCTCACCTGGGAGGACTGTGGATCACCCTGACCACTGGACAGAACTCGATCTG CGGCAGTTCGCTGGTCAGCAACACGCGCTCGGTGACGGCGGCTCACTGCTGGCGCACCAGCACCTTGCAGGCGACCATGTTCACCATCGTGT GGAACTCTAACTCTATATTCTGGGCGGCACGCGCATAAACACCAACCAGGTCATAGAGCACCCGAATTACAACGTGTGGAACTTGAACAAC GATGTGGCCGTCATCATACACAACCACGTAAATTTCAACAATAATATCCAGCCAATTGCCCTGGCCACTGGCTCGCAAACCTACGCGGGAAC CTGGGCAGTCGCTGCTGGATACGGCCAGACTGGCGATGGTAATTCACCGTCTGGCACTAAGTTCCAAGCCAATCTGCTGGTGATCACCAACT CAGCGTGCCAGGGAACCTGGATGCCCGGCATCGTCATCGCGTCCACGCTGTGCGTGAGCACCGCGCACGGCAGCAGCACCTGCCCCGGCGAC TCCGGCGGCCCGCTTGCCGTCGGCTCCGGCAACAACAGGCAACTGATCGGTATTACTTCTTTTGGAACTCAGTGGTGCGCTCAACACCACCC TGCTGGATTCGCTCGAGTCACCTCGTTTGCGTCATGGTTTAACAGCCATATGTAAAAAAACTACAACGTATAAATAAAAGTATAAGTCTTGT

ACCAAATAAATCTTTCACTAT

>DS5, 287 aa (SEQ ID NO: 45)

MKSMKSMKSSLLFLLVVAVAAAELLQPNTRYHETEGIPKFQLMKQLEEGTDFDGGRIWGGQAVSGGTHPHLGGLWITLTTGQNSICGSS
LVSNTRSVTAAHCWRTSTLQATMFTIVWNSNSIFWGGTRINTNQVIEHPNYNVWNLNNDVAVIIHNHVNFNNNIQPIALATGSQTYAGTWAV
AAGYGQTGDGNSPSGTKFQANLLVITNSACQGTWMPGIVIASTLCVSTAHGSSTCPGDSGGPLAVGSGNNRQLIGITSFGTQWCAQHHPAGF
ARVTSFASWENSIN

>DS6, 913 bp cDNA Sequence (SEQ ID NO: 36)

GGGCAAAAAAAATCCTTCTCGGGCTTCCAAAATGGCAGTAAAAACCGGAATACTTTTCTTCACCCTGCTCGTGGGATGTCTAGCTATCC
CCAAGCCCGCGTCGGATGACCTGTCCCAGTTCTTCGAGCATGCCAACCCAGATTCCCGCATCGTCGGCGGGACGGTGGCAGCCATCGGCGCC
CACCCTCACATGGTGGCCATGAGCAACGGTCTCCTGATCAGGAGCTTCGTTTGCGGTGGCTCTCTCATCTCCTCCCGTACTGTTCTGACCGC
TGCCCACTGCATCGCTGCTGTCTTCAGCTTCGGCTCTCTGAGCAGCTCCCTCCGCGTGACCGTCGGCACCAACAACTGGAACCAGGGTGGAG
TGGCCTACGCCCTGGCCCGCAACGTGACTCACGAGCACTACGTCAGCCAGATCATCAAGAACGACATCGGAGTGCTGATCACCTCCTCGCCT
GTGGTGTTCACCAATCTCGTCCAGCCCATCACTGTGTCTTATGATTACGCCGGTGCTGGAATCCAGTCCAGAGCCGCTGGTTGGGGCAGAAT
CAGGGCCGGCGGTCCCATCTCCGCTCAGCTCCTCGAGTTGACCGTGACCACCATCTCCGGCGATCAGTGCGTGCGTGGCGTGGCCCAGGCCT
CCGTCGACTTCAACGTCGCCGCCCCACCGGTGGAACCCCACATCGAACTCTGCATCATCCACTCGCCGAACCACGGCATGTGCAACGGTGAC
TCCGGCAGCGCTCTAGTCCGCCTGGACCGCGGCACCCAGATCGGAATCGTGTCATGGGGCTTCCCCTGCCCCGGCGCTCCCGATATGTT
CGTCCGAGTCAGCGCTTTCCAAGACTGGGTCGCCCGCCACTTCGTTGCTTGAATAAATGACTTGATATGATCGTGCAAAAAAAAAAA

>DS6, 281 aa (SEQ ID NO: 46)

MAVKTGILFFTLLVGCLAIPKPASDDLSQFFEHANPDSRIVGGTVAAIGAHPHMVAMSNGLLIRSEVCGGSLISSRTVLTAAHCIAAVF
SFGSLSSSLRVTVGTNNWNQGGVAYALARNVTHEHYVSQIIKNDIGVLITSSPVVFTNLVQPITVSYDYAGAGIQSRAAGWGRIRAGGPISA
QLLELTVTTISGDQCVRGVAQASVDFNVAAPPVEPHIELCIIHSPNHGMCNGDSGSALVRLDRGTQIGIVSWGFPCARGAPDMFVRVSAFQD
WVARHFVA

>DS10, 967 bp cDNA Sequence (SEQ ID NO: 37)

GGGAGCGTTCATTAACACTAACAACATGAAGGTACTTCTTGGGTCAGTGGTTCTGGTCTTGGCCATCGCGGCTTCTTATGCTGAGGGGC
CAGTTAACTACCATCAGAGGATTGGCATTCCTGAGGCAGCTAAGATCAGAAGGACTGAGGAAGATGCGGCCAAGGCTGGTGTCGATCTCAGA
ATCGTTGGTGGATCCAATGTTGACATCTCCCAAGTACCTTACCAAGTTGGTCTAGTCATCCAAATCCTGTGGATCCTGACTTCTGTGTGCGG
AGGCAGCTTGATCTCAAACACCCGTGTGATCACCGCTGCGCACTGCCACCATGACGGTAGCGTCACCGCTCAGTCCCACACCGTCGTGCTCG
GCTCCAACACTATCTTCAGCGGTGGTGTCCGTCAAACCACCTCTGACATTGTCATGCACCCACAGTGGACCCCGGAGACCGTTGCTAATGAC
ATTGCCGTCATTAGGATTAACGCTGTTACTTTCACCAATGTGATCCAGCCCATCTCTCTGCCCAGCGGATCTCAGCTAAATAACAACTTCGT
AGGCCAGGTCGGAATTGCTTCTGGATTCGGACGCACTTCTGATGGTGCTAACATCCCGAACAACCAACTCGTGAGCTGGGTGAGAGTGCCGA
TCATCACCAACCAGGCGTGCGCCTCAGTCTTCGGACCCTTCATCTTAAGTAGCACCATCTGCACCAACGGCTCTGGTGGTATGGGCACGTGC
CAGGGAGACTCTGGTGGTCCTCTCGCTGTGGAAGTTGGCAACTCTAGGGTCTTGGTCGGTGTGACTTCCTTTGGTGCTGCTGCCGGTTGCCA
AGCTGGATTACCTGCGGCGTACGCTCGCGTCACCTCATTCATCTCTTGGATCTTGGCCATATAAGTAAAATGATCTAACGAACCCTACCTGA
TCTGTAACGTGTGATTGTTATTAAATAATTTAAAAAATAAAAAAAAAAA

>DS10, 287 aa (SEQ ID NO: 47)

MKVLLGSVVLVLAIAASYAEGPVNYHQRIGIPEAAKIRRTEEDAAKAGVDLRIVGGSNVDISQVPYQVGLVIQILWILTSVCGGSLISN
TRVITAAHCHHDGSVTAQSHTVVLGSNTIFSGGVRQTTSDIVMHPQWTPETVANDIAVIRINAVTFTNVIQPISLPSGSQLNNNFVGQVGIA
SGFGRTSDGANIPNNQLVSWVRVPIITNQACASVFGPFILSSTICTNGSGGMGTCQGDSGGPLAVEVGNSRVLVGVTSFGAAAGCQAGLPAA
YARVTSFISWILAI

-continued

>DS12, 850 bp cDNA Sequence (SEQ ID NO: 38)

GGAAATAATTGTCATAAGCAAGATGAGTTTCAACAATAAAGTAGCGTTAGTGACTGGTGCGAGCTCTGGGATCGGAGCAGCTATTGCTC

TTAAATTCGCTGGAGAGGGAGCGAACGTTGCCATCGTTGGAAGAAACGCAGCTAAACTAAAAGATGTTACGGAAAGTATCTCGAAGGTCGGT

AACAAGCCTCTTGTGATCACCGCCGATGTTACCAAAGAAAGTGATGCTCAAAGAATCATCAACGATACAGTAAAACATTTTGGAAAACTTGA

CATTCTTGTCAACAATGCAGGAGTGATTCGCTATGCCAGCATTACTGAAGCAGAAGCCATGGCAGCATTTGACCATATCATGAGTACCAACC

TGCGTTCCGCTGTCTACATGACCAATCTGGCTGCCAAGCATCTTATTGAAACGAAAGGGAATATAATAAACATATCAAGCGTTACTGGTCAA

ATGGTGATGGAAAAATCGTTTGCTTACTGCACATCAAAAGCTGCCATGGATCATTTCGCGAGAGCAATCGCGTTGGACTTTGCGCCACATGG

TGTTCGCGTGAACAACATTAGCCCTGGGCCGGTGAGGACCGATATCGTTGAAAATATGGGAGTCAGTGCGGAGATTCAAGCAGCAGTATGGG

AAACATTCAAAGCAGCAACTCCTTTGAAAAGAATTAGTGAACCAAGTGAGATTGCCGAGCTAGCGGCGTTCTTGGCTAGTGACAAAGCTGTT

GGTATCACTGGATCAATTTACGTAACTGATAATGGAGTTTTGCTATCACGTTCAAAGTAATTCACTTAGACAAAAATATCTATTAATATACT

TAAGGTAACTTCTGAAAAAAAAAAA

>DS12, 256 aa (SEQ ID NO: 48)

MSFNNKVALVTGASSGIGAAIALKFAGEGANVAIVGRNAAKLKDVTESISKVGNKPLVITADVTKESDAQRIINDTVKHFGKLDILVNN

AGVIRYASITEAEAMAAFDHIMSTNLRSAVYMTNLAAKHLIETKGNIINISSVTGQMVMEKSFAYCTSKAAMDHFARAIALDFAPHGVRVNN

ISPGPVRTDIVENMGVSAEIQAAVWETFKAATPLKRISEPSEIAELAAFLASDKAVGITGSIYVTDNGVLLSRSK

>DS28, 1008 bp cDNA Sequence (SEQ ID NO: 39)

GGGGTTCTTGAAGAAACCATGACCATGGACAAACTGATTGTGTTAGCCGCCTGCATTGCCGCAGCCAGCGCACTTGGATCCTGGAAAAG

TGGATTGAGCGTGCGTTTTGGGGTTGGCCTCTTCGGATGGGGTTCTTCCTACTTCATTCATGTCCCCCAGACTGTGGCTGATGCCAAGAACT

CCCGCTGGTTGGAAACCCCAAGACCCGATGGCCCCCTGAGCAGTTTGATTATGATGTGTCCTTCCCAGAACGATGTGGTCCTCTGTGCCCTC

TATGATGACAATGGTGATGTGGCTGGTCTCCAGATTGCTCTGCCCACTGATAGTTACACCGGCGCTGTCTTGGACTGGGCTACCCAAGGCTA

CACGTACTGGACTGCACCGGCAAACTCTAATGGACAAGTTAGGAATTACTGGACCTTGCAGCAATACTTCGTTTCTGAAGCCACATTGAAGA

AGAGCAAGGAGGAGCGCCGCGCCTCCCGCGTGGCAGGCCGCGTACTGCAGGAGAATGCTGTGTGGGTCACCGGCTTCAACGGAGACCTGATG

AGGATCTCCGGCAACGCCAACGAGGTCACCGACACCGCCACCACCCACTTCACCAAACAAGCTTGCATTATTCTCATGGGTCGCCACTACTA

CTACAACATGACAACCGCCACCGAGTGCAGGTCTGACACCCTCCTGCCGTGGTTCCCACTGCTGGACGTGGGCACTGATCAGCTGATCGGCA

TGGGTTTCACGTCGTTTGGCCAGCTGCCCGCTAACGCCCTCGTCAAGGACTACTTCGAAAGGCCTAACGTGAGCAATGTTAAGTTGATAGTC

CCCGACGGCCCCGAATGCCTCTTCGAACTGGCGGACAGCCCTGGCCTGACCACCATGCACATCTACTACGTGGACTCACCCTGGCTCATCAA

CTGCATCAACAACTAGGCTCAAGAACTCTACCTCTGTCCTCTACACATGGAATGTAAATAGTTAATAAATTCTGCAGCCAAAAAAAAAAAA

>DS28, 304 aa (SEQ ID NO: 49)

MTMDKLIVLAACIAAASALGSWKSGLSVREGVGLFGWGSSYFIHVPQTVADAKNSRWLETPRPDGPLSSLIMMCPSQNDVVLCALYDDN

GDVAGLQIALPTDSYTGAVLDWATQGYTYWTAPANSNGQVRNYWTLQQYFVSEATLKKSKEERRASRVAGRVLQENAVWVTGENGDLMRISG

NANEVTDTATTHFTKQACIILMGRHYYYNMTTATECRSDTLLPWFPLLDVGTDQLIGMGFTSFGQLPANALVKDYFERPNVSNVKLIVPDGP

ECLFELADSPGLTTMHIYYVDSPWL INC INN

>D530, 798 bp cDNA Sequence (SEQ ID NO: 40)

ACATGGGGATGTTTTTCATCCTCGCAGTTTATCAGAACACAATTAAATTAATTAATTTAAAATGTTCAAATTAAGTTTCATTATTTTCA

TGTTGGTGGCTATTGCAACGTTTTAAGCAGTGACGCCCCAGCCCCAGACTGCACCTCGCCTCTTGAGACCGGACCATGCAGAGGCGGGAAG

GTTGCTTTCGGCTACGATACTGACTTGGAAGGATGCAAACAGTTCATCTACGGAGGATGTGACGGCAACGGCAACCGTTACAACACTCTAGA

GGAGTGTCAGGCTGCTTGCGAGAGTGACTGCAACAAATAATAACGAAATGCAAGCAATCAATTGGGTATTTGACAGCACAGTCAATTGACAT

ACTTTTTTTAAACTGTCAAAACGCACCATTCCCTATTTTTCACATTTTGCAAAGTAGAGGGAATCTAAAGGTCATAGCAGACTTATCAACTC

GGAAAGGGATCATGACGAGCTATCATCGCCTTTCCCGCGTTGTCAACTGTCAACTGCGAGGCGAGGCGTTTACGTTACTGTGCGGATAGGTG

TGGGTTACAGTATGGAGTTTCATACAAATACTGATCGCATCGAGTTGATACGGTTACAATCCCTGTCCGTGTTGATAAGTGTGCTACGTCCT

-continued

TGAGTTAGCAATGATAACTAAAGCTAAGTGGTGTCGTGTTATTATCGGTAATTAGTGTCAACTACCCAATTGTATCGATATGATTTACCTAA

AAGATGAGAAATATTCTTTTTATTTAACTATGTATTTATTATAAAAGCAACAGCCAAAAAAAAAA

>DS30, 83 aa (SEQ ID NO: 50)

MFKLSFIIFMLVAIANVLSSDAPAPDCTSPLETGPCRGGKVAFGYDTDLEGCKQFIYGGCDGNGNRYNTLEECQAACESDCNK

>D534, 624 bp cDNA Sequence (SEQ ID NO: 41)

AGTTTGTGAAGGACTCTGATCAAAATGGCATACTTTGGAAAGGAATTCTCCTTCGAAAGGGAAGAAAATTTCGATGCATTCGCCGATTT

TATCGGTGCCTTTGACGCCAACGCCAAGGGCTTCATGCAGTACAAGCCGAACCAGATCCTCGAGAAGAACGGGGACTCCTACAAGCTGATCT

TCAAGACCCCCGCCCTGAACCACGAGGTGGTGTTCAAGTCTGGAGTGCCTTACAGCGACGTCATCCGTGAAGGTTTGACGGCTGAATCCACC

ATCACCGTCGATGGAGACACCTTCACTCAGGTCCAGGACTACGGCCCCCTTGGCTCCATCACCTTCAAGAGAGAGTACAGCGCCGACCAACT

TAAAGTGACTGTCACCAGCAGTAAATGGGACGGCGTTGCCTACAGATACTACAAGGCGTAATCTTCCTACAGTTTAACTTAAGATTTAGGTA

GACTTTAAATTAATTTAATAACTCTGATTTGCTATAAATGTAAGCCAACGAAGAAATAATTTTAAAATTGCAGTTATAAACTAACTATTGTA

AATAACGAGACACCAATTCACAAGTTTTGATCTGTTATTGTAATAAAATACTTTTTCACCGAAAAAAAAAAAAAA

>DS34, 133 aa (SEQ ID NO: 51)

MAYFGKEFSFEREENFDAFADFIGAFDANAKGFMQYKPNQILEKNGDSYKLIFKTPALNHEVVFKSGVPYSDVIREGLTAESTITVDGD

TFTQVQDYGPLGSITFKREYSADQLKVTVTSSKWDGVAYRYYKA

>D535, 1433 bp cDNA Sequence (SEQ ID NO: 42)

ACATGGGAAGCAGTGGTATCAACGCAGAGTACATGGGAAGCAGTGGTATCAACGCAGAGTACATGGGGAGCTATCGAGATGAAGGTTTT

GGCGATCGCATTGCTTTTCGTGGCGGTCTACGCCAAGCACGAGGAATATGCTGGTTACAAATCCTACTGTGTAGGACAGAAGAACCAAGCAC

AGCAACATGCTCTGCAGTCCTTAGAGAATGAGTTCCAGCTAGACTTTCTGGGCCGTGTGACCAGCAGCCAGGAGACCTTGGTCCTGGTCAAG

CCTGAATTCCAGGCTGCGTTCACCAAAAGCCTGAAAGCCTTTGGCCTCTCCTACAGGGTCCATGCCGATGACGTAGTCAAAGCGCTCCAGAA

TGATGATAGGATTATCGAGGAGGTGGTTCAAGAGAAGGCCAGGAATGGGGGTGCCAGGATCCCTTATGACAATTATCAGCCTCTAAGTGTCT

ACGACGCCTACCTCGACGACATCGCTCGTCGCTACCCCAACGTGGTCACCCTCGTCAGCCCCGCCAACTCCTTCGAAGGCCGCCCCATCAAG

TACCTGAAGATATCCACCACCAACTTCCAAGACACCAGCAAGCCTGTCATCTTCATTGACGGAGGCATCCACTCCAGGGAATGGATCTCACC

ACCCACTGTCACTTGGGCGATCAGGAAACTGGTGGAGGATGTCACCGAACCTGACCTCCTGGAGAGGTTCGACTGGATCCTCTTGCCTATGG

TCAACCCTGATGGTTATGAACACAGCCACACATCTAACCGTTTCTGGAGGAAGACACGTTCGGCCACCAGCATTGCATTATGCCGGGGAGTC

GACGGCAACCGCAACTACGACTTCGCATGGAACACCGTCGGAACCAGCACCAACCCTTGCTCCGACACTTACGGAGGCCCTACAGCCTTCTC

CGAAATCGAGACCAGGGTTGTTCGTGACATCCTCCACGAGAACCTCAGCAGAATGGCTCTGTACCTCACCATGCATAGCTTTGGTAGCATGA

TCCTCTACCCTTGGGGACATGATGGTTCTTTATCCAACAACGCATTTGCACTCCAGACCGTTGGAGTTGCTATGGCTGATGAGATCTTCACT

CATAGTCTCCCTAATTTCCCTAGATATTCCGTTGGCAATTCTCTTCTGACTATTGGGTACGGCGCATCAGGTGCTTCTGAGGATTACGCTCA

CAGCATCGGCGTGCCCCTGTCGTATACTTACGAGCTTCCAGGGTTGAACGCTGGTATGAACGGTTTCATTCTGGACCCTCGGTTCATCGAGC

AGGTCTGCCGGGAGACTTGGGCAGGCATCGTCGTGGGCGCCAGGAGAGCTGGCGACCTCTTCGTCCCCATCCTTAAATTCTCTATTTGAAT

AAGTTGTTGATGATCTTTTTTTATAATAAACATTTTTATATTAAACAAAAAAAAAA

>DS35, 427 aa (SEQ ID NO: 52)

MKVLAIALLFVAVYAKHEEYAGYKSYCVGQKNQAQQHALQSLENEFQLDFLGRVTSSQETLVLVKPEFQAAFTKSLKAFGLSYRVHADD

VVKALQNDDRIIEEVVQEKARNGGARIPYDNYQPLSVYDAYLDDIARRYPNVVTLVSPANSFEGRPIKYLKISTTNFQDTSKPVIFIDGGIH

SREWISPPTVTWAIRKLVEDVTEPDLLERFDWILLPMVNPDGYEHSHTSNRFWRKTRSATSIALCRGVDGNRNYDFAWNTVGTSTNPCSDTY

GGPTAFSEIETRVVRDILHENLSRMALYLTMHSFGSMILYPWGHDGSLSNNAFALQTVGVAMADEIFTHSLPNFPRYSVGNSLLTIGYGASG

ASEDYAHSIGVPLSYTYELPGLNAGMNGFILDPRFIEQVCRETWAGIVVGARRAGDLFVPHP

Example 2: Extraction of Target Genes

1. Extraction of Asian corn borer total RNA

Asian corn borer 3 instar larvae are used as the starting materials. The RNA was extracted using the regular Trizol method, and purified using the regular purification method. The RNA sample was treated with DNase. This afforded an RNA sample with a concentration of ≥300 ng/ul, a total yield of ≥6 ug, OD260/280 1.8-2.2.

2. Isolation of mRNA and synthesis of DNA

The polyA containing mRNA was isolated with oligo-dT magnetic beads. Then, the first strand of cDNA was synthesized using random hexamer primers and the Superscript II reverse transcriptase reagent kit from Invitrogen.

3. Gene amplification and sequence determination.

Using specific primers for the target genes shown in TABLE 3, the desired genes are amplified. The collected gene fragments were purified, ligated into pMD18-T vector (Takara), and transfected into *E. coli* strain Top10. After blue-white selection, the positive strains were subjected to sequence determination.

Methods for dsRNA Synthesis:

(1) Primer Sequences

| | |
|---|---|
| (Sense Strand) F: | TCG GGATCC XXXXXXXXXX |
| (Sense Strand) R: | GAC AAGCTT XXXXXXXXXX |
| (Antisense Strand) F: | CTG CATATG XXXXXXXXXX |
| (Antisense Strand) R: | TCG TCTAGA XXXXXXXXXX |

Wherein TCG/GAC is a protection location, the underlined sequences are the forward strand BamHI/HindIII restriction site and the reverse strand NdeI/XbaI restriction site. XXX represents different primer sequences for different genes. The reverse strands are reverse complementary sequences, see TABLE 3.

Using Asian corn borer cDNA as a template to perform forward and reverse stand PCR amplification to obtain PCR products (amplification conditions: 94° C. 3 min, 94° C. 30 s, 55° C. 30 s, 72° C. 30 s, 72° C. 10 min). PCR products were analyzed on 1% agarose gel electrophoresis.

The obtained PCR products are separately ligated into modified pET-22b plasmid (the modified plasmid is obtained

TABLE 3

Primers Used In the Synthesis of dsRNA for the 10 Target Genes

| Name | Forward Primer | Reverse Primer |
|---|---|---|
| EYFP | TAATACGACTCACTATAGGGAGGACGACGGCA ACTACAAG(SEQ ID NO: 11) | TAATACGACTCACTATAGGGGAACTCCAGCAGG ACCATGT(SEQ ID NO: 12) |
| DS2 | TAATACGACTCACTATAGGGAGAGCACGAGGG CAGTCTCGGC(SEQ ID NO: 13) | TAATACGACTCACTATAGGGAGAGCGACCCGCT AGCTCTGCTG(SEQ ID NO: 14) |
| DS3 | TAATACGACTCACTATAGGGAGACGCACCGGCT CCAACGTCTT(SEQ ID NO: 15) | TAATACGACTCACTATAGGGAGACTGGCGCGGG TGGAACTACG(SEQ ID NO: 16) |
| DS5 | TAATACGACTCACTATAGGGAGACTGCGGCAGT TCGCTGGTCA(SEQ ID NO: 17) | TAATACGACTCACTATAGGGAGATGGACGCGAT GACGATGCCG(SEQ ID NO: 18) |
| DS6 | TAATACGACTCACTATAGGGAGAGTCCAGAGC CGCTGGTTGGG(SEQ ID NO: 19) | TAATACGACTCACTATAGGGAGACAAGCAACGA AGTGGCGGGC(SEQ ID NO: 20) |
| DS10 | TAATACGACTCACTATAGGGAGAGCGTCACCGC TCAGTCCCAC(SEQ ID NO: 21) | TAATACGACTCACTATAGGGAGACCGGCAGCAG CACCAAAGGA(SEQ ID NO: 22) |
| DS12 | TAATACGACTCACTATAGGGAGACGCTGGAGA GGGAGCGAACG(SEQ ID NO: 23) | TAATACGACTCACTATAGGGAGACCTCACCGGCC CAGGGCTAA(SEQ ID NO: 24) |
| DS28 | TAATACGACTCACTATAGGGAGAGCAGCTGGC CAAACGACGTG(SEQ ID NO: 25) | TAATACGACTCACTATAGGGAGACGGCGCTGTCT TGGACTGGG(SEQ ID NO: 26) |
| DS30 | TAATACGACTCACTATAGGGAGAGACCGGACC ATGCAGAGGCG(SEQ ID NO: 27) | TAATACGACTCACTATAGGGAGAGCACACTTATC AACACGGACAGGG(SEQ ID NO: 28) |
| DS34 | TAATACGACTCACTATAGGGAGAGCCTTTGACG CCAACGCCAAG(SEQ ID NO: 29) | TAATACGACTCACTATAGGGAGATCTGTAGGCAA CGCCATCCCA(SEQ ID NO: 30) |
| DS35 | TAATACGACTCACTATAGGGAGACAGCCCCGCC AACTCCTTCG(SEQ ID NO: 31) | AACGGTCTGGAGTGCAAATGCGT (SEQ ID NO: 32) |

Wherein, EYFP is an enhanced yellow fluorescence protein gene, used as an external gene control.

Example 3: dsRNA Synthesis

The methods described in this invention are applied in the studies of corn borer. The above-described 10 target gene fragments and an external control (EYFP) are cut from the pMD18-T vector (Takara Co.) and ligated into a modified pET-22b plasmid to obtain dsRNA that can be used in bioassays. The specific construction methods are as follows:

by adding "intro" between the NcoI and MscI sites). That is, the sense strand is ligated at the enzyme cut sites and then the antisense strand is ligated at the enzyme cut sites. The "intro" sequence is located between the two enzyme cut sites. After proving successful ligation, the final product is a closed circle with two inserted fragments.

The ligation products were transformed into HT115(DE3) (purchased from AddGene) competent cells (this bacteria strain is a defective *E. coli* strain, with the following characteristics: F-, mcrA, mcrB, IN (rrnDrrnE)1, rnc14:: Tn10 (DE3 lysogen: lavUV5 promoter-T7 polymerase).

Under tetracycline induction, through the influence of Tn10 transposon, induce RNase III gene loss. When induced with IPTG, HT115 may specifically express T7 polymerase, which through recognition of the T7 primer sequences at the insertion points, can produce and fold the product to produce dsRNA. The positive clones may be screened by blue-white selection.

Pick a single clone and transfer it into an LB culture medium containing 100 µg/ml ampicillin and 12.5 µg/ml tetracycline. Culture it at 37° C. for 10-14 hours.

Dilute the culture 100 folds and added it into a 2×YT culture medium (peptone 16 g, yeast extract 10 g, sodium chloride 4 g, dissolved in 1 L water, pH 7.0) until $OD_{600}$ reached 0.4. Then, 0.4 mM IPTG was added and cultured in a shaker for 4 hours to obtain the dsRNA expression products of the genes. (see, Ravi S Kamath, Maruxa Martinez-Campos, Peder Zipperlen, Anderw G Fraser, J. Ahringer, Effectiveness of specific RNA-mediated interference through ingested double-stranded RNA in *Caenorhabditis elegans*, Genome Biol 2, 0002.1 (2000).

The bacteria obtained above may be used directly. Alternatively, one may purify the recombinant plasmids and isolate dsRNA for use as pesticides.

Example 4: dsRNA Purification

Purify the dsRNA expression products obtained in the above described step. A method for purifying recombinant plasmids and isolating dsRNA is as follows:

(1) take 2 ml of bacteria culture for a small scale plasmid extraction to prove that the plasmids have been amplified. The remaining bacteria culture is put in a 50 ml centrifuge tube and centrifuged at 4° C., 5500 rpm for 10 min Remove the LB culture medium as much as possible by placing the centrifuge tube upside down;

(2) add 0.6 ml alkaline lysis buffer I (50 mmol/L glucose, 25 mmol/L Tris-HCl (pH 7.6), 10 mmol/L EDTA, dissolved in 1 L sterile water and sterilized at high temperature, add 1% RNase 0.5 ml). Resuspend the bacteria by pipetting or vortexing. Add 1 ml freshly prepared 10 mg/ml lysozyme, 13.3 ml freshly prepared alkaline lysis buffer II (0.2N NaOH, 1% SDS), and mix well by gentle rotation. Leave it at room temperature for 5-10 minutes. Do not leave it for more than 10 minutes. Add 10 ml ice cold alkaline lysis buffer III (5 mol/L potassium acetate 60.0 ml, glacial acetic acid 11.5 ml, $H_2O$ 28.5 ml) and mix well by gently inverting the tube. Place the centrifuge tube on ice for 10 minutes;

(3) centrifuge at 4° C., 20,000 g for 30 minutes. Based on the volume of the supernatant, add 0.6 fold volume of isopropanol and put into a new 50 ml centrifuge tube (if the volume is too large, then separate it into two tubes). Thoroughly mix it and then leave it at room temperature for 10 min. Centrifuge it at room temperature, 12,000 g for 15 min;

(4) discard the supernatant. Wash the tube wall with 70% alcohol and discard the alcohol. Place the tube upside down to dry it for 10-15 min. Dissolve the precipitate with 3 ml water, and place it on ice to precool it to 0° C. Add an equal volume (3 ml) of ice cold 5 mol/L LiCl. Mix well and then centrifuge at 4° C., 12,000 g for 10 min;

(5) transfer the supernatant to a new 50 ml centrifuge tube. Add an equal volume (6 ml) of isopropanol. Mix well and centrifuge at room temperature, 12,000 g for 10 min;

(6) after discarding the supernatant, place the centrifuge upside down to allow the liquid to drain dry. Wash the precipitate and tube wall with 70% alcohol at room temperature. Place the tube upside down to allow the alcohol to flow out and drain, thereby the alcohol in the precipitate would evaporate;

(7) use 500 µl water containing RNase A (20 µg/ml) to dissolve the nucleic acid precipitate. Transfer the solution to a 1.5 ml centrifuge tube and digest at 37° C. for 30 min;

(8) add an equal volume (500 µl) of phenol:chloroform. Mix well by vortex and centrifuge at the maximum speed at 4° C. for 2 min. Transfer the supernatant to another centrifuge tube (if there is too much protein film, repeat this step until protein is depleted);

(9) add an equal volume (500 µl) of chloroform. Vortex well to extract phenol. Centrifuge at the maximum speed at 4° C. for 2 min Transfer the supernatant to another centrifuge tube. Add 2 volumes of absolute ethanol (1 ml). Mix well and leave it on ice bath for 15-30 min to precipitate the nucleic acid. Centrifuge at the maximum speed at 4° C. for 5 min. Discard the supernatant and place the tube upside down to allow it to dry;

(10) add 1 ml of 70% ethanol, and wash the precipitate by inverting the tubes several times. Centrifuge it at 4° C. at maximum speed for 2 min. Discard the supernatant and place the tube upside down to allow ethanol to dry by evaporation;

(11) dissolve the plasmid precipitate with 1 ml water. Add 0.5 ml PEG-$MgCl_2$ solution, mix well and leave it at room temperature for not more than 10 min Centrifuge at room temperature at the maximum speed for 20 min to recover the plasmids;

(12) resuspend the precipitate with 0.5 ml 70% ethanol to remove PEG. Centrifuge at room temperature at the maximum speed for 5 min. Repeat the washing once. Discard ethanol and let it sit for 10-20 min to allow ethanol to evaporate;

(13) dissolve the wet plasmid with 200 µl $ddH_2O$ or TE(pH 8.0). Store the solution at −20° C.;

(14) digest the obtained plasmid with BamHI/HindIII to obtain specific dsRNA.

The above dsRNA is analyzed with electrophoresis after purification. For example, DS12 and DS28, having sizes consistent with the target fragments, were obtained as shown in the electrophoregram. The electrophoresis results are shown in FIG. 4.

Example 5: dsRNA Applications—Spray

Insect body permeation experiment: to prove that dsRNA can permeate (penetrate) insect body wall, inventors synthesized fluorescence labeled double stranded RNA (corresponding to DS12 and DS28). Cy3 fluorescence dye labeled dCTP was used to synthetize dsRNA (Ambion, MEGAscript RNAi Kit). After synthesis, 0.5 µl dsRNA was dropped on the back at the fifth segment of larvae of Asian corn borer. The larvae was then monitored under fluorescence microscope, as shown in FIG. 5A. Afterwards, the larvae were monitored every half an hour. It was found that dsRNA has penetrated into larvae body by 1 hour, see FIG. 5B. After 4 hours, dsRNA had spread to the entire body, see FIG. 5C.

Figure 2:
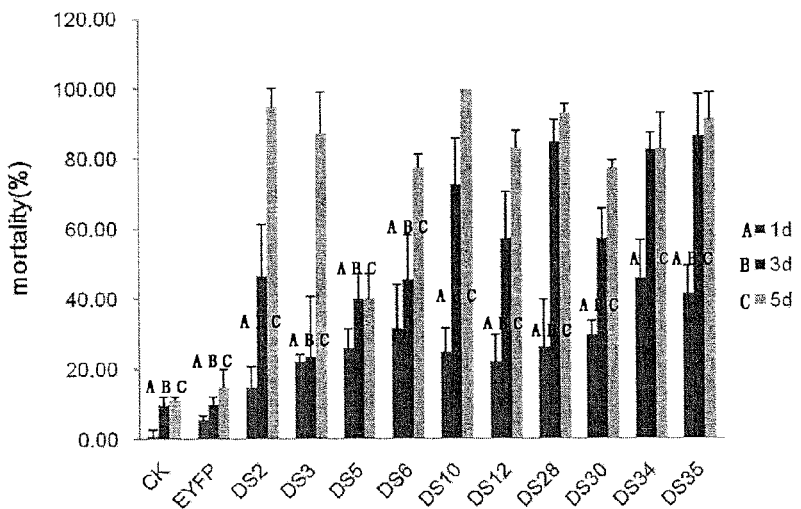
Figure 3:
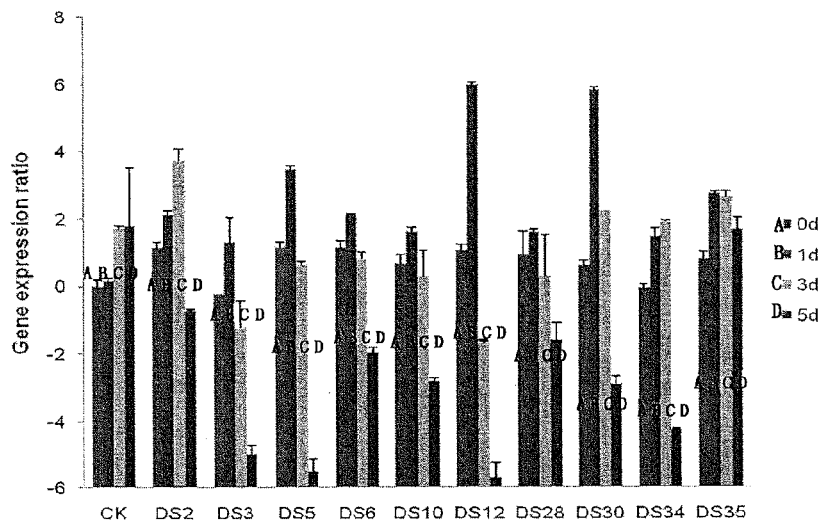
FIG. 3 shows results of real-time qPCR assessing the amounts of gene expression.

The inventors use the above obtained dsRNA (dissolved in $ddH_2O$, at a concentration of 50 µg/ml) to spray larvae of Asian corn borer (application amount is 300 µl/300-500 larvae). Five days after the application, dsRNA corresponding to 9 target genes (DS2, DS3, DS6, DS10, DS12, DS28, DS30, DS34, DS35) achieved over 70% mortality, as shown in FIG. 2. The blank control (CK) and an exogenous gene control (EYFP) did not produce appreciable mortality. Therefore, it is clear that RNA can entire insect body from body surface to inhibit target genes, resulting in insecticide effects. Thus, other nucleic acid inhibitors based on the target genes of the present invention may also be used as sprays to achieve insect killing effects.

qRT-PCR protocols are based on the operation procedures in the SYBR reagent box from TARAKA Co. qRT-PCR results proved that silencing of target gene can cause death, proving the reliability of the invention, as shown in FIG. 3.

Results

Through the dsRNA insect body permeation experiments, it is proved that it is possible to control pests using dsRNA spraying methods.

Example 6: Application of Host Expressing dsRNA—Feeding

The bacteria expressing dsRNA from EXAMPLE 3 were used in direct feeding experiments:
1. As described in EXAMPLE 3, culture the bacteria that express dsRNA at 37° C. until the culture reached an $OD_{600}$=about 0.8. Wait until $OD_{600}$ reaches 0.2, add 0.4 mM IPTG, and culture at 37° C. in a shaker until $OD_{600}$=about 2.0.
2. Mix the bacteria culture with the feed for Asian corn borer (0.1 ml/g feed). Feeds are replaced daily. Use a bacteria culture that does not express dsRNA as a blank control. In each treatment group, there are 50 larvae. They are observed daily to observe death rates. After feeding 1-7 days, analyze the results. The results are shown in FIG. 4. Feeding with hosts expressing dsRNA resulted in insect killing. In reality, it is the nucleic acid inhibitory effects of the dsRNA that produced insect killing. Therefore, the target gene dsRNA or other forms of nucleic acid inhibitors all can achieve insect killing via feeding.

TABLE 4

Corn borer larvae death rates after feeding on 20 μg/ml bacteria synthesized dsRNA

| Serial No. | Death Rate (%) |
|---|---|
| CK | 10 |
| dsEYFP | 10 |
| DS2 | 50 |
| DS3 | 56 |
| DS5 | 32 |
| DS6 | 20 |
| DS10 | 64 |
| DS12 | 48 |
| DS28 | 42 |
| DS30 | 46 |
| DS34 | 40 |
| DS35 | 26 |

Example 7: Shortened Forms of DS12 and DS28 and Their Effects

The inventors designed shortened dsRNA fragments based on DS12 (SEQ ID NO: 6) and DS28 (SEQ ID NO: 7).

DS12-M1 dsRNA: the methods for the synthesis and purification are as described in EXAMPLES 3 and 4. The difference is that the target gene fragment is at locations 1-488 in SEQ ID NO: 6.

DS12-M2 dsRNA: the methods for the synthesis and purification are as described in EXAMPLES 3 and 4. The difference is that the target gene fragment is at locations 7-491 in SEQ ID NO: 6.

DS28-M1 dsRNA: the methods for the synthesis and purification are as described in EXAMPLES 3 and 4. The difference is that the target gene fragment is at locations 1-433 in SEQ ID NO: 7.

DS28-M2 dsRNA: the methods for the synthesis and purification are as described in EXAMPLES 3 and 4. The difference is that the target gene fragment is at locations 4-433 in SEQ ID NO: 7.

As described in EXAMPLE 5, the above four (4) dsRNAs are sprayed on larvae of Asian corn borer (application amount 3000300-500 larvae). Five (5) days after application, these dsRNAs caused over 70% death rate in these larvae.

Example 8: Compositions

The formulation of agriculturally acceptable carrier for dsRNA (1 L system):

50 mM $NaHPO_4$, pH 7.0, 10 mM β-mercaptoethanol, 10 mM EDTA, 0.1% sodium lauryl sarcosine, 0.1% Triton X-100, add $H_2O$ to make it to 1 L The above formulation is a buffer formulation. It is only necessary to add any purified dsRNA into the buffer solution according to the desired concentration, such as 50 mg/L. One may also prepare a concentrate if necessary.

Example 9: Synthesis of Cotton Bollworm Full Length Target Genes and dsRNA

The full-length target genes described in EXAMPLE 1 are compared with the databank of cotton bollworm transcripts (Wang et al., PLoS ONE, 6(4):e18644; and Chinese Invention Patent Application No. 201010197328.9) to obtain 8 cotton bollworm target gene fragments that are homologous with the corn borer target genes described in EXAMPLE 1. Their full length sequences are as follows:

```
>HarmDS2
                                                                    (SEQ ID NO: 53)
    ATTCGAACATCGCGCACCGCAGTCTCGGCATCTACGCCCTGAACTGTATACGCGTCCGGGAGATCATCCCGCAGCGACTTCGACGAACA GGATAAGTTAAGCGAGCACAATGCCTTTCAAACCAGCAGATAACCCTAAGTGCCCTAAATGCGGCAAATCAGTATACGCAGCTGAGGAGAGA GTCGCCGGAGGACTCAAATGGCACAAAATGTGCTTCAAGTGCGGCCTGTGCCAGAAGTTGCTGGACTCCACCAACTGCTCAGAACACGAAGG TGAACTGTACTGCAAAGTGTGCCATGCACGTAAATTCGGACCAAAAGGCTACGGCTTCGGCGGTGGTGCTGGCTGCCTGTCCATGGACACTG GTGACCACCTGAAGGCTGAGAATGCGAATTGAGCGAGCAGCCCTCCAGCAGAACTAGCGGGTCGCCGACACACATCTCGGCCCACCAGCGAC GCCTCGCGAACGCACGCCATACTGTACTTTAAATTACTCTAGTTAGGATTATTTATTCGCTATCGCTTAATTTAATTTGTTCATCGGTATTA
```

-continued

TTTATTATTTATAAAAAACACAAATAAATAAAACAGTCGACTGTTTTATTTATTTGTGTTTTTTATAAATAATAAATAATACCGATGAA 85.3% homology with the related sequences from corn borer.

>HarmDS5

(SEQ ID NO: 54)

ACATGGGGAGTATTTGTTAGATTAGGTACGTTACCAGTGTTGCGTCTTGTAGAACATTAGTTTAATTTTTTTGTAGTTTCAGCTCCTAG

TTTTGCCTGGAAACACGATGAAAACCTTCATTGTAGTGTGTTTGGCTCTGGCTAGCTTCGCCTGTGCGGAGCAGGGATCTTTCCCTGGGTAC

TCCACGTTTGGGTACCTAGAGAAGTATGCTATTCCTCATGCGGAGAAACTTCGCGCGGCTGAGGAAAAGTTCCTCGCTAGCCAGTCTGGCTC

CAGGATCGTAGGTGGAGTTCCCGCTGGCCAGGGACAGTACCCATACCAGGCTGGTCTCCTCCTCTCCATCATCGGTTTCGAAGGCAACGGTA

TCTGCGGAGGCTCCCTGATCAGCGCCAACCGAGTAGCAACAGCCGCCCACTGCTGGTTCGACGGTATCCACCAAGGATGGAAGGTCACAGTT

GTGCTCGGTTCCACCCTGCTGTTCTCTGGAGGCACTCGTCTTGAGACAGTGTGGTCGCCATGCACCCTAACTGGACTCCTGCACTCGTCCG

CAATGATGTTGCTGTGATTTACTTGCCCAACTCYGTRCAGATTTCAGCCAATATTGCACCAATTGCTTTGGCTAGCGGMTCTTCAGAATTCG

CCGGTGTCTCCGCCATTGCCTCCGGTTTTGGATTAACCAGCTCTAGCGGACAAATCACCGCTAACCAGTTCCTGAGCCACGTCAACCTGAAC

GTGATCACCAACATCGCCTGCAGCGTCGCCTTCCCCTTCATTGTCCAGCCTTCCAACATCTGCACCAGTGGTATCGGAGGTGTTGGTACTTG

CAGCGGTGACTCTGGTGGTCCTCTGGTCACCAACCAGAATGGACAGAACGTCTTGATTGGTATCACTTCCTTCGGCTCGGCTTTCGGCTGCC

AGGTCAACCTGCCCTCAGTCTTCGCTCGTGTCACATCATTCGTCTCTTTCCTCAACCAACATTTGTAATTCTGAACAAACTGTAAACTATAC

TGTAAATAAGACTGGAGTTGGAATCTTTTCCAGCATATTCGTTGTATTTTTACAAAAAAATTGAAGCTATATAATAAGCAATAAAATAAAT

CTGCTCTCGTAAAAAAAAAAAA 60.7% homology with the related sequences from corn borer.

>HarmDS6

(SEQ ID NO: 55)

TTTTTTTTTTTTTTTCATTCAAATTCATTTATTTCTCCCCATTAAATTAAGATGCAGTCTTAAGCAGTTTCCAAAGTCCTTTTATCGGA

ATATTTACAAGTCCTTTAGTCTGTCTATTTAGACTACATTAGCCTGGAGCCAGGACTGGTAGGCGCTGACTCTGACGAACATGTCGGGGGCG

CCGCGGGCGCAGGGGAAGCCCCAGGACACGATGCCGAACTGCTGGCCGTTGTCGGCGCGGGTCAGAGCGCTGCCGGAGTCACCATTGCAAGT

TCCGAATCCAGGAGCGTGGAAGGTGCAGACCTCGATGTGAGGTTCAACGGGAGGAGCGCGTACATTCAGCTCGACGGAGGCGCGGGCCACGC

GAGCCACGCAGTCGTTACCGTCGATGGTGGTGGGAACAGCTCCAGGAGAGTGGCTGAGAGGGCACCGCCAGCCCTGATTCTACCCCATCCA

GCGACCCTAGCGTTAACACCACCAGGGATGTGAGCGTAAGTCAGAGGCACAGTCCTGACGAGGTTGTTCAGAGCCACGTTGTTGGAGGTGAT

GAGGATACCGATGTCGTTCTTGATGGTGGCAGACACGTAGTTGGGGTGGGTGACGTTGCGGGCCAAGGTGTAGGCCACGCCGCCGCTGTTCC

AGCGGTTTGTGCCGACTGTCACGCGGAGAGAGTTAACCAGCGAGCCACCACTGAACACCGCAGCGATACAGTGAGCAGCTGTCAGCACAGTC

CTAGTCGTGATCAAGGAACCGCCGCAGAGGAAGCTCCTCACCAGCACGCCACTGGACATGGCCACCATGTGAGGGTGGCTGCCCACAGCCGC

CTGGGTGCCGCCAACGATGCGAGCGCTGGCGTCAGTGTGGTCGAAGAAGCGTGACATGTCATCTTCGGGCGCGGGGAGGGCAATACACCCAA

CCAGGAGCGAGATCACCAGAAGTCCGGTTTTGAAGTCCATGTTTAACAACG 71.9% homology with the related sequences from corn borer.

>HarmDS10

(SEQ ID NO: 56)

ATCCAAGAATTCGCACGAGACAAATCAACATGAGCTGTCCCTAGGAGTGTGCTAGCTTGGCCGTCGCCGTATCGGCAGTGGAGATCGCC

ACTCCTGATGCCGACAGCCCTGTCTTCGGCTACCACGCCAAGTTTGGTATTGCTGAGGCTGCGAGGATCAAGAGCGCGGAGGAAGTTCAGAG

CTTCAACGGCCAGAGGATCGTTGGAGGATCCATCACCAACATTGCCAACGTCCCATACCAGGCTGGTCTTGTGATCACCATCTTCATCTTCC

AATCCGTGTGCGGTGCTTCCCTCATCTCCCACAACCGCCTGGTGACTGCTGCTCACTGCAAATTCGACGGTGTCTTGAACGCTAGCTCCTTC

ACCGTTGTGCTTGGCTCCAACACCCTGTTCTTCGGCGGTACTCGCATCAACACCAATGATGTCGTCATGCACCCCAACTGGAATCCTGCTAC

CGTTGCCAATGACATCGCTGTCATTCGCATCAGTTCCGTCAGCTTCAACAATGTGATCCAGCCCATCGCTCTTCCCAGTGGAGACGAACTCA

ACAACCTCTTCGTCGGCGCCAACGCTCTTGCCTCCGGATTTGGCCGCACTAGCGACAGTGGAAGCATTGGTACCAACCAACAGCTGAGCTCT

GTGACCATCCCCGTGATCACCAACGCTCAGTGCGCTGCCGTGTACGCCCCGCCTTTGTGCACGCCTCCAACATCTGCACCAGCGGCGCCGG

CGGCAAGGGTACTTGCAACGGTGACTCCGGTGGCCCTCTCGCTGTCGACAGCAACAACAGGAAGATCTTGATCGGTGTTACTTCATACGGTG

CTGCTGACGGTTGCGCCGCTGGTTTCCCTGCTGCCTTCGCCAGAGTCACCTCCTTCGTCAGCTGGGTCCAGTCCCAATAATCTCCTCCTCTC

TTAAACTTATAATGCTTAAATTAAATTTATTTTACTTCAAAAAAAAAAAAAAA 65.2% homology with the related sequences from corn borer.

>HarmDS12
(SEQ ID NO: 57)
AGAAACTGAAGAATACTGCCAAGAAATGTGGAAACCCTTTAGTGATCGTCGCTGATGTCACAAAAGAAGACGACGTCAAAAGAATTGCC AGTGAAACGTTGAAACATTTTGGGAAACTCGATGTTCTGGTCAACAATGCTGGCATTTGTCCATTTGCTAGTATTCAAGCTGACAACGCAAT GCAGGTCTACGATGAAATAATGTCTACAAACCTCCGGTCTACCGTTCTACTGACACATCTTACCGTCCCTGAACTTGTGAAAACTAAAGGCA ACATTATCAATATTTCAAGTGTTGCTGCTTTCAAAGTCGCTCTAGGTCTTTTTGCGTACTGTGCGTCGAAGGCAGCTATGGATCACTTCTCT AGAGCGATTGCACTAGAGCTGGCTCCAAGTGGTGTACGTGTAAATGTAGTCAATCCAGGACCCGTGGCGACTGACATCGGTGCTACCATGTT CCCAACAAAAGAGGAACAAGACAATTTCTTTAAAAAAGTCGTGGATGGAACTGCATTGGGCAGGATATCGGAGCCTGAAGAAATAGCTGATA TTGTTCTGTTCCTAGCGAGTGATAAAGCTAGAGGGATCACCGGTTCAAGTTATGTTTCTGATAATGGATATTCGGTTAAAGGCGTACAAGCT TGATTAATTTTATTAATAAACGTAATTTTAAATAGTGC
68.8% homology with the related sequences from corn borer.

>HarmDS28
(SEQ ID NO: 58)
AGACCGGCCCTACCCTCCCAAGTGGCTATGAGAACCTGGTACTGTATGGCCCCGCTGACGACAACACCCTCAACTTATACTACGATGAC AACTATCAGATTGCTGCATTCCAAATTGGTCTGGACAAAGAACAAATAAGCGATTCGGTATACGATTTCGAAAATCAAGGATTCGCAAGCTG GACCACTACATTGTCTAATGGCACATCTAGAGATTATTGGACCATCAGAGCATACTTTTCCACTGCTGATTATCTTGCGACTGACGCAACAA CTCGCAACTCTTCAAGAAATACTGAGACGTTGATCCAGGGTGGTTCCATGGTAGTGACTGGTTTCAACGGAGAATTGTACACCATTTCCTCC GACCCTACCGTACTTGCCGACACAAGCGTCAGTGGGTTCACAGAACAAGCCTGCATGATATATGGGTCACCATTTCTACTACAACATGAC TACAAGCTTGGAGTGCGCTGAAGGAAGGCTGTTCCCCTGGTTCCCACTTTCCTACAACGGAGTAGTGATGGGCATTGGTTTCAACTTTATCG GCAAATACGACGTGAGACCTGACAATTTCAATTATTTCGAAAGCCCTGGAGTAGCAGCTGTTAAGATCATCGTACCAAAAGGCCCGCAATGT TTCTACGAGTTAGCAGAAAACCCCGGCGTGG
71.5% homology with the related sequences from corn borer.

>HarmDS34
(SEQ ID NO: 59)
TTCAGTCAACATGTCTTTCCTTGGCAAAACTTACACCTTCGTCAAACAGGAGAATATGGACGGATTCCTGAAATCTGTCGGTCTCCCTG ACGACAAAATCGAGCCAGTCCTGAAGTTCACTCCTGAACAGAAGATCATTCAGGAAGGTGATGGCTACAAGTACATCACTCAGGGTCGCGAT GGCCCTAGAGAAGTCACATTCAAGTCCGGAGTAGAATTCGACGATCTTATTGGACCTGAGAAAATTCCCGCTAAGACTACATACGTCGTTGA TGGCAACAAAGTGACACAGACCATCAAATCAGCTATGGGAGTCGGCACCTTCACCAGGGAGTTCGTTGGCGATGAACTTATCATCACCATGG TCACCGACAAATGGGACGGCGTTGCCAAGAGATAC
73.2% homology with the related sequences from corn borer.

>HarmDS35
(SEQ ID NO: 60)
CATTCCTCGAAAGGTCGTCCCATCAAGTACGTCAAAATCCTCCACAACCTACTTTGAAGACCACAGCCAAGCCTGTCATCCTCATCGAT GGTGGTATCCACGCCAGGGAAATGGATCTCTCCCCCCACTGTTACCTTGGGCTATTCATAAGCTGGTTGAAGATGTTACTGAAAGAGATCTT CTAGATAATTTTGACTGGATCCTCTTGCCTGTGGTCAACCCTGATGGATATAAATTCACTTTTACCAATTCCCGTTTCTGGCGTAAGACTCG TTCCACGGACCAGCACGTTTTAAGCGGTATCTGCCCAGGAGTCGACGGTAACCGCAACTATGACTTCTTCTGGAACACCGTIGGTACCAGCA ACACCCCATGCTCAGACGTCTACGCTGGATCCAGAGCCTTCTCCGAAGTCGAAACCAGGGTCGTCAGAGATATCCTCCATGAACATTTAGCA CGCATGGCTCTGTACATCACCATGCACAGTTTCGGAAGCATGATCTTATACCCATGGGGTCATGATGGCTCCCTATCTCATAACGGCCTTGG TCTTCATACGGTGGGAGTTGCTATGGCAACGGCAATCAATCAGAATTCTCTATCTCACTTCCGATCTTATGTTGTTGGAAATTCAGCTTTAG TTCTGAACTATCCAGCGGCTGGTGCGTCAGAAGATTATGCTCATCAAATTGGCGTGCCTCTATCCTATACTTTTGAGCTACCTGGTCTATCC AACACATTACTTGGATTCAATTTGAACCCTAGGTACATTCAACAAGTATGCAATGAAACTTGGCAAGGTCTCATCGTTGGAGCTAGGAGAGC

TGGTGATTTATTTAGAAATAAAAAACTTTAAAGACTGAAAAAAAAAAAAAAAAAAAAAAAAAAAAAAAAAAA 79.9% homology with the related sequences from corn borer.

Using the full-length target gene sequences of cotton bollworm as PCR amplification template and the primers of TABLE 6, dsRNA of 8 cotton bollworm target genes are obtained using the methods described above.

TABLE 6

Primers Used in the Synthesis of dsRNA of 8 Target Genes of Cotton Bollworm

| Name | SEQ ID NO: | Primer (5'→3') |
|---|---|---|
| Harm ds2 F | 101 | TAATACGACTCACTATAGGGAGAACATCGCGCACCGCAGTCTC |
| Harm ds2 R | 102 | TAATACGACTCACTATAGGGAGATCGCTGGTGGGCCGAGATGT |
| Harm ds5 F | 103 | TAATACGACTCACTATAGGGAGACCCGCTGGCCAGGGACAGTA |
| Harm ds5 R | 104 | TAATACGACTCACTATAGGGAGACAGCCGAAAGCCGAGCCGAA |
| Harm ds6 F | 105 | TAATACGACTCACTATAGGGAGAAGCCAGGACTGGTAGGCGCT |
| Harm ds6 R | 106 | TAATACGACTCACTATAGGGAGAGCCATGTCCAGTGGCGTGCT |
| Harm ds10 F | 107 | TAATACGACTCACTATAGGGAGATGTGCTAGCTTGGCCGTCGC |
| Harm ds10 R | 108 | TAATACGACTCACTATAGGGAGATGCAAGTACCCTTGCCGCCG |
| Harm ds12 F | 109 | TAATACGACTCACTATAGGGAGATGTGGAAACCCTTTAGTGATCGTCGC |
| Harm ds12 R | 110 | TAATACGACTCACTATAGGGAGATCAGGCTCCGATATCCTGCCCA |
| Harm ds28 F | 111 | TAATACGACTCACTATAGGGAGAGACCGGCCCTACCCTCCCAA |
| Harm ds28 R | 112 | TAATACGACTCACTATAGGGAGATGGGAACCAGGGGAACAGCCT |
| Harm ds34 F | 113 | TAATACGACTCACTATAGGGAGATTCAGTCAACATGTCTTTCCTTGGCA |
| Harm ds34 R | 114 | TAATACGACTCACTATAGGGAGAGTATCTCTTGGCAACGCCGTCCC |
| Harm ds35 F | 115 | TAATACGACTCACTATAGGGAGAAGACCACAGCCAAGCCTGTCA |
| Harm ds35 R | 116 | TAATACGACTCACTATAGGGAGATCTTCTGACGCACCAGCCGC |

Example 10

Applications of dsRNA of Cotton Bollworm Target Genes—Spray

The inventors sprayed the dsRNA obtained in EXAMPLE 9 (dissolved in dd H₂O at a concentration of 50 µg/ml) directly on larvae of Asian cotton bollworm (application amount 300 µl/300-500 larvae). Compared with the blank control (CK) and an exogenous gene control (EYFP), the dsRNA corresponding to each target gene increased the death rate of cotton bollworm (TABLE 6, and FIG. 6). Therefore, it is clear that nucleic acid inhibitors based on target genes of the invention can cause death in pests.

TABLE 7

Death Rates of Cotton Bollworm larvae Feeding on dsRNA

|  | 1 Day | 3 Days | 5 Days |
|---|---|---|---|
| CK | 5.56 ± 6.36 | 12.50 ± 4.17 | 16.67 ± 0.00 |
| EYFP | 6.25 ± 2.95 | 14.58 ± 2.95 | 18.75 ± 2.95 |
| DS2 | 16.67 ± 11.79 | 54.17 ± 17.68 | 70.83 ± 23.57 |
| DS5 | 10.42 ± 2.95 | 22.92 ± 8.84 | 22.92 ± 8.84 |
| DS6 | 29.17 ± 5.89 | 39.58 ± 8.84 | 43.75 ± 8.84 |
| DS10 | 20.83 ± 17.68 | 27.08 ± 14.73 | 33.33 ± 5.89 |
| DS12 | 22.92 ± 2.95 | 37.50 ± 11.79 | 39.58 ± 8.84 |
| DS28 | 10.42 ± 2.95 | 37.50 ± 5.89 | 45.83 ± 5.89 |
| DS34 | 25.00 ± 5.89 | 45.83 ± 5.89 | 56.25 ± 8.84 |
| DS35 | 29.17 ± 5.89 | 50.00 ± 11.79 | 58.33 ± 11.79 |

All literatures discussed in this invention are incorporated by reference in this application, as if they were individually cited as references. In addition, it should be understood that after read the disclosure of the invention, one skilled in the art would know how to vary or modify the invention. These equivalents should fall within the scope of the claims in this application.

What is claimed is:

1. A dsRNA having the following structure:

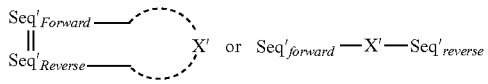

wherein

Seq'$_{Forward}$ or Seq'$_{Reverse}$ contains an RNA sequence complementary to at least 21 consecutive nucleotides of the nucleotide sequence of SEQ ID NO: 33;

Seq'$_{Forward}$ and Seq'$_{Reverse}$ are complementary to each other;

X' is null or a spacer sequence between Seq'$_{Forward}$ and Seq'$_{Reverse}$, and the spacer sequence is not complementary to Seq'$_{Forward}$ or Seq'$_{Reverse}$;

|| indicates formation of hydrogen bonds between Seq'$_{Forward}$ and Seq'$_{Reverse}$.

2. A construct expressing the dsRNA according to claim 1.

3. A host cell comprising the dsRNA according to claim 1.

4. A preparation for pest control, comprising: a safe and effective amount of the dsRNA of claim 1 and an agriculturally acceptable carrier.

5. The construct according to claim 2, wherein the construct comprises the following structure:

Seq'$_{forward}$-X'-Seq'$_{reverse}$ wherein

Seq'$_{Forward}$ or Seq'$_{Reverse}$ is a polynucleotide comprising a sequence of at least 21 consecutive nucleotides of the nucleotide sequence of SEQ ID NO: 33;

Seq'$_{Forward}$ and Seq'$_{Reverse}$ are complimentary to each other;

X' is a spacer sequence between Seq'$_{Forward}$ and Seq'$_{Reverse}$, and the spacer sequence is not complementary to Seq'$_{Forward}$ or Seq'$_{Reverse}$;

|| indicates formation of hydrogen bonds between Seq'$_{Forward}$ and Seq'$_{Reverse}$.

6. The dsRNA according to claim 1, wherein the dsRNA inhibits growth of corn borer.

* * * * *